US010913775B2

(12) United States Patent
Russell et al.

(10) Patent No.: US 10,913,775 B2
(45) Date of Patent: Feb. 9, 2021

(54) TREATING CANCER WITH VIRAL NUCLEIC ACID

(71) Applicant: Mayo Foundation for Medical Education and Research, Rochester, MN (US)

(72) Inventors: Stephen James Russell, Rochester, MN (US); Elizabeth J. Kelly, Rochester, MN (US); Elizabeth M. Hadac, Oronoco, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/937,567

(22) Filed: Mar. 27, 2018

(65) Prior Publication Data

US 2018/0215794 A1 Aug. 2, 2018

Related U.S. Application Data

(63) Continuation of application No. 14/792,178, filed on Jul. 6, 2015, now Pat. No. 9,957,302, which is a continuation of application No. 13/952,343, filed on Jul. 26, 2013, now abandoned, which is a continuation of application No. 12/528,047, filed as application No. PCT/US2008/054459 on Feb. 20, 2008, now abandoned.

(60) Provisional application No. 61/009,968, filed on Jan. 4, 2008, provisional application No. 60/902,200, filed on Feb. 20, 2007.

(51) Int. Cl.
*C07K 14/005* (2006.01)
*A61K 35/768* (2015.01)
*C12N 7/00* (2006.01)

(52) U.S. Cl.
CPC .......... *C07K 14/005* (2013.01); *A61K 35/768* (2013.01); *C12N 7/00* (2013.01); *C12N 2770/32311* (2013.01); *C12N 2770/32332* (2013.01); *C12N 2770/32611* (2013.01); *C12N 2770/32632* (2013.01); *C12N 2840/102* (2013.01); *Y02A 50/30* (2018.01)

(58) Field of Classification Search
CPC .................................................... C07K 14/005
See application file for complete search history.

(56) References Cited

U.S. PATENT DOCUMENTS

| | | | |
|---|---|---|---|
| 6,071,742 | A | 6/2000 | Tracy |
| 2003/0027322 | A1 | 2/2003 | Federoff et al. |
| 2003/0040498 | A1 | 2/2003 | Ansardi et al. |
| 2003/0077251 | A1 | 4/2003 | Escriou |
| 2005/0227935 | A1 | 10/2005 | McSwiggen et al. |
| 2006/0185027 | A1 | 8/2006 | Bartel et al. |
| 2010/0041737 | A1* | 2/2010 | Naldini et al. .............. 514/44 R |
| 2010/0111873 | A1 | 5/2010 | Russell et al. |
| 2013/0345414 | A1 | 12/2013 | Russell et al. |
| 2015/0299271 | A1 | 10/2015 | Russell |

FOREIGN PATENT DOCUMENTS

| | | |
|---|---|---|
| EP | 1290205 | 10/2005 |
| KR | 10-20070115321 | 12/2007 |
| WO | WO 2004/043387 | 5/2004 |
| WO | WO 2004/076622 | 9/2004 |
| WO | WO 2005/087931 | 9/2005 |
| WO | WO 2006/017914 | 2/2006 |
| WO | WO 2007/000668 | 1/2007 |
| WO | WO 2007/003229 | 1/2007 |
| WO | PCT/IB2006/002266 | 4/2007 |

OTHER PUBLICATIONS

Shafren et al. (Clin Cancer Res 2004; 10: 53-60). (Year: 2004).*
Sprunt et al. (Experimental Biology and Medicine. Aug. 1, 1959. 101: 604-608 ) (Year: 1959).*
Hughes et al. (J. Gen. Virol. (1989) 70: 2943-2952). (Year: 1989).*
Adachi et al., "Destruction of human retinoblastoma after treatment by the E variant of encephalomyocarditis virus," J. Neurooncol., 2006, 77(3):233-240.
Anderson et al., "MIR-206 regulates connexin43 expression during skeletal muscle development," Nucleic Acids Res., 2006, 34:5863-5871.
Authorized Officer Kyung Joo Cho, International Preliminary Report on Patentability, PCT/US2008/054459, completed Jun. 2, 2009, 10 pages.
Authorized Officer Kyung Joo Cho, International Search Report and Written Opinion of the International Searching Authority, PCT/US2008/054459, dated May 22, 2008, 12 pages.
Babak et al., "Probing microRNAs with microarrays: Tissue specificity and functional inference," RNA, 2004, 10:1813-1819.
Barton et al., "5' cloverleaf in poliovirus RNA is a cis-acting replication element required for negative-strand synthesis," EMBO J., 2001, 20:1439-1448.
Baskerville et al., "Microarray profiling of microRNAs reveals frequent coexpression with neighboring miRNAs and host genes," RNA, 2005, 11:241-247.
Belsham and Sonnenberg, "RNA-Protein Interactions in Regulation of Picornavirus RNA Translation," Microbiological Reviews, Sep. 1996, pp. 499-511.
Bhattacharyya et al., "An Apical GAGA Loop Within 5' UTR of the Coxsackievirus B3 RNA Maintains Structural Organization of the IRES Element Required for Efficient Ribosome Entry,"RNA Biology, 2006, 3(2):60-68.

(Continued)

*Primary Examiner* — Scott Long
(74) *Attorney, Agent, or Firm* — Fish & Richardson P.C.

(57) ABSTRACT

This document provides methods and materials related to the use of nucleic acid coding for viruses to reduce the number of viable cancer cells within a mammal. For example, methods for using infectious nucleic acid to treat cancer, engineered viral nucleic acid, methods for making engineered viral nucleic acid, methods for identifying infectious nucleic acid for treating cancer, methods and materials for controlling virus-mediated cell lysis, and methods and materials for assessing the control of virus-mediated cell lysis are provided.

3 Claims, 37 Drawing Sheets

Specification includes a Sequence Listing.

(56) References Cited

OTHER PUBLICATIONS

Bledsoe et al., "Cytokine production in motor neurons by poliovirus replicon vector gene delivery," Nature Biotechnology. Sep. 2000; 19(9): 964-969.
Brown et al., "Endogenous microRNA regulation suppresses transgene expression in hematopoietic lineages and enables stable gene transfer," Nat. Med., 2006, 12:585-591.
Calin et al., "Frequent deletions and down-regulation of micro-RNA genes miR15 and miR16 at 13q14 in chronic lymphocytic leukemia ," Proc. Natl. Acad. Sci., 2002, 99:15524-15529.
Campbell and Gromeier, "Oncolytic viruses for cancer therapy I. Cell-external factors: virus entry and receptor interaction," Onkologie, Mar. 2005, 28(4):144-149.
Campbell and Gromeier, Oncolytic viruses for cancer therapy I. Cell-internal factors for conditional growth in neoplastic cells, Onkologie, Apr. 2005, 28(4):209-215.
Carlisle et al., "Use of synthetic vectors for neutralising antibody resistant delivery of replicating adenovirus DNA," *Gene Ther.*, 13(22):1579-1586. Epub Jun. 29, 2006.
Chen et al., "MicroRNAs Modulate Hematopoietic Lineage Differentiation," Science, 2004, 303:83-86.
Cullen, "Viruses and microRNAs," Nature, 2006, 38:S25-S30.
Davis and Fang, "Ocolytic virotherapy for cancer treatment: challenges and solutions," J. Gene Med., 2005, 7(11):1380-1389.
Emerson et al., "cDNA clone of hepatitis A virus encoding a virulent virus: induction of viral hepatitis by direct nucleic acid transfection of marmosets," *J Virol.*, 66(11):6649-6654, Nov. 1992.
Felli et al., "MicroRNAs 221 and 222 inhibit normal erythropoiesis and eiythroleukemic cell growth via kit receptor down-modulation," Proc. Natl. Acad. Sci., 2005, 102:18081-18086.
Fu et al., "Identification of human fetal liver miRNAs by a novel method," FEBS Lett., 2005, 579:3849-3854.
Hadac et al., "Coxsackievirus A21 has potent oncolytic activity in multiple myeloma," Molecular Therapy, Acadamic Press, San Diego, CA, 2006, 13(1): S168.
He et al., "A microRNA polycistron as a potential human oncogene," Nature, 2005, 435:828-833.
Hermiston and Kirn, "Genetically based therapeutics for cancer: similarities and contrasts with traditional drug discovery and development," Mol. Ther., Apr. 2005, 11(4):496-507.
Jopling et al., "Modulation of Hepatitis C Virus RNA Abundance by a Liver-Specific MicroRNA," Science, 2005, 309:1577-1581.
Kloosterman et al., "Substrate requirements for let-7 function in the developing zebrafish embryo," Nucleic Acids Research, 2004, 32(21):6284-6291.
Lagos-Quintana et al., "Identification of tissue-specific microRNAs from mouse," Curr. Biol., 2002, 12:735-739.
Lian et al., "Recovery of infectious type Asial foot-and-mouth disease virus from suckling mice directly inoculated with an RNA polymerase I/II-driven unidirectional transcription plasmid," *Virus Res.*, 208:73-81, Epub Jun. 16, 2015.
Lim et al., "Microarray analysis shows that some microRNAs down regulate large numbers of target mRNAs," Nature, 2005, 433(7027):769-773.
Liu et al., "An oligonucleotide microchip for genome-wide microRNA profiling in human and mouse tissues," Proc. Natl. Acad. Sci., 2004, 101:9740-9744.
Meister et al., "Sequence-specific inhibition of microRNA- and siRNA-induced RNA silencing," RNA, 2004, 10:544-550.
Metzler et al., "High expression of precursor microRNA-155/BIC RNA in children with Burkitt lymphoma," Genes Chromosomes Cancer, 2004, 39:167-169.
Mossman, "Rapid colorimetric assay for cellular growth and survival: application to proliferation and cytotoxicity assays," J. Immunol. Methods, 1983, 65:55-63.
Nair et al., "Virus-encoded microRNAs: novel regulators of gene expression," Trends Microbiol.. Apr. 2006, 14(4):169-175.
Obernosterer et al., "Post-transcriptional regulation of microRNA expression," RNA, 2006, 12:1161-1167.
Parato et al., "Recent progress in the battle between oncolytic viruses and tumours," Nature Reviews, 2005, 5:965-976.
Pfeffer and Voinnet, "Viruses, microRNAs and cancer," Oncogene, Oct. 9, 2006, 25(46):6211-6219.
Pond and Manuelidis, "Oncolytic Effect of Poliomyelitis Virus on Human Epidermoid Carcinoma (Hela Tumor) Heterologously Transplanted to Guinea Pigs," Am. J. Pathol., 1964, 45:233-249.
Porter et al., "Demonstration of the specificity of poliovirus encapsidation using a novel replicon which encodes enzymatically active firefly luciferase," Virology, 1998, 243:1-11.
Portocala et al., [Action of ribonucleic acid extracted from mouse encephalomy] Studii şi cercetări de inframicrobiologie, 13:681-688, 1962.
Portocala et al., [The oncolytic effect on Ehrlich's carcinoma of ribonucleic] Revue des sciences medicates, 8:87-60, 1963.
Poy et al., "A pancreatic islet-specific microRNA regulates insulin secretion 226," Nature, 2004, 432:226-230.
Rao et al., "Myogenic factors that regulate expression of muscle-specific microRNAs," Proc. Nat'l. Acad. Sci., 2006, 103:8721-8726.
Sausville, "Genes in the service of therapeutic index: Progress for virus-directed enzyme prodrug therapy," Journal of Clinical Oncology, 2004, 22(9):1535-1537.
Schratt et al., "A brain-specific microRNA regulates dendritic spine development," Nature, 2006, 439:283-289.
Sempere et al., "Expression profiling of mammalian microRNAs uncovers a subset of brain-expressed microRNAs with possible roles in murine and human neuronal differentiation," Genome Biol., 2004, 5:R13.
Shafren et al., "Oncolysis of human ovarian cancers by echovirus type 1," Int. J. Cancer, 2005, 115(2):320-328.
Shafren et al., "Systemic Therapy of Malignant Human Melanoma Tumors by a Common Cold-Producing Enterovirus, Coxsackievirus A21," Clin Cancer Res 2004; 10: 53-60.
Shingara et al., "An optimized isolation and labeling platform for accurate microRNA expression profiling," RNA, 2005, 11:1461-1470.
Short et al., "Gene delivery to glioma cells in rat brain by grafting of a retrovirus packaging cell line," J Neuroscience Research., 27(3):427-439, Nov. 1990.
Snove et al., Expressing short hairpin RNAs in vivo, Nature Methods. Sep. 2006; 3(9): 689-695.
Sood et al., "Cell-type-specific signatures of microRNAs on target mRNA expression," Proc. Natl. Acad. Sci., 2006, 103:2746-2751.
Sun et al., "Development of a micro-array to detect human and mouse microRNAs and characterization of expression in human organs," Nucleic Acids Res., 2004, 32:e188.
Suskind et al., "Viral agents oncolytic for human tumors in heterologous host; oncolytic effect of Coxsackie B viruses," Proc. Soc. Exp. Biol. Med., 1957, 94(2):309-318.
Sutton, "Treatment of cancer by infectious nucleic acid," The Lancet, 1991, 337:1553.
Ward et al., "Plasmid DNA encoding replicating foot-and-mouth disease virus genomes induces antiviral immune responses in swine," *J Virol.*, 71(10):7442-7447, Oct. 1997.
De Palma and Naldini, "Transduction of a Gene Expression Cassette Using Advanced Generation Lentiviral Vectors," Methods Enzymol., 346:514-529, Jan. 2002.

* cited by examiner

Mouse treated intravenously
Day 8 tumor completely regressed
Day 12 hind limb paralysis
Hind limb muscle tissue, massive myositis Mouse treated intratumorally
Day 8 tumor completely regressed
Day 12 hind limb paralysis
Hind limb muscle tissue, massive myositis Control mouse
Day 12 tumor volume 0.3 $cm^3$
Normal muscle tissue adjacent to tumor A
5' NTR
VP4
VP2
VP3
VP1
2A
2B
2C
3A
3B
3C
3D
3' NTR
4x miRT
B
H1- HeLa
C
Mel 624
D
Kas 6/1
E
H1- HeLa + miRNA Mimics
Titer (log) TCID50/ml
Time (hrs)
WT
miRT
RevT
F
Viability, % Control
Mock
miRNA Control
miRNA 133
miRNA 206
miRNA 133&206
G
H
H1- HeLa
TE- 671

Figure 34

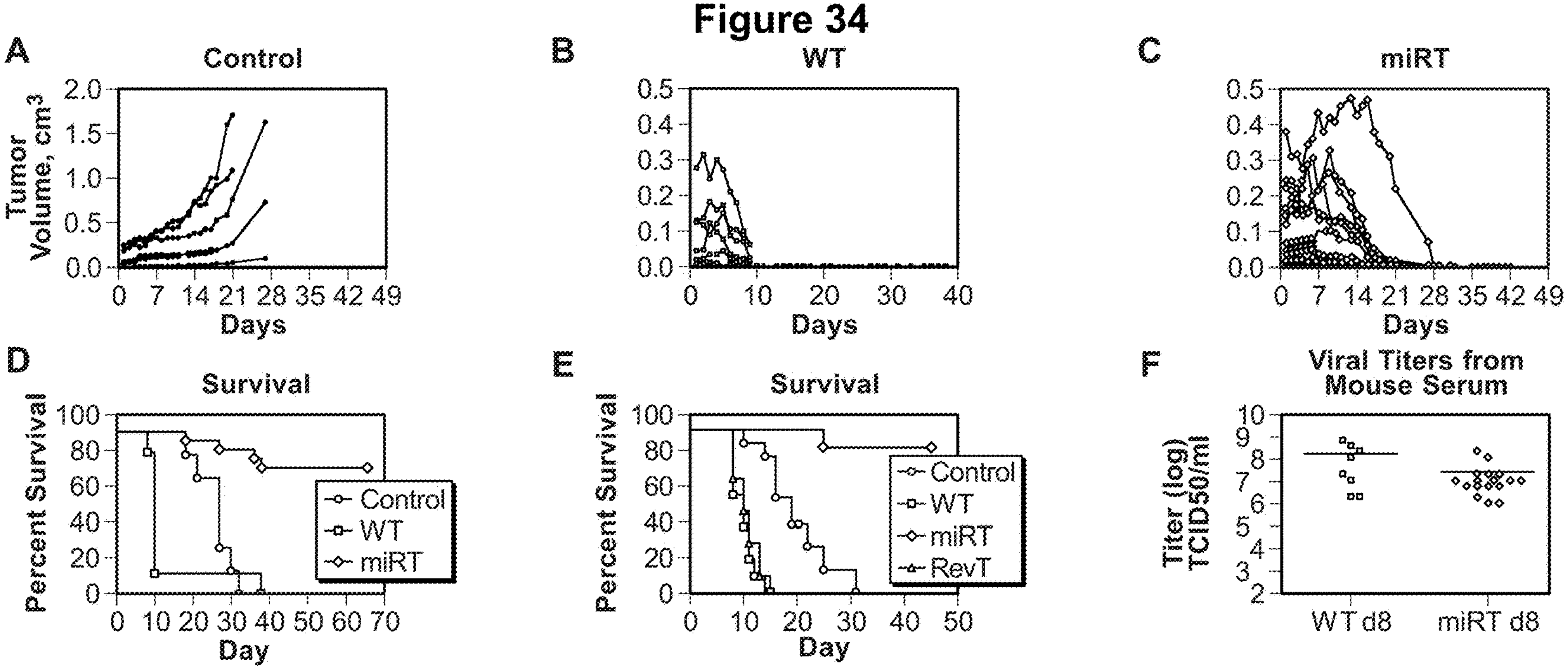

ACAGCTGGTTGAAGGGGACCAACGATACAGCTGGTTGAAGGGGACCAACTGGAGCCACACACTTCCTTACATTCCATCACCCACACACTTCCTTACATTCCA MiRT Seq. ID 82
ACAGCTGGTTGAAGGGGACCAACGATACAGCTGGTTGAAGGGGACCAACTGGAGCCACACACTTCCTTACATTCCATCACCCACACACTTCCTTACATTCCA #1 Seq. ID 83
ACTTACTTGAGACGGA**ATGATTGTGCTTATACTGGTGTAGGAACTAATTTTTCTTTATTACGTAGCATCAC**CCACACACTTCCTTACATTCCA #2 (RevT) Seq. ID 84
CCAGTGATGCCAATGAAAGAAATTCACGAATCAATCAGATGGACCAACTGCCGCCACAACCTTACTTACATTCCATCACCCACACACTTCCTTACATTCCA #3 Seq. ID 85
ACAGCTGGTTGAAGGGGACCAACGATACAGCTGGTTGAAGGGGACCAACTGGAGCCACACACTTCCTTACATTCCATCACCCACACACTTCCTTACATTCCA #4 Seq. ID 86
ACAGCTGGTCGAAGGGGACCAACGATACAGCTGGTTGAAGGGGACCAACTGGAGCCACACACTTCCTTATATTCCACCTACCTCAGTCGGATTGGATTGGG #5 Seq. ID 87
ACAGCTGGTTGAAGGGGACCAACGATACAGCTGGTTGAAGGGGACCAACTGGAGCCACACACTTCCTTACATTCCATCACCCACACACTTCCTTACATTCCA #6 Seq. ID 88
ACAGCTGGTTGAAGGGGACCAACGATACAGCTGGTTGAAGGGGACCAACTGGAGCCACACACTTCCTTACATTCCATCACACATACACTTACTTACATTCCA #7 Seq. ID 89
ACAGCTGGTTGAAGGGGACCAACGATACAGCTGGTTGAAGGGGACCAACTGGAGCCACACACTTCCTTACATTCCATCACCCACACACTTCCTTACATTCCA #8 Seq. ID 90
ACAGCTGGTTGAAGGGGACCAACGATACAGCTGGTTGAAGGGGACCAACTGGAGCCACACACTTCCTTACATTCCATCACCCACACACTTCCTTACATTCCA #9 Seq. ID 91
ACAGCTGGTCGAAGGGGACCAACGATACAGCTGGTTGAAGGGGACCAACTGGAGCCACACACTTCCTTATATTCCACCTACCACACTCGGATTGACATGGCT #10 Seq. ID 92
ACAGCTGGTTGAAGGGGACCAACGATACAGCTGGTTGAAGGGGACCAACTGGAGCCACACACTTCCTTACATTCCACCTACCTCAGTCGGATTGGATTGGGT #11 Seq. ID 93

SEQUENCE LISTING

<160> NUMBER OF SEQ ID NOS: 99

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1
ggccgcacag ctggttgaag gggaccaacg atacagctgg ttgaagggga ccaaaccggt 60

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2
acagctggtt gaaggggacc aatcacacag ctggttgaag gggaccaac 49

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
ttggtcccct tcaaccagct gtatcgttgg tccccttcaa ccagctgtgc 50

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
tcgagttggt ccccttcaac cagctgtgtg attggtcccc ttcaaccagc tgtaccggt 59

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
ggccgcccac acacttcctt acattccacg atccacacac ttccttacat tccaaccggt 60

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
ccacacactt ccttacattc catcacccac acacttcctt acattccac 49

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
tggaatgtaa ggaagtgtgt ggatcgtgga atgtaaggaa gtgtgtgggc 50

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
tcgagtggaa tgtaaggaag tgtgtgggtg atggaatgta aggaagtgtg tggaccggt 59

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
ggccgctaca tacttcttta cattccacga ttacatactt ctttacattc caaccggt 58

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
acagctggtt gaaggggacc aatcacacag ctggttgaag gggaccaac 49

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
tggaatgtaa agaagtatgt aatcgtggaa tgtaaagaag tatgtagc 48

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
tcgagttggt ccccttcaac cagctgtgtg attggtcccc ttcaaccagc tgtaccggt 59

```
<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

ggccgcacag ctggttgaag gggaccaacg atacagctgg ttgaagggga ccaaaccggt     60


<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

ccacacactt ccttacattc catcacccac acacttcctt acattccac                 49


<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

ttggtcccct tcaaccagct gtatcgttgg tccccttcaa ccagctgtgc                50


<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

tcgagtggaa tgtaaggaag tgtgtgggtg atggaatgta aggaagtgtg tggaccggt      59


<210> SEQ ID NO 17
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

ggccgctcca taaagtagga aacactacac gattccataa agtaggaaac actacaaccg     60

gt                                                                    62


<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

tccataaagt aggaaacact acatcactcc ataaagtagg aaacactaca c              51
```

```
<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

tgtagtgttt cctactttat ggaatcgtgt agtgtttcct actttatgga gc            52


<210> SEQ ID NO 20
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

tcgagtgtag tgtttcctac tttatggagt gatgtagtgt ttcctacttt atggaaccgg     60

t                                                                     61


<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21

uggaauguaa agaaguaugu a                                               21


<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22

uacaguacug ugauaacuga ag                                              22


<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23

uggaguguga caaugguguu ugu                                             23


<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24

uuaaggcacg cggugaaugc ca                                              22
```

<210> SEQ ID NO 25
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
ucccugagac ccuuuaaccu gug 23

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
ucguaccgug aguaauaaug c 21

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
ucggauccgu cugagcuugg cu 22

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 28
ucacagugaa ccggucucuu uc 22

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
cagugcaaug uuaaaagggc au 22

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30
uaacagucua cagccauggu cg 22

-continued

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 31
uugguccccu ucaaccagcu gu 22

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 32
ugugacuggu ugaccagagg g 21

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33
uauggcuuuu uauuccuaug uga 23

<210> SEQ ID NO 34
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 34
agcugguguu gugaauc 17

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35
cauaaaguag aaagcacuac 20

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
uguaguguuu ccuacuuuau gga 23

```
<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37

ugagaugaag cacuguagcu ca                                            22


<210> SEQ ID NO 38
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38

guccaguuuu cccaggaauc ccuu                                          24


<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39

ucagugcacu acagaacuuu gu                                            22


<210> SEQ ID NO 40
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40

uagcagcaca uaaugguuug ug                                            22


<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41

ucucccaacc cuuguaccag ug                                            22


<210> SEQ ID NO 42
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42

acuagacuga agcuccuuga gg                                            22
```

```
<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43

ucagugcaug acagaacuug gg                                             22


<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44

uugcauaguc acaaaaguga                                                20


<210> SEQ ID NO 45
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45

uuaaugcuaa ucgugauagg gg                                             22


<210> SEQ ID NO 46
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46

uagcagcacg uaaauauugg cg                                             22


<210> SEQ ID NO 47
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47

caaagugcuu acagugcagg uagu                                           24


<210> SEQ ID NO 48
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48

aacauucaac gcugucggug agu                                            23
```

<210> SEQ ID NO 49
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 49
uauggcacug guagaauuca cug 23

<210> SEQ ID NO 50
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 50
uaaggugcau cuagugcaga ua 22

<210> SEQ ID NO 51
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 51
uaaggugcau cuagugcagu ua 22

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52
cugaccuaug aauugacagc c 21

<210> SEQ ID NO 53
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53
uguaacagca acuccaugug ga 22

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 54
uagcagcaca gaaauauugg c 21

-continued

<210> SEQ ID NO 55
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
cccaguguuc agacuaccug uuc 23

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
ugugcaaauc uaugcaaaac uga 23

<210> SEQ ID NO 57
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
ugugcaaauc caugcaaaac uga 23

<210> SEQ ID NO 58
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
uucccuuugu cauccuaugc cu 22

<210> SEQ ID NO 59
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 59
uucccuuugu cauccuaugc cu 22

<210> SEQ ID NO 60
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 60
uggaauguaa ggaagugugu gg 22

-continued

```
<210> SEQ ID NO 61
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61

auaagacgag caaaaagcuu gu                                              22


<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62

uaacagucuc cagucacggc c                                               21


<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63

augaccuaug aauugacaga c                                               21


<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64

augaccuaug aauugacaga c                                               21


<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65

uaaucucagc uggcaacugu g                                               21


<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66

ugauugucca aacgcaauuc u                                               21
```

<210> SEQ ID NO 67
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 67
agcuacauug ucugcugggu uuc 23

<210> SEQ ID NO 68
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 68
agcuacaucu ggcuacuggg ucuc 24

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 69
ugucaguuug ucaaauaccc c 21

<210> SEQ ID NO 70
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 70
uggcucaguu cagcaggaac ag 22

<210> SEQ ID NO 71
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 71
cauugcacuu gucucggucu ga 22

<210> SEQ ID NO 72
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
uguaaacauc cuacacucag cu 22

-continued

<210> SEQ ID NO 73
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
uguaaacauc cuacacucuc agc 23

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
uauugcacau uacuaaguug c 21

<210> SEQ ID NO 75
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
uuuguucguu cggcucgcgu ga 22

<210> SEQ ID NO 76
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
uggaagacua gugauuuugu ug 22

<210> SEQ ID NO 77
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
ucuuugguua ucuagcugua uga 23

<210> SEQ ID NO 78
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 78
uucaacgggu auuuauugag ca 22

<210> SEQ ID NO 79
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
cacccguaga accgaccuug cg 22

<210> SEQ ID NO 80
<211> LENGTH: 106
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80
tccataaagt aggaaacact acacgattcc ataaagtagg aaacactaca ctggagtcca 60
taaagtagga aacactacat cactccataa agtaggaaac actaca 106

<210> SEQ ID NO 81
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
acagctggtt gaaggggacc aacgatacag ctggttgaag gggaccaact ggagacagct 60
ggttgaaggg gaccaatcac acagctggtt gaaggggacc aa 102

<210> SEQ ID NO 82
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82
ccacacactt ccttacattc cacgatccac acacttcctt acattccact ggagccacac 60
acttccttac attccatcac ccacacactt ccttacattc ca 102

<210> SEQ ID NO 83
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83
acagctggtt gaaggggacc aacgatacag ctggttgaag gggaccaact ggagccacac 60
acttccttac attccatcac ccacacactt ccttacattc ca 102

<210> SEQ ID NO 84
<211> LENGTH: 93
<212> TYPE: DNA
<213> ORGANISM: Artificial Sequence -continued
<220> FEATURE:
<223> OTHER INFORMATION: Description of Artificial Sequence: Synthetic
polynucleotide

<400> SEQUENCE: 84
acttacttga gacggaatga ttgtgcttat actggtgtag gaactaattt ttctttatta 60
cgtagcatca cccacacact tccttacatt cca 93

<210> SEQ ID NO 85
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85
ccagtgatgc caatgaaaga aattcacgaa tcaatcagat ggaccaactg ccgccacaac 60
cttacttaca ttccatcacc cacacacttc cttacattcc a 101

<210> SEQ ID NO 86
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 86
acagctggtt gaaggggacc aacgatacag ctggttgaag gggaccaact ggagccacac 60
acttccttac attccatcac ccacacactt ccttacattc ca 102

<210> SEQ ID NO 87
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87
acagctggtc gaaggggacc aacgatacag ctggttgaag gggaccaact ggagccacac 60
acttccttat attccaccta cctcagtcgg attggattgg g 101

<210> SEQ ID NO 88
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 88
acagctggtt gaaggggacc aacgatacag ctggttgaag gggaccaact ggagccacac 60
acttccttac attccatcac ccacacactt ccttacattc ca 102

<210> SEQ ID NO 89
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 89
acagctggtt gaaggggacc aacgatacag ctggttgaag gggaccaact ggagccacac 60
acttccttac attccatcac acatacactt acttacattc ca 102

<210> SEQ ID NO 90
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90
acagctggtt gaaggggacc aacgatacag ctggttgaag gggaccaact ggagccacac 60
acttccttac attccatcac ccacacactt ccttacattc ca 102

<210> SEQ ID NO 91
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 91
acagctggtt gaaggggacc aacgatacag ctggttgaag gggaccaact ggagccacac 60
acttccttac attccatcac ccacacactt ccttacattc ca 102

<210> SEQ ID NO 92
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 92
acagctggtc gaaggggacc aacgatacag ctggttgaag gggaccaact ggagccacac 60
acttccttat attccaccta ccacactcgg attgacatgg ct 102

<210> SEQ ID NO 93
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 93
acagctggtt gaaggggacc aacgatacag ctggttgaag gggaccaact ggagccacac 60
acttccttac attccaccta cctcagtcgg attggattgg gt 102

<210> SEQ ID NO 94
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 94
acagctggtt gaaggggacc aacgatacag ctggttgaag gggaccaact ggagccacac 60
acttccttac attccatcac ccacacactt ccttacattc ca 102

<210> SEQ ID NO 95
<211> LENGTH: 93
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95
acttacttga gacggaatga ttgtgcttat actggtgtag gaactaattt ttctttatta 60
cgtagcatca cccacacact tccttacatt cca 93

<210> SEQ ID NO 96
<211> LENGTH: 130
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 96 cccuccccc caggaccucc gacgugcugu gaguaugauu gcgguaccga ucugcgaaag 60
acgcacuucu gucaucaagg aguguccccu cacuaaguac caccucacag cgggguagu 120 cccccgaccg 130

<210> SEQ ID NO 97
<211> LENGTH: 89
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 97 cccuccccc caggaccucc gacgugcugu gaguaugauu gcgguaccga ucugcgaaag 60
acgcacuucu gucaucaagg agugucccc 89

<210> SEQ ID NO 98
<211> LENGTH: 700
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 98
aacgugacaa auaacacuaa uuuuuacacu acaauuauuc cgaauaccuu ugugaguuua 60
uuaacguguu augagccacc gguuagguua ucgauauacc auuguuaaac auuuaacagu 120
gguauggucg gucauacuua uauuucccuu ugggucugug gguuucauca gccaaggcgg 180
ugucugaaug cggaaugccg uuggaugagu gagccaacac ucgccaacga ggcaccaauc 240
cuaaucggcg uaaguccccg gccuccugag aacucaucga guuauccgag aaguguggaa 300
caaguguuga gcgcagggug ccguagucgg uacccauccg gggugcgucg gacccggugg 360
cagcggccac cccucagggu cugaguaguc ggauucgaug ugaccccccgu cucacagucg 420 cguugcguag cuucuaaggu uccacuauga uccgaagagc uucaugaguu cggcuauugc 480

-continued

```
cuaguuagug aaaacuggca cccaugucac auacacuaua guggccccuu ugcucacgaa    540

caagcaucuc caugaccaaa caugggacg auaacuugaa aacuauugga agauuucaau    600

gcccccuucc cuauguuuug uccgcauguu ucgauggcau uaugguguca ugaucggcgg    660

cgcacccgga gaccccagcc uuguuggggu cucgacaaaa                          700


<210> SEQ ID NO 99
<211> LENGTH: 766
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 99

aacgugacaa auaacacuaa uuuuuacacu acaauuauuc cgaauaguuu cuuugugagu     60

uuauauaacg uguuaugacc caccgguuag guuaucgaua uaccauuguu aaacauuuaa    120

cagugguauc cgucggucau acuuauauuu ccguuugcgc cugugggguuc aucagccagg    180

cggugucuga augcguaaug cuguuggaug agugacccaa cacucggcaa cgaggcacca    240

auccuaaucg gcguaagucc ccggccuaau uacgauuagc acuauccccc ggggacuuac    300

gccgauuagg auuggugccu cggcugagaa cucaucgagu uauccgagaa guguggaaca    360

aguguugucg cagggugccg uagucgguac ccauccgggg guugcgucgg acccgguggc    420

agcggccacc ccucacgggu cugaguaguc ggauucgaug ugagccccgu cucacaacuc    480

gcguugcgua gcuuguaagg uuccaguaug auccgaagag cuucaugagu ucgccuauug    540

ccuaguuagu gaaaacuggc acgcauguca gauacacuau agugggcccu uugcgucacg    600

aacaagcaug uccaugacca aacaugggga cgauaacuug aaaacuauuc gaagauuuca    660

augcgcccuu cccuauguuu uguccgcaug cauguuucca uggcauuaug gucucaugau    720

cggcggugga cgcggagacc ccacccuugu uggggucugg acaaaa                   766
```

TREATING CANCER WITH VIRAL NUCLEIC ACID

CROSS-REFERENCE TO RELATED APPLICATIONS

This application is a continuation of U.S. application Ser. No. 14/792,178 (now U.S. Pat. No. 9,957,302), filed Jul. 6, 2015, which is a continuation of U.S. application Ser. No. 13/952,343 (Abandoned), filed Jul. 26, 2013, which is a continuation of U.S. application Ser. No. 12/528,047 (Abandoned), filed Dec. 21, 2009, which is a National Stage application under 35 U.S. C. § 371 of International Application No. PCT/US2008/054459, having a filing date of Feb. 20, 2008, which claims priority to U.S. Application No. 60/902,200 filed on Feb. 20, 2007 and U.S. Application No. 61/009,968 filed on Jan. 4, 2008. The entire disclosures of these earlier applications are incorporated herein by reference.

BACKGROUND

1. Technical Field

This document relates to methods and materials involved in treating cancer with viral nucleic acid (e.g., nucleic acid coding for a picornavirus).

2. Background Information

The use of viruses to infect and kill cancer cells has been studied for many years. Typically, viruses known to infect and kill cancer cells are referred to as oncolytic viruses. The use of oncolytic viruses in this type of cancer therapy is generally different from their use in gene therapy. In gene therapy, a virus is primarily a delivery vehicle, used to deliver a corrective gene or chemotherapeutic agent to a cancer cell.

SUMMARY

This document provides methods and materials related to the use of nucleic acid coding for viruses to reduce the number of viable cancer cells within a mammal. For example, this document provides methods for using infectious nucleic acid to treat cancer, engineered viral nucleic acid, methods for making engineered viral nucleic acid, methods for identifying infectious nucleic acid for treating cancer, methods and materials for controlling virus-mediated cell lysis, and methods and materials for assessing the control of virus-mediated cell lysis.

In general, one aspect of this document features a method for treating cancer present in a mammal. The method comprises, or consists essentially of, administering, to the mammal, an effective amount of nucleic acid coding for a virus (e.g., a picornavirus) under conditions wherein cancer cells present within the mammal undergo cell lysis as a result of synthesis of virus (e.g., picornavirus) from the nucleic acid, thereby reducing the number of viable cancer cells present within the mammal. The mammal can be a human. The effective amount can be between about $3\times10^{10}$ and about $3\times10^{14}$ virus genome copies. The picornavirus can be a coxsackievirus. The cancer cells can be myeloma, melanoma, or breast cancer cells. The nucleic acid can comprise, or consist essentially of, a microRNA target element comprising at least a region of complementary to a microRNA present in non-cancer cells. A reduced number of non-cancer cells present within the mammal can undergo cell lysis as compared to the number of non-cancer cells that would undergo cell lysis when the nucleic acid lacks the microRNA target element. The microRNA can be a tissue-specific microRNA. The microRNA can be a muscle-specific, brain-specific, or heart-specific microRNA.

In another aspect, this document features an isolated nucleic acid coding for a virus and comprising a microRNA target element having at least a region that is complementary to at least a region of a microRNA present in non-cancer cells and that is heterologous to the virus. The virus can be a picornavirus. The virus can be a coxsackievirus. The virus can be a poliovirus. The microRNA can be a tissue-specific microRNA. The microRNA can be a muscle-specific, brain-specific, or heart-specific microRNA.

In another aspect, this document features an isolated nucleic acid coding for a virus and comprising a microRNA target element having at least a region that is complementary to at least a region of a cancer-specific microRNA and that is heterologous to the virus. The nucleic acid, when administered to a mammal having cancer, can be expressed in cancer cells. Expression of the nucleic acid can be restricted to cancer cells containing the cancer-specific microRNA when the nucleic acid is administered to a mammal having said cancer cells.

In another aspect, this document features a method of assessing coxsackievirus-mediated cell lysis of non-cancer cells. The method comprises, or consists essentially of:

(a) administering nucleic acid coding for a coxsackievirus to a mammal, and (b) determining whether or not the mammal develops myositis, paralysis, or death, wherein the presence of the myositis, paralysis, or death indicates that the nucleic acid causes coxsackievirus-mediated cell lysis of non-cancer cells, and wherein the absence of the myositis, paralysis, and death indicates that the nucleic acid lacks significant coxsackievirus-mediated cell lysis of non-cancer cells. The mammal can be a mouse. The nucleic acid can comprise a microRNA target element that is complementary to a microRNA present in non-cancer cells or cancer cells and that is heterologous to the coxsackievirus. The microRNA can be a tissue-specific microRNA or a cancer-specific microRNA. The microRNA can be a muscle-specific microRNA.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 34 contains three graphs plotting tumor volume at the indicated days for SCID mice, which are carrying SQ multiple myeloma xenografts, that were treated with Opti-MEM control (A), $1\times10^6$ WT CVA21 (B), and $1\times10^6$ miRT CVA21 (C); two Kaplan-Meier survival graphs of mice treated with 1 intratumoral dose of $1\times10^6$ WT CVA21 or miRT CVA21 (D), or $1\times10^6$ WT CVA21, miRT CVA21, or RevT CVA21 (E); a graph of viral titers collected from mice treated with WT or miRT CVA21 (F); and a sequence alignment of 3'NTR inserts from viruses collected from mouse #1-11 serum on day 45 (G).

DETAILED DESCRIPTION

Figure 1:
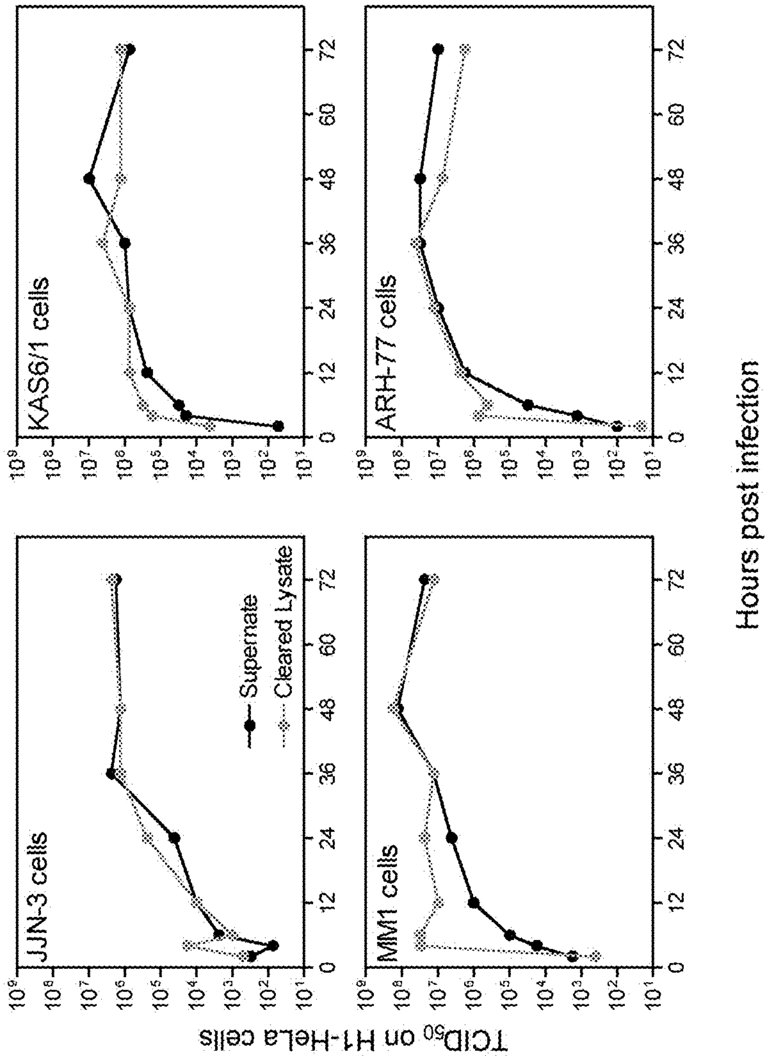
FIG. 1 contains four line graphs plotting the $TCID_{50}$ value on H1-HeLa cells for supernatant and cleared lysate samples collected from the indicated multiple myeloma cell line infected with CVA21 and cultured for the indicated time.

This document provides methods and materials related to the use of nucleic acid coding for viruses to reduce the number of viable cancer cells within a mammal. For example, this document provides methods for using viral nucleic acid to reduce the number of viable cancer cells within a mammal. Nucleic acid coding for any appropriate virus can be used to reduce the number of viable cancer cells within a mammal. In some cases, nucleic acid coding for a picornavirus can be used. A picornavirus can be an enterovirus (e.g., bovine enterovirus, human enterovirus A, human enterovirus B, human enterovirus C, human enterovirus D, human enterovirus E, poliovirus, porcine enterovirus A, and porcine enterovirus B), a rhinovirus (e.g., human rhinovirus A and human rhinovirus B), a cardiovirus (e.g., encephalomyocarditis virus and theilovirus), an apthovirus (e.g., equine rhinitis A virus and foot-and-mouth disease virus), an hepatovirus (e.g., hepatitis A virus), a parechovirus (e.g., human parechovirus and ljungan virus), an erbovirus (e.g., equine rhinitis B virus), a kobuvirus (e.g., aichi virus), or a teschovirus (e.g., porcine teschovirus 1-7 and porcine teschovirus). In some cases, nucleic acid coding for a coxsackievirus A21 (Shafren et al., *Clin. Cancer Res.*, 10(1 Pt. 1):53-60 (2004)), coxsackievirus B3 (Suskind et al., *Proc. Soc. Exp. Biol. Med.*, 94(2):309-318 (1957)), poliovirus type III (Pond and Manuelidis, *Am. J. Pathol.*, 45:233-249 (1964)), echovirus I (Shafren et al., *Int. J. Cancer,* 115(2): 320-328 (2005)), or an encephalomyocarditis virus type E (Adachi et al., *J. Neurooncol.*, 77(3):233-240 (2006)) can be used. Other viruses having nucleic acid that can be used to reduce the number of viable cancer cells can be identified using the screening methods provided in Example 1.

Other viruses having nucleic acid that can be used to reduce the number of viable cancer cells include, without limitation, Adenoviridae viruses such as mastadenoviruses (e.g., bovine adenovirus A, bovine adenovirus B, bovine adenovirus C, canine adenovirus, equine adenovirus A, equine adenovirus B, human adenovirus C, human adenovirus D, human adenovirus E, human adenovirus F, ovine adenovirus A, ovine adenovirus B, porcine adenovirus A, porcine adenovirus B, porcine adenovirus C, tree shrew adenovirus, goat adenovirus, guinea pig adenovirus, murine adenovirus B, murine adenovirus C, simian adenovirus, and squirrel adenovirus), aviadenoviruses (e.g., fowl adenovirus A, fowl adenovirus B, fowl adenovirus C, fowl adenovirus D, fowl adenovirus E, goose adenovirus, duck adenovirus B, turkey adenovirus B, pigeon adenovirus), atadenoviruses (e.g., ovine adenovirus D, duck adenovirus A, bovine adenovirus D, possum adenovirus, bearded dragon, adenovirus, bovine adenovirus E, bovine adenovirus F, cervive adenovirus, chameleon adenovirus, gecko adenovirus, snake adenovirus), siadenoviruses (e.g., frog adenovirus and turkey adenovirus A), and white sturgeon adenoviruses; Coronaviridae viruses such as coronaviruses (e.g. canine coronavirus, feline coronavirus, human coronavirus 229E, porcine epidemic diarrhea virus, transmissible gastroenteritis virus, bovine coronavirus, human coronavirus OC3, human enteric coronavirus, porcine hemagglutinating encephalomyelitis virus, puffinosis coronavirus, sars coronavirus, infectious bronchitis virus, pheasant coronavirus, turkey coronavirus, rabbit coronavirus) and toroviruses (e.g., bovine torovirus, equine torovirus, human torovirus, and porcine torovirus); Flaviviridae viruses such as flaviviruses (e.g., gadgets gulley virus, kyasanur forest disease virus, langat virus, louping ill virus, omsk hemorrhage fever virus, powassan virus, royal farm virus, tick-borne encephalitis virus, kadam virus, meadam virus, saumarez reef virus, tyuleniy virus, aroa virus, dengue virus, kedougou virus, cacipacore virus, japanese encephalitis virus, koutango virus, murray valley encephalitis virus, St. Louis encephalitis virus, usutu virus, west nile virus, yaounde virus, kokobera virus, bagaza virus, illheus virus, israel turkey meningoencephalomyelitis virus, ntaya virus, tembusu virus, zika virus, banzi virus, bouboui virus, edge hill virus, jugra virus, saboya virus, sepik virus, uganda S virus, wesselsbron virus, yellow fever virus, entebbe bat virus, yokose virus, apoi virus, cowbone ridge virus, jutiapa virus, modoc virus, sal vieja virus, san perlita virus, bukalasa bat virus, carey island virus, Dakar bat virus, Montana myotis leukoenchephalitis virus, phnom penh bat virus, rio bravo virus, cell fusing agent virus, and tamana bat virus), pestiviruses (e.g., border disease virus, bovine viral diarrhea virus 1, bovine viral diarrhea virus 2, classical swine fever virus, and pestivirus of giraffe), hepaciviruses (e.g., hepatitis C virus, GB virus B), GB virus A, and GB virus C; Hepadnaviridae viruses such as orthohepadnaviruses (e.g., hepatitis B virus, ground squirrel hepatitis B virus, woodchuck hepatitis B virus, woolly monkey hepatitis B virus, and arctic squirrel hepatitis virus) and avihepadnaviruses (e.g., duck hepatitis B virus); hepevirdae viruses such as hepeviruses (e.g., hepatitis E virus); Papillomaviridae viruses such as alphapapillomaviruses (e.g., human papillomavirus 32, human papillomavirus 10, human papillomavirus 61, human papillomavirus 2, human papillomavirus 26, human papillomavirus 53, human papillomavirus 18, human papillomavirus 7, human papillomavirus 16, human papillomavirus 6, human papillomavirus 34, human papillomavirus 54, human papillomavirus cand90, human papillomavirus 71, and rhesus monkey papillomavirus), betapapillomaviruses (e.g., human papillomavirus 5, human papillomavirus 9, human papillomavirus 49, human papillomavirus cand92, and human papillomavirus cand96), gammapapillomaviruses (e.g., human papillomavirus 4, human papillomavirus 48, human papillomavirus 50, human papillomavirus 60, and human papillomavirus 88), deltapapillomaviruses (e.g., european elk papillomavirus, deer papillomavirus, ovine papillomavirus 1, and bovine papillomavirus 1), epsilonpapillomaviruses (e.g., bovine papillomavirus 5), zetapapillomaviruses (e.g., equine papillomavirus 1), etapapillomaviruses (e.g., fringella coelebs papillomavirus), thetapapillomaviruses (e.g, psittacus erithicus timneh papillomavirus), iotapapillomaviruses (e.g., mastomys natalensis papillomavirus), kappapapillomaviruses (e.g., cottontail rabbit papillomavirus and rabbit oral papillomavirus), lambdapapillomaviruses (e.g., canine oral papillomavirus and feline papillomavirus), mupapillomaviruses (e.g., human papillomavirus 1 and human papillomavirus 63), nupapillomaviruses (e.g., human papillomavirus 41), xipapillomaviruses (e.g., bovine papillomavirus 3), omikronpapillomaviruses (e.g., phoecona spinipinnis), and pipapillomaviruses (e.g., hamster oral papillomavirus); Parvoviridae viruses such as parvoviruses (e.g., chicken parvovirus, feline panleukopenia virus, hb parvovirus, h-1 parvovirus, killham rat virus, lapine parvovirus, luiii virus, minute virus of mice, mouse parvovirus 1, porcine parvovirus, rt parvovirus, tumor virus x, hamster parvovirus, rat minute virus 1, and rat parvovirus 1), erythroviruses (e.g., human parvovirus b19, pig-tailed macaque parvovirus, rhesus macaque parvovirus, simian parvovirus, bovine parvovirus type 3, and chipmunk parvovirus), dependoviruses (e.g., aav-1, aav-2, aav-3, aav-4, aav-5, avian aav, bovine aav, canine aav, duck aav, equine aav, goose parvovirus, ovine aav, aav-7, aav-8, and bovine parvovirus 2), amdoviruses (e.g., aleutian mink disease virus), bocaviruses (e.g., bovine parvovirus and canine minute parvovirus), densoviruses (e.g., *Galleria mellonella* densovirus, *Junonia coenia* densovirus, *Diatraea saccharalis* densovirus, *Pseudoplusia includens* densovirus, and *Toxorhynchites splendens* densovirus), iteraviruses (e.g., *Bombyx mori* densovirus, *Casphalia extranea* densovirus, and *Sibine fusca* densovirus), brevidensoviruses (e.g., *Aedes aegypti* densovirus and *Aedes albopictus* densovirus), and pefudensoviruses (e.g., *Periplaneta fuliginosa* densovirus); Polyomaviridae viruses such as polyomaviruses (e.g., african green monkey polyomavirus, baboon polyomavirus 2, bk polyomavirus, bovine polyomavirus, budgerigar fledgling disease polyomavirus, hamster polyomavirus, human polyomavirus, jc polyomavirus, murine pneumotropic virus, murine pneumotropic virus, murine polyomavirus, rabbit kidney vacuolating virus, simian virus 12, and simian virus 40); Togaviridae viruses such as alphaviruses (e.g., aura virus, barmah forest virus, bebaru virus, cabassou virus, chikungunya virus, eastern equine encephalitis virus, everglades virus, fort morgan virus, getah virus, highlands j virus, mayaro virus, middelburg virus, mosso das pedras virus, mucambo virus, ndumu virus, o'nyong-nyong virus, pixuna virus, rio negro virus, ross river virus, salmon pancreas disease virus, semliki forest virus, sindbis virus, southern elephant seal virus, tonate virus, tonate virus, una virus, venezuelan equine encephalitis virus, western equine encephalitis virus, and whataroa virus), rubiviruses (e.g., rubella virus), and triniti virus; Arteriviridae viruses such as arteriviruses (e.g., equine arteritis virus, lactate dehydrogenase-elevating virus, porcine reproductive and respiratory syndrome virus, and simian hemorrhagic fever virus); Caliciviridae viruses such as vesiviruses (e.g., feline calicivirus, vesicular exanthema of swine virus, and san miguel sea lion virus), lagoviruses (e.g., european brown hare syndrome virus and rabbit hemorrhagic disease virus), noroviruses (e.g., norwalk virus), and sapoviruses (e.g., sapporo virus); Retroviruses such as mammalian type B (e.g., mouse mammary tumor virus) and type C retroviruses (e.g., murine leukemia virus), Avian type C retroviruses (e.g., avian leukocis virus), type D retroviruses (e.g., squirrel monkey retrovirus, Mason-Pfizer monkey virus, langur virus, and simian type D virus), BLV-HTLV retroviruses (e.g., bovine leukemia virus), lentiviruses (e.g., bovine, equine, feline, ovinecaprine, and primate lentiviruses), and spumaviruses (e.g., simian foamy virus); and Astroviridae viruses such as mamastroviruses (e.g., bovine astrovirus, feline astrovirus, human astrovirus, ovine astrovirus, porcine astrovirus, and mink astrovirus) and avastroviruses (e.g., chicken astrovirus, duck astrovirus, and turkey astrovirus).

Nucleic acid coding for a virus can be administered directly to cancer cells (e.g., by intratumoral administration) or can be administered systemically (e.g., by intravenous, intraperitoneal, intrapleural, or intra-arterial administration). The amount of nucleic acid administered to a mammal can range from about 10 ng to about 1 mg (e.g., from 100 ng to 500 μg, from about 250 ng to about 250 μg, from about 500 ng to about 200 μg, or from about 1 μg to about 100 μg) per kg of body weight. In some cases, from about 100 ng to about 500 μg of nucleic acid coding for a virus can be administered as a single intratumoral dose. In some cases, the amount of nucleic acid administered to a mammal can be equal to a virus genome copy number of between about $3\times10^{10}$ to about $3\times10^{14}$ genome copies (e.g., between about $3\times10^{10}$ to about $3\times10^{13}$, between about $3\times10^{10}$ to about $3\times10^{12}$, between about $3\times10^{11}$ to about $3\times10^{14}$, between about $3\times10^{10}$ to about $3\times10^{13}$, or between about $3\times10^{11}$ to about $3\times10^{12}$ genome copies). For example, nucleic acid provided herein can be administered in an amount such that about $3\times10^{11}$ virus genome copies are delivered to a mammal. In some cases, the amount of administered nucleic acid can be between about $3\times10^{10}$ to about $3\times10^{14}$ virus genome copies per kg of body weight.

Nucleic acid coding for a virus can contain sequences for either wild-type virus or for an engineered virus. For example, nucleic acid coding for a wild-type coxsackievirus A21 virus can be used to reduce the number of viable cancer cells within a mammal. In some cases, nucleic acid coding for a virus can contain nucleic acid sequences designed to control the expression of the viral polypeptides. For example, a nucleic acid provided herein can code for a virus and can contain nucleic acid encoding a polypeptide (e.g., a single chain antibody polypeptide that binds to a target cell receptor) designed to alter the virus' cell specificity at the level of virus entry. In some cases, a nucleic acid provided herein can code for a virus and can contain tissue-specific promoters to direct expression in desired cancer cells.

As described herein, nucleic acid coding for a virus can be designed to contain a microRNA target element (miRT) such that a corresponding microRNA (miRNA, specific miRNAs denoted as miR-#) present within a non-tumor cell can reduce virus gene expression, virus replication, or virus stability in that non-tumor cell. MicroRNAs are small, 21-23 nucleotide, highly conserved regulatory RNAs that can mediate translational repression or, in some cases, mRNA destruction by RISC-induced cleavage. MicroRNAs are present within many mammalian cells and can have a tissue-specific tissue distribution. As such, microRNAs can be used to modulate the tropism of a replicating virus to provide a targeting approach for any virus. The ability of nucleic acid coding for a virus to result in non-tumor cell lysis can be reduced using a microRNA target element having at least a region that is complementary to a microRNA present in the non-tumor cells. For example, coxsackievirus A21 can infect muscle cells. Thus, microRNA target elements that are complementary to microRNAs present in muscle cells can be incorporated into coxsackievirus A21 nucleic acid to reduce muscle cell lysis. Similarly, the safety of vaccines can be improved by modulating the tropism of a virus. For example, a neuronal and/or brain microRNA target element can be incorporated into the polio virus to reduce the incidence of poliomyelitis induced by the oral polio vaccine.

This same approach can be used to reduce non-tumor cell lysis by other viral nucleic acids. For example, microRNA target elements having at least a region that is complementary to the microRNAs set forth in Table 1 can be used to reduce cell lysis of the indicated tissue for the listed viruses as well as for other viruses. Other examples of microRNA target elements that can be designed to reduce viral-mediated cell lysis include, without limitation, those having at least a region complementary to a tissue-specific microRNA listed in Table 2. In some cases, nucleic acid provided herein can code for a virus and contain a microRNA target element having at least a region complementary to a classified tissue-specific microRNA. MicroRNA target elements can have complete complementarity to a microRNA. In some cases, a microRNA target element can contain mismatches in its complementarity to a microRNA provided that it contains complete complementarity to a seed sequence (e.g., base pairs 2-7) of the microRNA. See, e.g., Lim et al., *Nature,* 433(7027):769-73 (2005)).

TABLE 1

Silencing via incorporated microRNA target elements.

| Virus | Tissue | microRNA |
|---|---|---|
| Coxsackievirus A21 | Muscle | miR-1 |
| Coxsackievirus A21 | Muscle | miR-133 |
| Coxsackievirus A21 | Muscle | miR-206 |
| Coxsackievirus B3, Encephalomyocarditis-E Poliovirus III Echovirus I | Brain | miR-101 |
| Coxsackievirus B3, Encephalomyocarditis-E Poliovirus III Echovirus I | Brain | miR-124a,b |
| Coxsackievirus B3, Encephalomyocarditis-E Poliovirus III Echovirus I | Brain | miR-125 |
| Coxsackievirus B3, Encephalomyocarditis-E Poliovirus III Echovirus I | Brain | miR-128 |

TABLE 1-continued

Silencing via incorporated microRNA target elements.

| Virus | Tissue | microRNA |
|---|---|---|
| Coxsackievirus B3, Encephalomyocarditis-E Poliovirus III Echovirus I | Brain | miR-131 |
| Coxsackievirus B3, Encephalomyocarditis-E Poliovirus III Echovirus I | Brain | miR-132 |
| Coxsackievirus B3, Encephalomyocarditis-E Poliovirus III Echovirus I | Brain | miR-134 |
| Coxsackievirus B3, Encephalomyocarditis-E Poliovirus III Echovirus I | Brain | miR-135 |
| Coxsackievirus B3, Encephalomyocarditis-E Poliovirus III Echovirus I | Brain | miR-138 |
| Coxsackievirus B3, Encephalomyocarditis-E Poliovirus III Echovirus I | Brain | miR-153 |
| Coxsackievirus B3, Encephalomyocarditis-E Poliovirus III Echovirus I | Brain | miR-183 |
| Coxsackievirus B3, Encephalomyocarditis-E Poliovirus III Echovirus I | Brain | miR-1b-2 |
| Coxsackievirus B3, Encephalomyocarditis-E Poliovirus III Echovirus I | Brain | miR-219 |
| Coxsackievirus B3, Encephalomyocarditis-E Poliovirus III Echovirus I | Brain | miR-9 |
| Coxsackievirus B3, Encephalomyocarditis-E Poliovirus III Echovirus I | Brain | miR-95 |
| Coxsackievirus B3, Encephalomyocarditis-E Poliovirus III Echovirus I | Brain | miR-99b |
| Coxsackievirus B3, Echovirus I | Heart | miR-1 |
| Coxsackievirus B3, Echovirus I | Heart | miR-133 |
| Coxsackievirus B3, Echovirus I | Heart | miR-206 |
| Coxsackievirus B3, Echovirus I | Heart | miR-208 |

TABLE 2

Classified tissue-specific microRNAs.

| miRNA | Tissue | Sequence | Reference |
|---|---|---|---|
| miR-1 | Muscle | UGGAAUGUAAAGAAGUAUGUA (SEQ ID NO: 21) | Rao et al., Proc. Nat'l. Acad. Sc., 103: 8721-8726 (2006). |

TABLE 2-continued

Classified tissue-specific microRNAs.

| miRNA | Tissue | Sequence | Reference |
|---|---|---|---|
| miR-101 | Brain | UACAGUACUGUGAUAACUGAAG (SEQ ID NO: 22) | Lagos-Quintana et al., Curr. Biol., 12: 735-739 (2002). |
| miR-122a | Liver | UGGAGUGUGACAAUGGUGUUUG U (SEQ ID NO: 23) | Fu et al., FEBS Lett., 579: 3849-3854 (2005). |
| miR-124a,b | Brain | UUAAGGCACGCGGUGAAUGCCA (SEQ ID NO : 24) | Lagos-Quintana et al., Curr. Biol., 12: 735-739 (2002). |
| miR-125 | Brain | UCCCUGAGACCCUUUAACCUGUG (SEQ ID NO : 25) | Liu et al., Proc. Nat'l. Acad. Sc., 101: 9740-9744 (2004). |
| miR-126AS | Digestive | UCGUACCGUGAGUAAUAAUGC (SEQ ID NO: 26) | Shingara et al., RNA, 11: 1461-1470 (2005). |
| miR-127 | Spleen | UCGGAUCCGUCUGAGCUUGGCU (SEQ ID NO: 27) | Lagos-Quintana et al., Curr. Biol., 12: 735-739 (2002). |
| miR-128 | Brain | UCACAGUGAACCGGUCUCUUUC (SEQ ID NO: 28) | Liu et al., Proc. Nat'l. Acad. Sc., 101: 9740-9744 (2004). |
| miR-130 | Lung | CAGUGCAAUGUUAAAAGGGCAU (SEQ ID NO: 29) | Sempere et al., Genome Biol., 5: R13 (2004). |
| miR-132 | Brain | UAACAGUCUACAGCCAUGGUCG (SEQ ID NO: 30) | Lagos-Quintana et al., Curr. Biol., 12: 735-739 (2002). |
| miR-133 | Muscle | UUGGUCCCCUUCAACCAGCUGU (SEQ ID NO: 31) | Rao et al., Proc. Nat'l. Acad. Sc., 103: 8721-8726 (2006). |
| miR-134 | Brain | UGUGACUGGUUGACCAGAGGG (SEQ ID NO: 32) | Schratt et al., Nature, 439: 283-289 (2006). |
| miR-135 | Brain | UAUGGCUUUUUAUUCCUAUGUGA (SEQ ID NO: 33) | Sempere et al., Genome Biol., 5: R13 (2004). |
| miR-138 | Brain | AGCUGGUGUUGUGAAUC (SEQ ID NO: 34) | Obernosterer et al., RNA, 12: 1161-1167 (2006). |
| miR-142s 5p, 3p | Hematopoetic | CAUAAAGUAGAAAGCACUAC (SEQ ID NO: 35) UGUAGUGUUUCCUACUUUAUGGA (SEQ ID NO: 36) | Chen et al., Science, 303: 83-86 (2004). |
| miR-143 | Digestive | UGAGAUGAAGCACUGUAGCUCA (SEQ ID NO: 37) | Shingara et al., RNA, 11: 1461-1470 (2005). |
| miR-145 | Digestive | GUCCAGUUUUCCCAGGAAUCCCU U (SEQ ID NO: 38) | Shingara et al., RNA, 11: 1461-1470 (2005). |
| miR-148 | Liver, Stomach | UCAGUGCACUACAGAACUUUGU (SEQ ID NO: 39) | Shingara et al., RNA, 11: 1461-1470 (2005). |
| miR-15 (Down-regulated) | B-cell lymphocytic leukemia | UAGCAGCACAUAAUGGUUUGUG (SEQ ID NO: 40) | Calin et al., Proc. Nat'l. Acad. Sc., 99: 15524-15529 (2002). |

TABLE 2-continued

Classified tissue-specific microRNAs.

| miRNA | Tissue | Sequence | Reference |
|---|---|---|---|
| miR-150 | Spleen | UCUCCCAACCCUUGUACCAGUG (SEQ ID NO: 41) | Shingara et al., RNA, 11: 1461-1470 (2005). |
| miR-151 | Spleen | ACUAGACUGAAGCUCCUUGAGG (SEQ ID NO: 42) | Sempere et al., Genome Biol., 5: R13 (2004). |
| miR-152 | Liver | UCAGUGCAUGACAGAACUUGGG (SEQ ID NO: 43) | Sempere et al., Genome Biol., 5: R13 (2004). |
| miR-153 | Brain | UUGCAUAGUCACAAAAGUGA (SEQ ID NO: 44) | Sempere et al., Genome Biol., 5: R13 (2004). |
| miR-155 | Burkitt's Lymphoma | UUAAUGCUAAUCGUGAUAGGGG (SEQ ID NO: 45) | Metzler et al., Genes Chromosomes Cancer, 39: 167-169 (2004). |
| miR-16 (Down-regulated) | B-cell lymphocytic leukemia | UAGCAGCACGUAAAUAUUGGCG (SEQ ID NO: 46) | Calin et al., Proc. Nat'l. Acad. Sc., 99: 15524-15529 (2002). |
| miR-17-5p | Lymphoma | CAAAGUGCUUACAGUGCAGGUAGU (SEQ ID NO : 47) | He et al., Nature, 435: 828-833 (2005). |
| miR-181 | Hematopoetic | AACAUUCAACGCUGUCGGUGAGU (SEQ ID NO: 48) | Chen et al., Science, 303: 83-86 (2004). |
| miR-183 | Brain | UAUGGCACUGGUAGAAUUCACUG (SEQ ID NO: 49) | Sempere et al., Genome Biol., 5: R13 (2004). |
| miR-18a,b | Lymphoma | UAAGGUGCAUCUAGUGCAGAUA (SEQ ID NO: 50) UAAGGUGCAUCUAGUGCAGUUA (SEQ ID NO: 51) | He et al., Nature, 435: 828-833 (2005). |
| miR-192 | Kidney | CUGACCUAUGAAUUGACAGCC (SEQ ID NO: 52) | Sempere et al., Genome Biol., 5: R13 (2004). |
| miR-194 | Kidney | UGUAACAGCAACUCCAUGUGGA (SEQ ID NO: 53) | Sun et al., Nucleic Acids Res., 32: e188 (2004). |
| miR-195 | Hematopoetic | UAGCAGCACAGAAAUAUUGGC (SEQ ID NO: 54) | Baskerville et al., RNA, 11: 241-247 (2005). |
| miR-199 | Liver | CCCAGUGUUCAGACUACCUGUUC (SEQ ID NO: 55) | Sempere et al., Genome Biol., 5: R13 (2004). |
| miR-19a,b | Lymphoma | UGUGCAAAUCUAUGCAAAACUGA (SEQ ID NO: 56) UGUGCAAAUCCAUGCAAAACUGA (SEQ ID NO: 57) | He et al., Nature, 435: 828-833 (2005). |
| miR-204 | Kidney | UUCCCUUUGUCAUCCUAUGCCU (SEQ ID NO: 58) | Sun et al., Nucleic Acids Res., 32: e188 (2004). |
| miR-204 | Testis | UUCCCUUUGUCAUCCUAUGCCU (SEQ ID NO: 59) | Baskerville et al., RNA, 11: 241-247 (2005). |
| miR-206 | Muscle | UGGAAUGUAAGGAAGUGUGUGG (SEQ ID NO: 60) | Rao et al., Proc. Nat'l. Acad. Sci., 103: 8721-8726 (2006). |

TABLE 2-continued

Classified tissue-specific microRNAs.

| miRNA | Tissue | Sequence | Reference |
|---|---|---|---|
| miR-208 | Heart | AUAAGACGAGCAAAAAGCUUGU (SEQ ID NO: 61) | Sempere et al., Genome Biol., 5: R13 (2004). |
| miR-212 | Spleen | UAACAGUCUCCAGUCACGGCC (SEQ ID NO: 62) | Sempere et al., Genome Biol., 5: R13 (2004). |
| miR-215 | Liver | AUGACCUAUGAAUUGACAGAC (SEQ ID NO: 63) | Sempere et al., Genome Biol., 5: R13 (2004). |
| miR-215 | Kidney | AUGACCUAUGAAUUGACAGAC (SEQ ID NO: 64) | Sun et al., Nucleic Acids Res., 32: e188 (2004). |
| miR-216 | Pancreas | UAAUCUCAGCUGGCAACUGUG (SEQ ID NO: 65) | Sood et al., Proc. Nat'l. Acad. Sci., 103: 2746-2751 (2006). |
| miR-219 | Brain | UGAUUGUCCAAACGCAAUUCU (SEQ ID NO: 66) | Sempere et al., Genome Biol., 5: R13 (2004). |
| miR-221 | Hematopoetic | AGCUACAUUGUCUGCUGGGUUUC (SEQ ID NO: 67) | Felli et al., Proc. Nat'l. Acad. Sci., 102: 18081 18086 (2005). |
| miR-222 | Hematopoetic | AGCUACAUCUGGCUACUGGGUCU C (SEQ ID NO : 68) | Felli et al., Proc. Nat'l. Acad. Sci., 102: 18081 18086 (2005). |
| miR-223 | Hematopoetic | UGUCAGUUUGUCAAAUACCCC (SEQ ID NO: 69) | Chen et al., Science, 303: 83-86 (2004). |
| miR-24 | Lung | UGGCUCAGUUCAGCAGGAACAG (SEQ ID NO: 70) | Sempere et al., Genome Biol., 5: R13 (2004). |
| miR-25 | Lymphoma | CAUUGCACUUGUCUCGGUCUGA (SEQ ID NO: 71) | He et al., Nature, 435: 828-833 (2005). |
| miR-30b,c | Kidney | UGUAAACAUCCUACACUCAGCU (SEQ ID NO: 72) UGUAAACAUCCUACACUCUCAGC (SEQ ID NO: 73) | Sempere et al., Genome Biol., 5: R13 (2004). |
| miR-32 | Lung | UAUUGCACAUUACUAAGUUGC (SEQ ID NO: 74) | Sempere et al., Genome Biol., 5: R13 (2004). |
| miR-375 | Pancreas | UUUGUUCGUUCGGCUCGCGUGA (SEQ ID NO: 75) | Poy et al., Nature, 432: 226-230 (2004). |
| miR-7 | Pituitary | UGGAAGACUAGUGAUUUUGUUG (SEQ ID NO: 76) | He et al., Nature, 435: 828-833 (2005). |
| miR-9 | Brain | UCUUUGGUUAUCUAGCUGUAUGA (SEQ ID NO: 77) | Sun et al., Nucleic Acids Res., 32: e188 (2004). |
| miR-95 | Brain | UUCAACGGGUAUUUAUUGAGCA (SEQ ID NO: 78) | Babak et al., RNA, 10: 1813-1819 (2004). |
| miR-99b | Brain | CACCCGUAGAACCGACCUUGCG (SEQ ID NO: 79) | Liu et al., Proc. Nat'l. Acad. Sc., 101: 9740-9744 (2004). |

Figure 19:
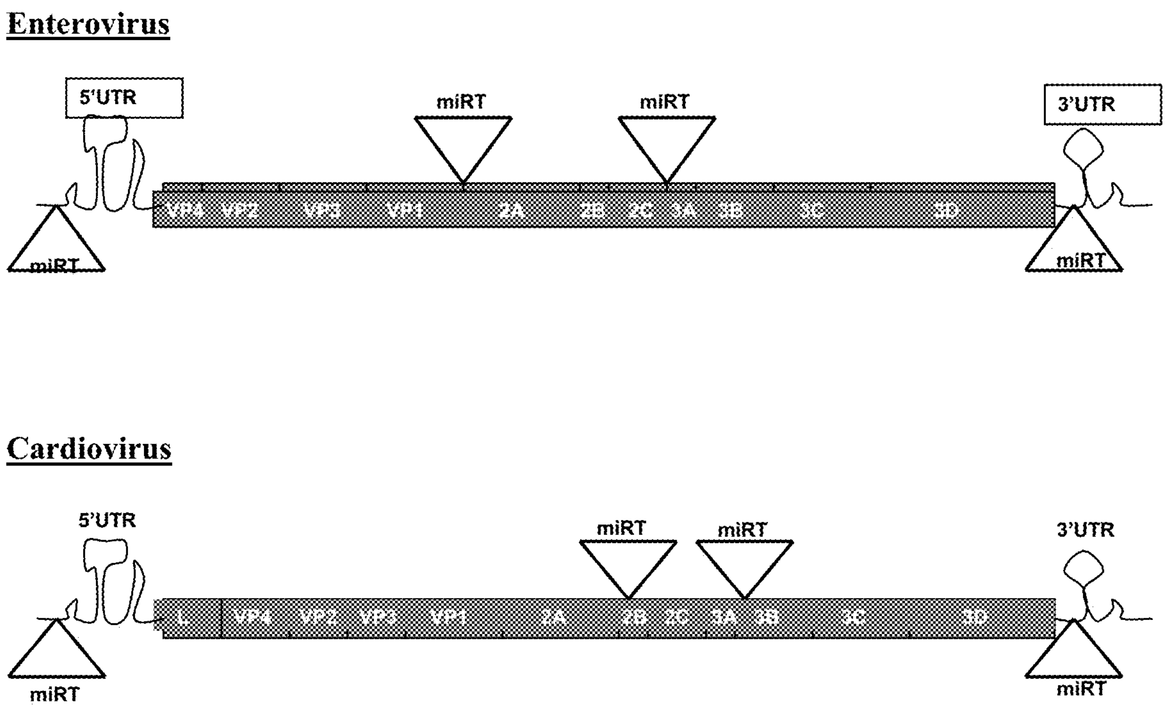
FIG. 19 contains schematic diagrams of enterovirus and cardiovirus genomes identifying examples of insertion sites for microRNA target elements.
Figure 33:
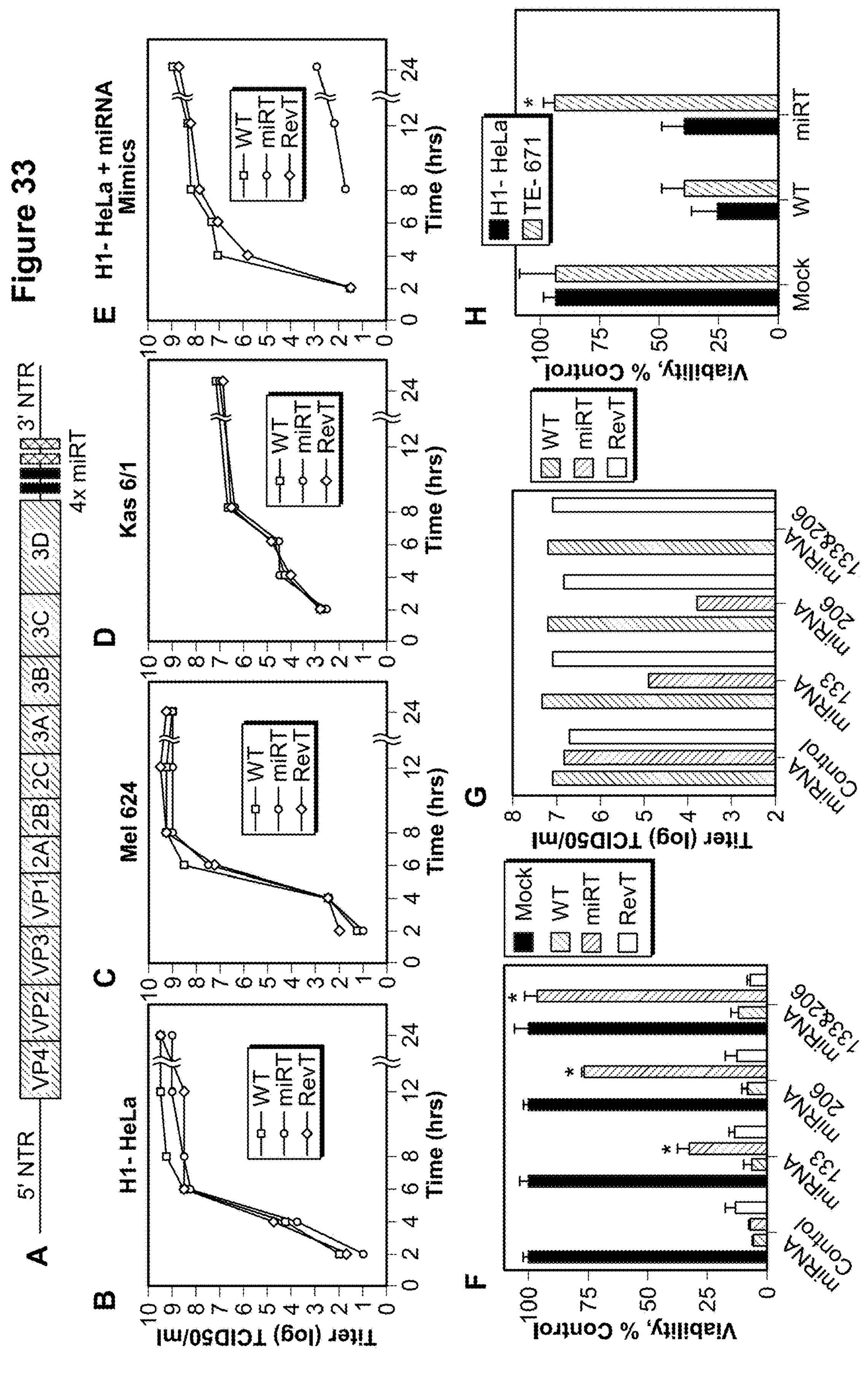
FIG. 33 contains a schematic diagram of microRNA targeted CVA21 (A); one step growth curves of WT, miRT, and RevT viruses in H1-HeLa cells (B), Mel 624 cells (C), Kas 6/1 cells (D), and H1-HeLa+miR-133 and miR-206 mimics (E); a bar graph assessing viability 24 hrs. post viral infection at MOI=1.0 with WT, miRT, or RevT CVA21 pretreated for 4 hrs. with 200 nM miRNA mimics (F), a bar graph of viral titers collected 24 hrs. post infection from supernatants of cells infected with WT, miRT, or RevT CVA21 in the presence of miRNA mimics (G), and a bar graph of in vitro survival of non muscle (H1-HeLa) or muscle (TE671) cells as determined by MTT assay when transfected with 1 μg WT or miRT CVA21 RNA in 24 well plates (H). *=p<0.01 from WT; *=<0.01 from miRNA control.

Common molecular cloning techniques can be used to insert microRNA target elements into nucleic acid coding for viruses. A nucleic acid provided herein can contain one microRNA target element or multiple microRNA target elements (e.g., two, three, four, five, six, seven, eight, nine, ten, 15, 20, 25, 30, or more microRNA target elements). For example, a viral nucleic acid can contain microRNA target elements inserted into both the 5' and 3' untranslated regions (UTR) in sections with limited secondary structure. In some cases, in the 5'UTR, microRNA target elements can be inserted upstream of the IRES. In some cases, in the 3'UTR, microRNA target elements can be inserted adjacent to the stop codon of a polypeptide or polyprotein. In some cases, microRNA target elements can be inserted in an arrangement as shown in FIG. 19 or FIG. 33A.

In some cases, microRNA target elements that are complementary to microRNAs that are ubiquitously expressed in normal cells with limited expression in tumor cells can be used to direct cell lysis to tumor cells and not non-tumor cells. For example, when using nucleic acid coding for a virus to treat B-cell lymphocytic leukemia, the viral nucleic acid can be designed to contain microRNA target elements complementary to microRNAs that are ubiquitously expressed in normal tissue while being downregulated in B-cell lymphocytic leukemia cells. Examples of such microRNAs include, without limitation, miR-15 and miR-16.

In some cases, a microRNA target element having at least a region of complementarity to a cancer-specific microRNA can be used to direct cell lysis to tumor cells. For example, nucleic acid coding for a virus can include microRNA target elements to direct microRNA-mediated targeting. Viruses such as picornaviruses (e.g., CVA21) can translate in a cap-independent way. Namely, the viral Internal Ribosome Entry Site (IRES) can recruit transcription factors and ribosomes to the viral RNA where it is then translated. In addition, a cloverleaf structure on the tip of the 5'UTR can play a role in picornavirus replication (Barton et al., *EMBO J.,* 20:1439-1448 (2001)). The following strategies are designed to conditionally distort the traditional secondary structure adopted by a virus (e.g., CVA21) in the 5'UTR in order to achieve a targeted oncolytic. These strategies are based, in part, upon RISC binding to the viral genome, but causing little, or no, miRNA-mediated cleavage. Rather, RISC in this situation has been manipulated to be a mediator of steric hindrance as the targets introduced can lack complete homology required for RNA cleavage.

Strategy: Disruption of Viral IRES

Figure 20:
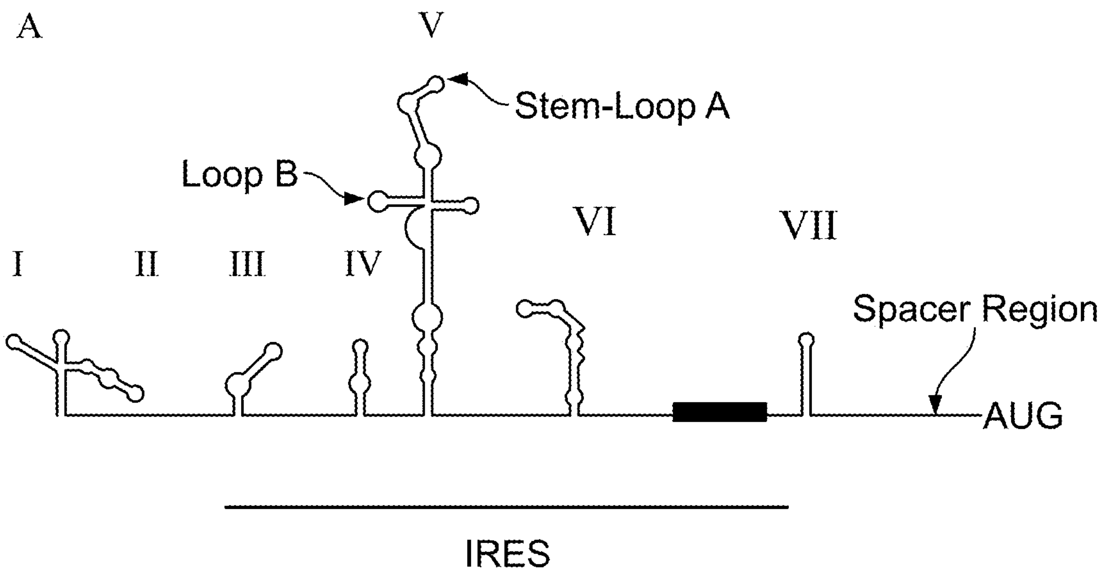
FIG. 20 is a schematic of RNA secondary structure of the 5'UTR of a picornavirus (Belsham and Sonnenberg; *Microbiological Reviews*, September 1996, p. 499-511).

By introducing binding elements of reverse complementarity to elements within the viral IRES (now called Reverse Complement “RC” region) at stem loops III, IV, and V, viral RNA can adopt a structure unlikely to recruit ribosomes (e.g., a malformed IRES), resulting in the inhibition of viral translation. Then, by introducing an adjacent region containing a microRNA target element sequence between an RC region and a stem loop of the IRES to which the RC region is targeted, RISC recruitment by the endogenous microRNA to the introduced microRNA target element can disrupt the altered (engineered) secondary structure (FIG. 20).

Wild-type secondary structure can once again be adopted in the presence of RISC, and a virus can be obtained that conditionally translates only in the presence of the microRNA whose target has been introduced into the viral genome. With oncogenic miRNAs identified, expressed exclusively (or at least in much larger numbers) in neoplastic tissues, the resulting virus can be a tumor-specific oncolytic.

Figure 21:
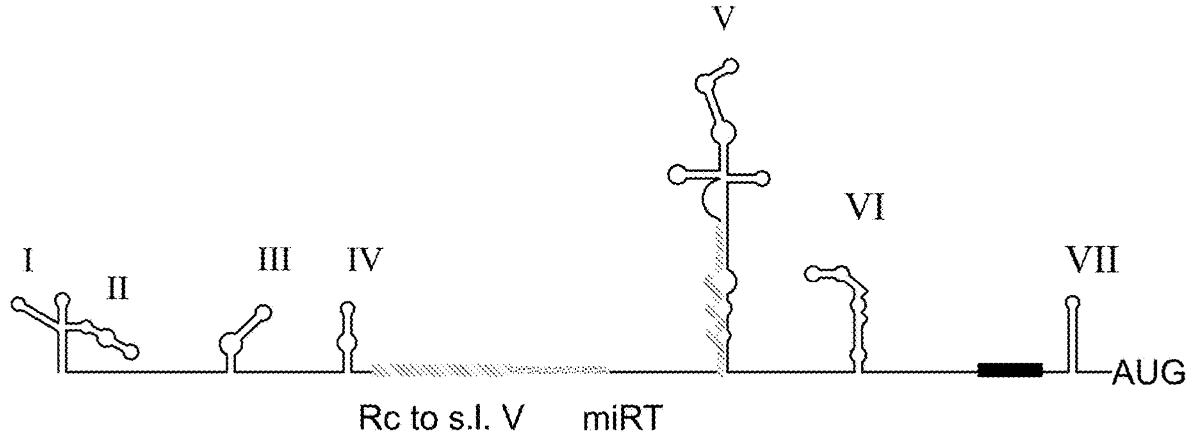
FIG. 21 is a schematic of RNA secondary structure of a virus containing a reverse complementarity region and a microRNA target element (modified from Belsham and Sonnenberg, 1996).

A reverse complement to part of stem loop V can be introduced upstream in the 5'UTR (FIG. 21). In between engineered RC region and stem loop V, a micoRNA target element (miRT) can be inserted. With reference to FIG. 21, the heavy gray line represents an engineered reverse complement, thin gray represents a microRNA target element, and the second heavy gray line corresponds to the microRNA target element that can base pair with the engineered reverse complement (note that this sequence need not be altered, rather just the cognate for introduced sequence). Since sequences can be designed such that Watson-Crick base pairing between the two heavy gray sequences is more thermodynamically favored than the wild-type situation, a new stem loop can be preferentially formed unless a factor is present to disrupt this new base pairing (i.e., RISC binding to miRT).

Figure 22:
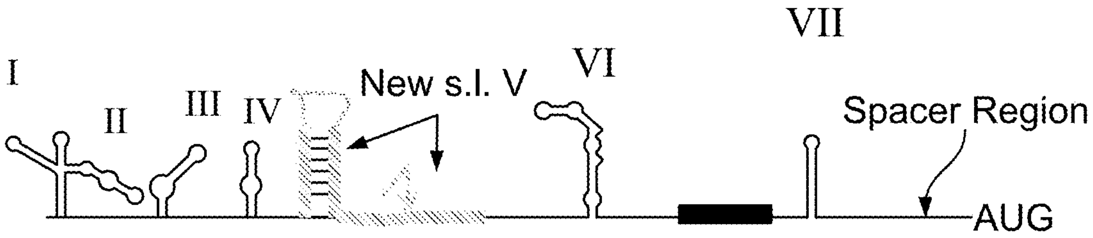
FIG. 22 is a schematic of the RNA of FIG. 21 with a 5'UTR conformation in the absence of miRNA.

In a normal cell, stem loop V can be altered due to base pairing between introduced RC region (in gray), engineered to complement previous stem loop V. MicroRNA target element is shown in light gray, not bound by RISC as the target element is coding for a microRNA absent in these cells. A new, inhibitory, loop can be formed in this situation (FIG. 22).

Figure 23:
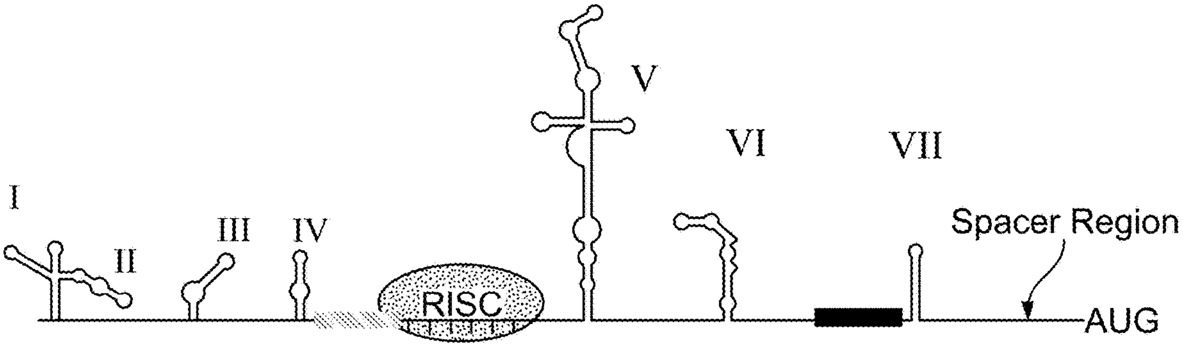
FIG. 23 is a schematic of the RNA of FIG. 21 with a 5'UTR conformation in the presence of miRNA.
Figure 24:
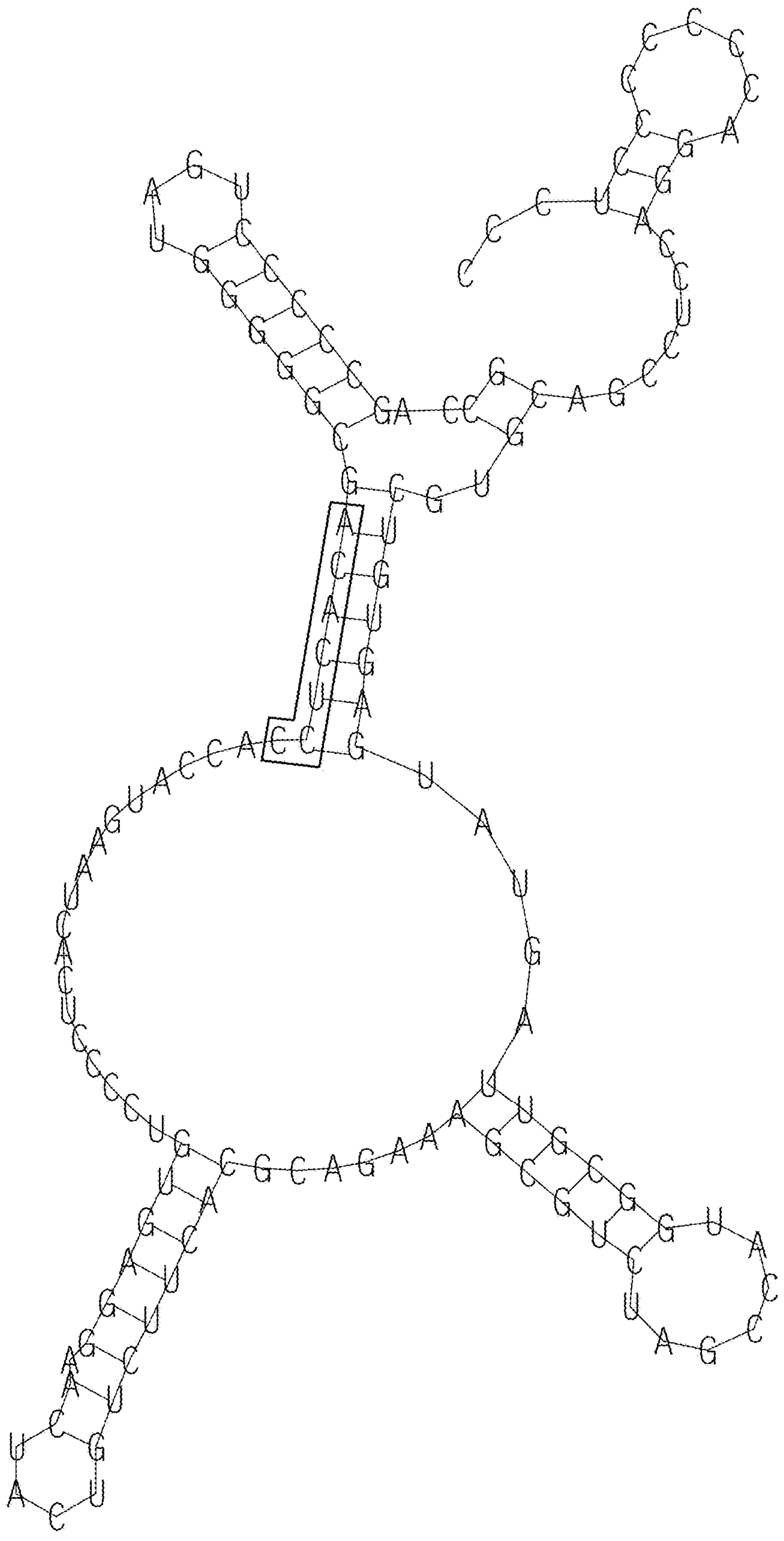
FIG. 24 is a schematic of the putative secondary structure of Hepatitis C Virus 5'UTR containing miRT. Shaded area represents seed sequence to which RISC can bind. (RNA secondary structure from Vienna RNA Structure Prediction Web Interface: http://rna.tbi.univie.ac.at/cgi-bin/RNAfold.cgi).
Figure 25:
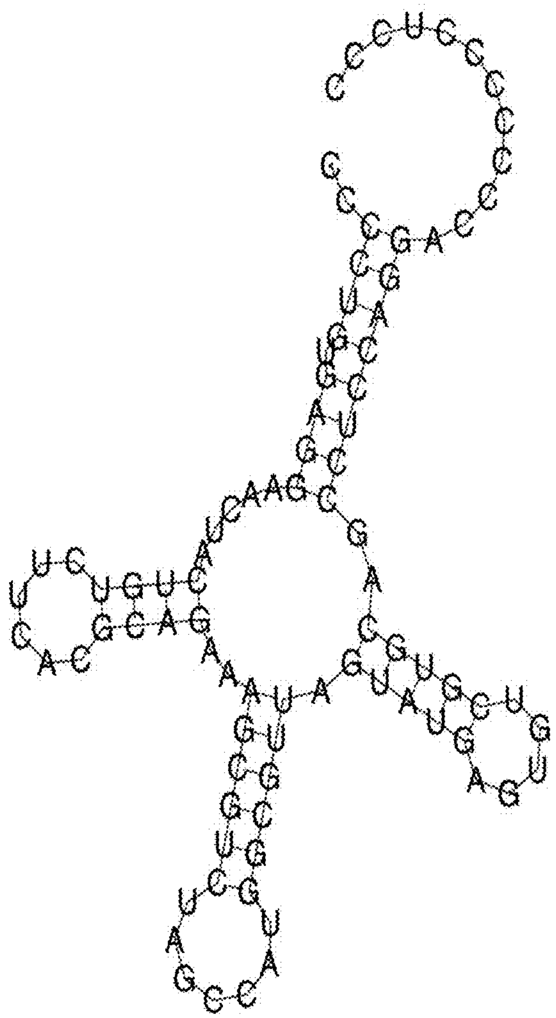
FIG. 25 is a schematic of the putative secondary structure of Hepatitis C Virus 5'UTR lacking miRT. This schematic simulates these nucleotides being unavailable for base pairing due to RISC binding.
Figure 26:
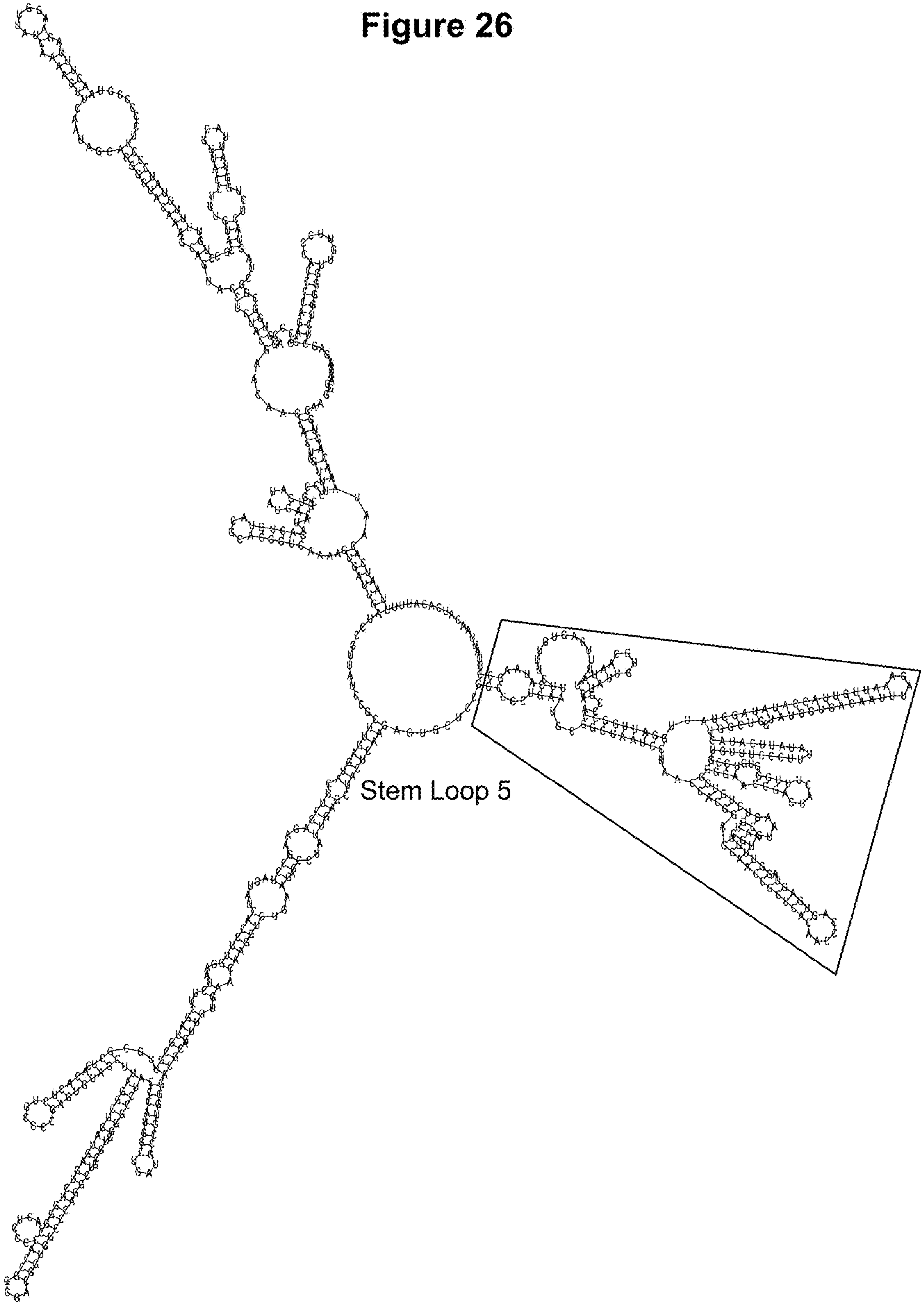
FIG. 26 is a schematic of normal secondary structure of coxsackievirus A21 5'UTR.
Figure 27:
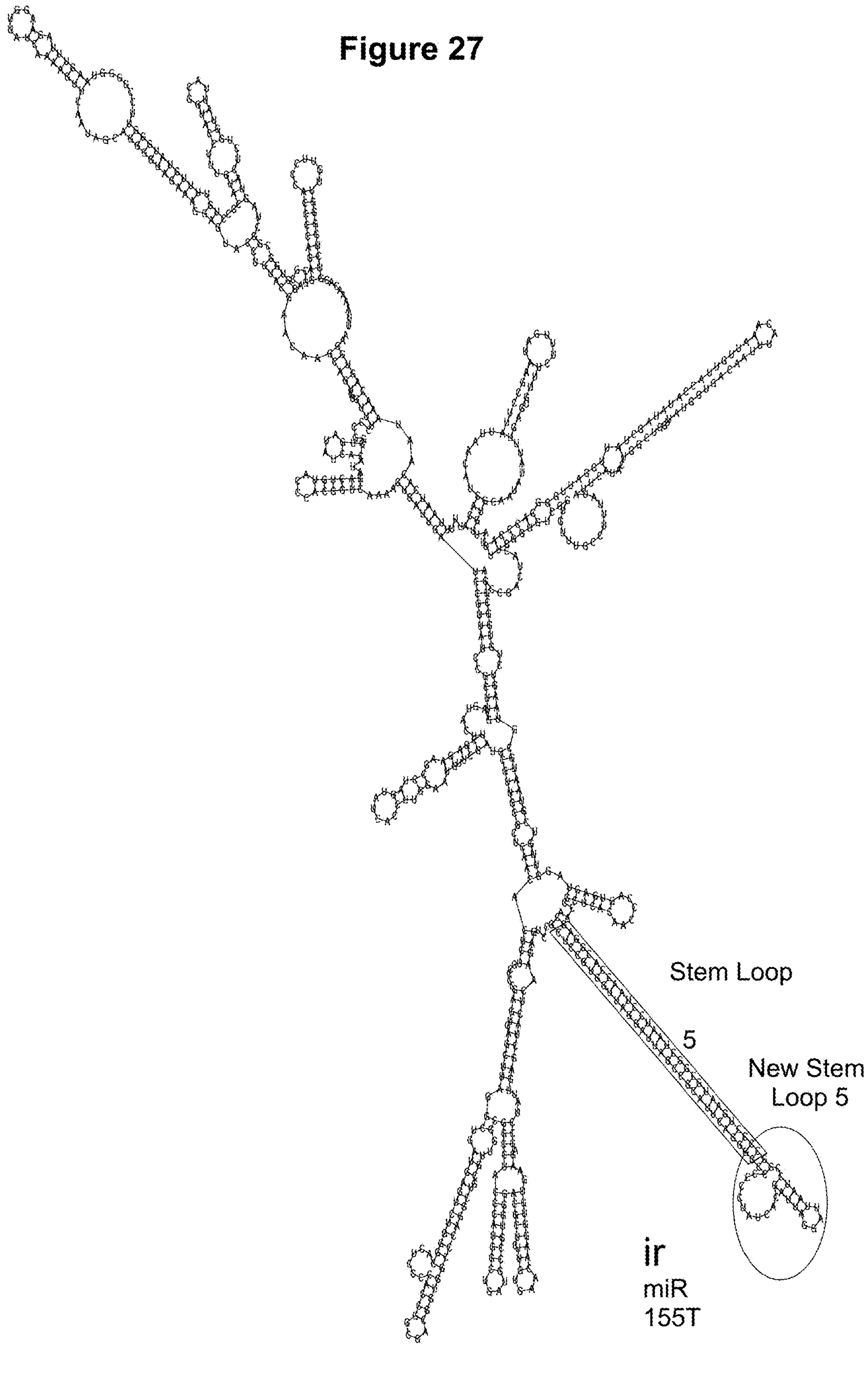
FIG. 27 is a schematic of altered secondary structure of coxsackievirus A21 5'UTR with RC region introduced against stem loop 5 and insertion of miR155T.

In a cancer cell expressing a microRNA for an engineered microRNA target element, the microRNA whose target has been engineered into the viral genome can bind RISC (FIG. 23). The association of RISC with this target can disrupt the aberrant base pairing, and the normal IRES structure can be restored. This strategy can be used to disrupt loop III, IV, or V, or any combination thereof.

To construct nucleic acids for this strategy, unique restriction sites can be introduced into a virus sequence (e.g., CVA 21 5'UTR) at locations such as (a) upstream of stem loop III, (b) between stem loops III and IV, and/or (c) between stem loops IV and V. Combinations of reverse complementary (RC) regions and microRNA target elements (miRTs) can be introduced into the new restriction sites. The RC regions can be designed against regions that are found in stem loops III, IV, or V, that are >7 bp in length, and that contain from 0-80% mismatch to determine the optimal sequence able to be disrupted by RISC binding. MicroRNA target elements for any cancer-specific microRNA (e.g., two cancer-specific microRNAs such as miR-155 and miR-21) can be introduced adjacent to reverse complementary regions. These can contain from nothing but seed sequence matches (e.g., base pairs 2-7) up to 100% homology.

Strategy: Disruption of 5' Cloverleaf Motif

This strategy involves not disrupting binding of ribosomes to the IRES, but rather disrupting the 5' cloverleaf (stem loops I, II in schematic picture) found to be a cis-acting element required for picornavirus replication. Hepatitis C Virus, a flavivirus, appears to require a target sequence for a liver-specific microRNA in the 5'UTR of the viral genome for viral accumulation in the liver (Jopling et al., *Science,* 309:1577-1581 (2005)). The binding of RISC to its target element can allow a new secondary structure to be formed that mimics the 5'cloverleaf formed in picornaviruses. The 5'UTR of Hepatitis C Virus is, in fact, more similar to picornaviruses than other flaviviruses in that it lacks a 5' cap and translates utilizing a viral IRES. Though there is little sequence homology between the Hepatitis C 5'UTR and that of the picornaviruses, secondary structure analysis reveals that masking the sequence to which RISC binds causes the formation of a cloverleaf structure comparable to that of the picornaviruses (FIGS. 24-27).

The formation of the cloverleaf found in Coxsackievirus A21 can be disrupted selectively by the inclusion of a microRNA target element in this region, along with a sequence that can be reverse complementary to elements within the cloverleaf. In the absence of RISC binding, secondary structure can be altered, while in the presence of RISC binding, it can assume wild-type base pairing.

Two different strategies can be use for the disruption of the 5' terminal cloverleaf motif:

A) Creation of Hepatitis C Virus/Coxsackievirus A21 5'UTR Chimera

Figure 28:
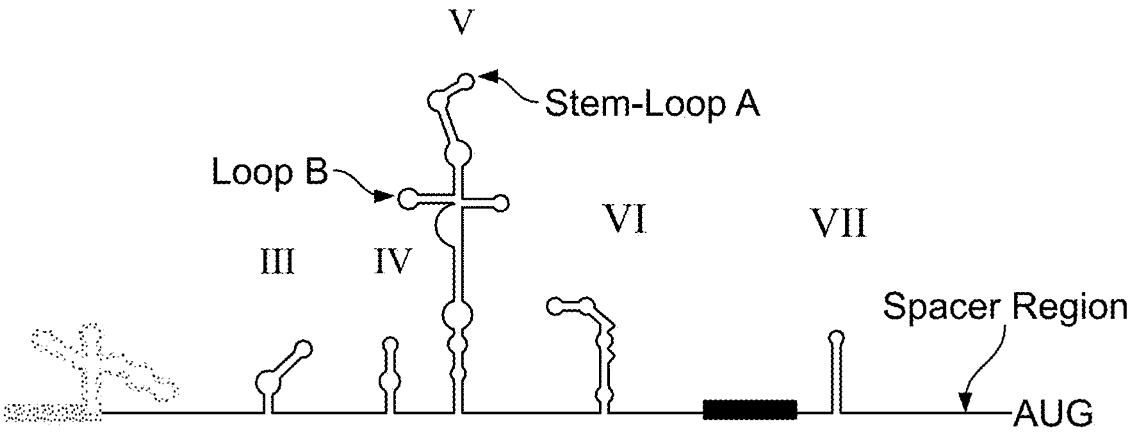
FIGS. 28-31 are schematics of RNA secondary structure.
Figure 29:
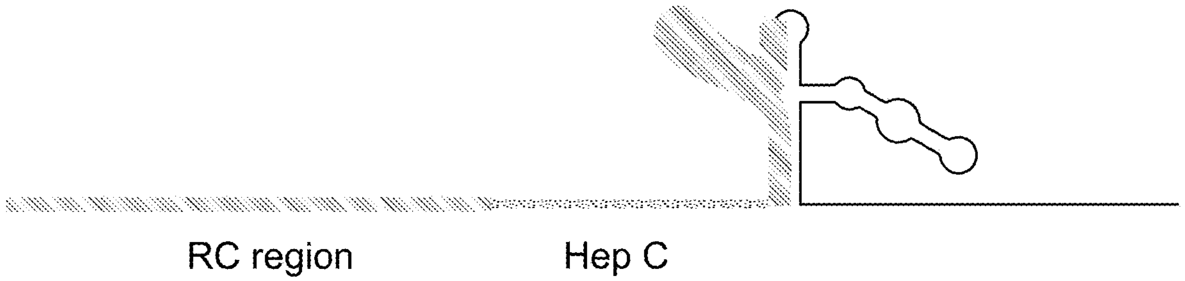

1. Overlap Extension PCR to introduce miR-155T or miR-21T in place of miR-122T found in Hep C 5'UTR 2. PCR can be used to introduce portions Hepatitis C Virus 5'UTR into Coxsackievirus A21 i) Portions of Hep C 5'UTR can be used in place of portions of CVA21 5'UTR bp (gray below represents Hepatitis C virus contribution of cloverleaf motif) (FIG. 28).

ii) Hep C region can be introduced adjacent to engineered RC region that complements portion of CVA cloverleaf motif (FIG. 29).

B) Insertion of RC Regions Up and Downstream of Cloverleaf

1. Unique restriction sites can be inserted before cloverleaf motif and/or after cloverleaf motif.

Figure 30:
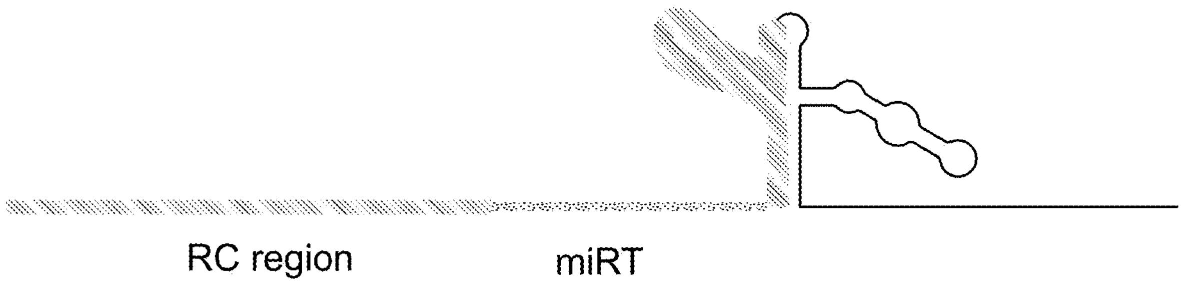
Figure 31:
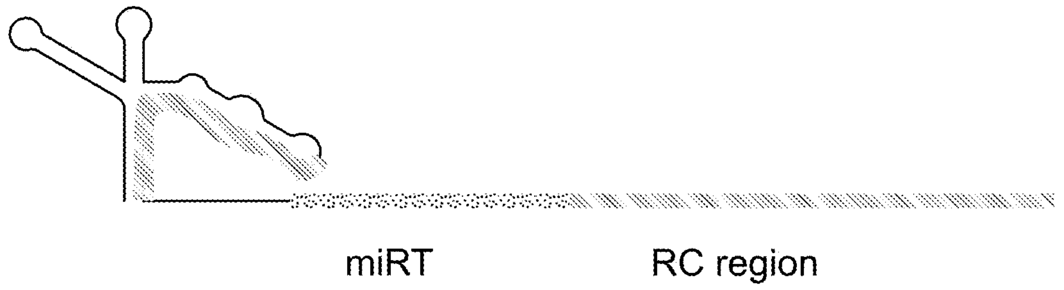

2. Disrupting Sequences (RC regions) and miRTs can be introduced into unique restriction sites.

i. in the case of insertion before cloverleaf motif, miRT can be adjacent to RC region on 3' side (FIG. 30).

ii. in the case of insertion after cloverleaf motif, miRT can be adjacent to RC region on 5' side (FIG. 31).

To construct nucleic acids for this strategy, reverse complementary (RC) regions can be designed against portions of cloverleaf motif, can be >7 base pairs in length, and can contain from 0-80% mismatch to determine the optimal sequence able to be disrupted by RISC binding. MicroRNA target elements for any cancer-specific microRNA (e.g., two cancer-specific microRNAs such as miR-155 and miR-21) and for control microRNA can be introduced adjacent to RC regions. These can contain from nothing but seed sequence matches (e.g., base pairs 2-7) up to 100% homology.

Figure 32:
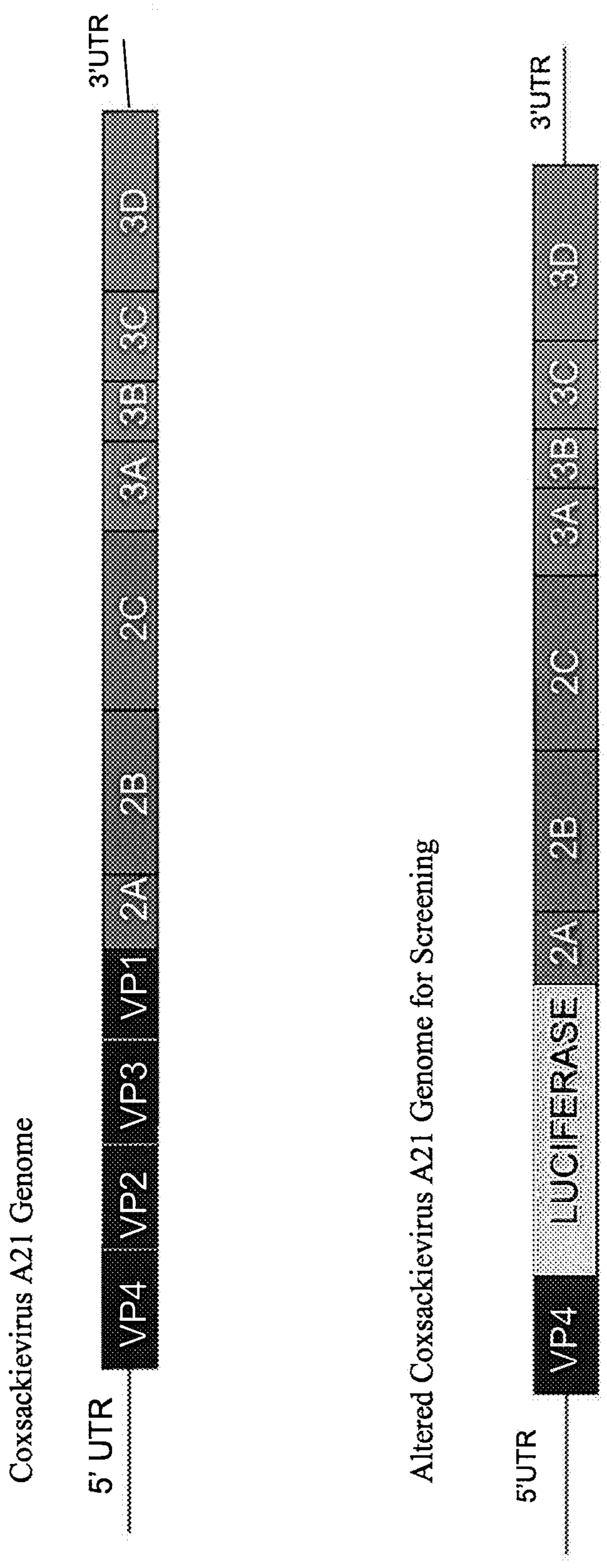
FIG. 32 is a schematic of coxsackievirus A21 genome and an altered coxsackievirus A21 genome.

Screening Strategy:

In order to screen the candidates obtained, a system can be used whereby the capsid proteins VP1, VP2, and VP3 are replaced by the luciferase gene (FIG. 32). In polioviruses, this system can retain the enzymatic activity of luciferase (Porter et al., *Virology,* 243:1-11 (1998)). In this strategy, cancer-specific miRNAs miR-155 and miR-21 can be used for screening purposes to determine possible secondary structures that cause translation in the presence and translational inhibition in absence of these miRNAs. These are not intended to be limiting, but rather, can be used as tools to screen secondary structure.

1. Construction of stable cell line expressing cancer-specific microRNA

Briefly, HeLa cells can be transduced with lentiviral vector expressing miR-155, miR-21, or control pri-miRNA sequence driven by a Pol II promoter. Endogenous cellular processing pathway by Drosha and Dicer result in expression of mature siRNAs analogous to mature microRNAs. Note that these cell lines can be engineered to express these pseudo-miRNAs and endogenous forms of these specific miRNAs are not expressed.

2. Transfection of engineered viral RNA in control & miR-155 and miR-21 expressing cells RNA can be isolated from clones from the above strategies using Ambion in vitro Maxiscript transcription kit. RNA can be transfected with Minis Trans-IT mRNA transfection kit into control and cancer-specific microRNA expressing HeLa cell lines.

3. Luciferase Assay

Luciferase assay can be performed on cell lines 1-72 hours post transfection. Positive response can be measured by a 3 fold higher production of luciferase in miR-155 or miR-21 expressing cell lines over control miRNA expressing lines.

To screen for putative tumor-specific oncolytics, the above assay can provide an artificial method of simulating the microRNA pathway. Use of lentiviral vectors to express siRNAs that mimic microRNAs, however, can express these small regulatory RNAs in higher copy number than are expressed in the cancers. The following can be a protocol to screen obtained oncolytics in the presence of microRNAs expressed in various copy numbers.

4. Testing for CPE with WT CVA21 in miR-155 and miR-21 expressing cell lines

After titration on suitable cell line, 1.0 $TCID_{50}$/cell can be added and CPE determined 48 hours post infection by MTT assay on cell lines expressing miR-155 (e.g., Raji, OVI-Ly3, L428, KMH2, L1236, and L591) and cells lines expressing miR-21 (e.g., U373, A172, LN229, U87, LN428, LN308).

CPE of >90% can correspond to a cell line that can be used in the analysis of previously identified, putative, tumor-specific oncolytics.

5. Transfection of viral RNA in identified cell line from above either containing antisense 2'O-methyl oligoribonucleotides (2'OMe) against miR-155, miR-21, or ubiquitous miRNA The addition of antisense 2'OMe-RNA can be used to inactivate specifically its cognate microRNA (Meister et al., *RNA,* 10:544-550 (2004)). Using this strategy, cell lines that specifically inactivate the activity of endogenously expressed miRNAs (in wild type copy numbers) can be obtained and used to show efficacy in this system.

6. Luciferase Assay

Luciferase assay can be performed on cell lines in the absence/presence of antisense 2'OMe-miR-155 or antisense 2'OMe-miR-21. Positive responses can be measured by a 3 fold higher production of luciferase in the absence of antisense 2'OMe-miR-155 or antisense 2'OMe-miR-21 in expressing cell lines over luciferase production in the presence of antisense 2'OMe-miR-155 or antisense 2'OMe-miR-21.

7. Insertion Sequences cloned into wild-type CVA-21

Identified insertion sequences that elicited a positive response in both lentiviral vector expression screening and using 2'O-methyl oligoribonucleotides can be cloned back into capsid-expressing Coxsackievirus A21. New microRNA target elements can be inserted in place of miR-155 or miR-21 used for screening purposes.

8. Screening via INA Screening Assay

The methods and materials provided herein can be used to screen for oncolytic activity. The obtained viruses can be propagated in the presence of miR-155, miR-21 or other inserted oncogenic microRNA target elements.

Examples of cancer-specific microRNAs include, without limitation, those listed in Table 3.

TABLE 3

Cancer-specific microRNAs.

| microRNA | Cancer |
|---|---|
| miR-25 | Lymphoma |
| miR-21 | Glioblastoma (+/− Breast Cancer) |
| miR-19a,b | Lymphoma |
| miR-18a,b | Lymphoma |
| miR-17-5p | Lymphoma |
| miR-155 | Burkitt's Lymphoma |

When assessing nucleic acid for the ability to reduce the number of viable cancer cells within a mammal, any appropriate cancer model can be used. For example, a SCID mouse model containing implanted tumor cells such as those listed in Table 4 can be used.

TABLE 4

Tumor model cell lines.

| Cancer | Tumor Type | Cell Line |
|---|---|---|
| Breast | Human Xenograft | BT-474 |
| Breast | Human Xenograft | MCF7/S |
| Breast | Human Xenograft | MCF7/TAMR-1 |
| Breast | Human Xenograft | MCF7/Mitox |
| Breast | Human Xenograft | MCF7/D40 |
| Breast | Human Xenograft | MDA-MB-231 |
| Breast | Human Xenograft | MDA-MB-435 |
| Breast | Human Xenograft | ZR-75-1 |
| Breast | Human Xenograft | ACC3199 |
| Breast | Human Xenograft | T-47D |
| Cervix | Human Xenograft | HeLa |
| Cervix | Human Xenograft | Ca Ski |
| Cervix | Human Xenograft | SiHa |
| Cervix | Human Xenograft | C-33A |
| Colon | Human Xenograft | CaCo-2 |
| Colon | Human Xenograft | HCA-7 |
| Colon | Human Xenograft | HCT 116 |
| Colon | Human Xenograft | HT-29 |
| Colon | Human Xenograft | SW480 |
| Colon | Human Xenograft | SW620 |
| Colon | Human Xenograft | DLD-1 |
| Colon | Human Xenograft | LoVo |
| Colon | Mouse Allograft | CT26.WT |
| Fibrosarcoma | Human Xenograft | HT-1080 |
| Glioblastoma | Human Xenograft | U-87 MG |
| Glioblastoma | Human Xenograft | SF 767 |
| Leukemia | Human Xenograft | HL-60, |
| Leukemia | Human Xenograft | K562/S |
| Leukemia | Human Xenograft | K562/MDR |
| Leukemia | Human Xenograft | KG-1 |
| Leukemia | Human Xenograft | OCI-AML3 |
| Leukemia | Tumor Supressor KO | NF-1 Mutant |
| Liver | Human Xenograft | SK-HEP-1 |
| Liver | Human Xenograft | HC-4 |
| Liver | Human Xenograft | HepG2 |
| Liver | Human Xenograft | Hep 3B |
| Lung | Human Xenograft | A549 |
| Lung | Human Xenograft | MV522 |
| Lung | Human Xenograft | NCI-H1299 |
| Lung | Human Xenograft | NCI-H460 |
| Lung | Human Xenograft | NCI-H1975 |
| Lung | Mouse Allograft | PC-6 |
| Lung | Mouse Allograft | LL/2 |
| Lung | Human Xenograft | NCI-H69/S |
| Lung | Human Xenograft | H69AR |
| Lung | Human Xenograft | SHP-77 |
| Lung | Human Xenograft | DMS 53 |
| Lung | Human Xenograft | DMS 153 |
| Lung | Human Xenograft | DMS 114 |
| Lymphoma | Human Xenograft | Daudi |
| Lymphoma | Human Xenograft | OCILY8 |
| Lymphoma | Human Xenograft | Raji |
| Lymphoma | Human Xenograft | Granta 519 |
| Lymphoma | Human Xenograft | Granta 4 |
| Lymphoma | Human Xenograft | KARPAS-299 |
| Lymphoma | Human Xenograft | CA46 |
| Lymphoma | Human Xenograft | U937 |
| Lymphoma | Human Xenograft | H33HJ-JA1 |
| Melanoma | Human Xenograft | A-375 |
| Melanoma | Human Xenograft | DH903 |
| Melanoma | Human Xenograft | JH1308 |
| Melanoma | Human Xenograft | KD1592 |
| Melanoma | Human Xenograft | PS1273 |
| Melanoma | Human Xenograft | WM1791C |
| Melanoma | Human Xenograft | LOX IMVI |
| Melanoma | Human Xenograft | SBL2 |
| Melanoma | Mouse Allograft | B16-F0 |
| Melanoma | Human Xenograft | SK-MEL-5 |
| Myeloma | Human Xenograft | 8226/S |

TABLE 4-continued

Tumor model cell lines.

| Cancer | Tumor Type | Cell Line |
|---|---|---|
| Myeloma | Human Xenograft | 8226/V |
| Myeloma | Human Xenograft | 8228/Dox40 |
| Myeloma | Human Xenograft | ARH-77 |
| Myeloma | Human Xenograft | ARHD60 |
| Myeloma | Human Xenograft | Kas-6/1 |
| Myeloma | Human Xenograft | KMM-1 |
| Neuroblastoma | Human Xenograft | SK-N-SH |
| Osteosarcoma | Human Xenograft | Saos-2 |
| Osteosarcoma | Human Xenograft | U-2 OS |
| Ovarian | Human Xenograft | A2780 |
| Ovarian | Human Xenograft | OVCAR-3 |
| Ovarian | Human Xenograft | SK-OV-3 |
| Ovarian | Human Xenograft | IGROV1 |
| Ovarian | Human Xenograft | OV202 |
| Pancreatic | Human Xenograft | AsPC-1 |
| Pancreatic | Human Xenograft | BxPC-3 |
| Pancreatic | Human Xenograft | CFPAC-1 |
| Pancreatic | Human Xenograft | HPAF-II |
| Pancreatic | Human Xenograft | MIA PaCa-2 |
| Pancreatic | Human Xenograft | PANC-1 |
| Pancreatic | Human Xenograft | SU.86.86 |
| Pancreatic | Human Xenograft | Capan-2 |
| Prostate | Human Xenograft | DU 145 |
| Prostate | Human Xenograft | LNCaP |
| Prostate | Human Xenograft | PC-3 |
| Renal | Human Xenograft | A-498 |
| Renal | Human Xenograft | ACHN |
| Renal | Human Xenograft | 786-O |
| Renal | Human Xenograft | Caki-1 |
| Stomach | Human Xenograft | KATO III |
| Uterine | Human Xenograft | RL 95.2 |
| Uterine | Human Xenograft | MES-SA |

The invention will be further described in the following examples, which do not limit the scope of the invention described in the claims.

EXAMPLES

Example 1—Screening for Infectious Nucleic Acid that can be Used to Treat Cancer The following screening assay is used to identify infectious nucleic acid that can be used to treat cancer. First, virus particles are obtained and assessed in vitro using a lysis assay performed with human cancer cells. Briefly, after titrating virus particles on a suitable cell line, 1.0 $TCID_{50}$/cell of virus particles is added to a panel of human cancer cell lines, and the cytopathic effect (CPE) is measured 48 hours post infection using an MTT assay as described elsewhere ((Mossman, *J. Immunol. Methods,* 65:55-63 (1983)). Viruses that exceed a CPE of >90 percent for any particular cell line are considered as putative oncolytics and proceed to in vivo screening in rodent models.

The following is performed to assess in vivo oncolytic effects. Briefly, SCID mice are inoculated with $10^6$ cancer cells (e.g., a cancer cell line listed in Table 4). When tumors reach 0.5 cm in diameter, putative oncolytic viruses are inoculated into the mice at low dose (e.g., $10^3$ $TCID_{50}$ for intratumoral injections; $10^4$ $TCID_{50}$ for intravenous injections; or $10^5$ $TCID_{50}$ for intraperitoneal injections). The tumors are measured to determine whether or not the administered virus caused a reduction in tumor size. Viruses that cause tumor reduction within two weeks are then screened by direct injection of viral nucleic acid.

To assess the direct injection of viral nucleic acid, tumors are established in SCID mice as above. Then, 1, 2, 4, 8, 16, and 32 μg of viral nucleic acid is intratumorally injected in a total volume of 100 μL of OptiMEM® (a chemically-defined medium; Invitrogen™). The titer of virus within serum is determined after seven days. A positive response is achieved when a titer of virus particles in serum is equal to or greater than $10^3$ $TCID_{50}$ and an overall reduction of tumor size that is greater than 30 percent.

Example 2—Multiple Myeloma Cells are Highly Susceptible to Coxsackievirus Infection Coxsackievirus A21 (CVA21; Kuykendall strain) was purchased from ATCC. CVA21 was propagated on H1-HeLa cells (ATCC) by plating cells at 75 percent confluence 24 hours prior to infection. Cells were infected with CVA21 at MOI 0.1 for two hours at 37° C. Unincorporated virus was removed by replacing the growth media. Infected cells were checked regularly over 48 hours for CPE. When 90 percent of cells had detached, the remaining cells were scraped from the flask, and the cell pellet was harvested. These cells were then resuspended in one to two mL of OptiMEM® (Invitrogen) and subjected to three freeze-thaw cycles. Cell debris was removed by centrifugation, and the cleared cell lysate containing virus was aliquoted and stored at −80° C.

Titration of CVA21 was performed on H1-HeLa cells. Cells were plated in 96 well plates at 50 percent confluence. After 24 hours, serial ten-fold dilutions (−2 to −10) were made of the virus; 100 μL of each dilution was added to each of eight duplicate wells. Following incubation at 37° C. for 72 hours, wells were fixed and stained (0.1% crystal violet, 20% methanol, 4% paraformaldehyde). Wells were then accessed for CPE manifest as non-staining areas devoid of viable cells. If purple staining cells were seen on 75 percent or less of the well surface, then the well was scored positive. $TCID_{50}$ values were determined using the Spearman and Karber equation.

One-step growth curves were performed using four multiple myeloma cell lines (JJN-3, KAS6/1, MM1, ARH-77). Each cell line was incubated with CVA21 at a MOI of 3.0 for 2 hours at 37° C. Following this incubation, cells were centrifuged, and unincorporated virus was removed. Cells were resuspended in fresh growth media and plated in 24 well plates with eight wells for each cell line tested. At predetermined time-points (2, 4, 6, 12, 24, 36, 48, and 72 hours), cells and growth media were harvested from one well for each cell line. Cells were separated from growth media (supernatant) with fresh growth media being added to cell pellet. Both fractions were frozen at −80° C.

At the completion of all time-points, the samples were thawed, and the cell pellets were cleared from the samples by centrifugation providing a cleared cell lysate fraction and a media supernatant fraction. The titer was determined for both fractions.

All myeloma cell lines exhibited rapid and high titer propagation of CVA21 with three of the four cell lines approaching plateau by 12 hours with titers as high as $10^7$ to $10^8$ $TCID_{50}$ per mL (FIG. 1). All titers remained steady out to the 72 hour time point. These results demonstrate that multiple myeloma cell lines are highly susceptible to CVA21 infection and rapidly propagate this virus.

Example 3—Coxsackievirus-Mediated Tumor Regression is Associated with Viremia and Myositis An in vivo study was completed in SCID mice. Mice were irradiated (150 cGy) 24 hours prior to the subcutaneous implantation of $10^7$ KAS6/1 cells into the right flank. When tumors reached an average size of 0.5 cm, mice were treated with two injections (48 hours apart) of CVA21, each $5.6\times10^5$ $TCID_{50}$. The mice were divided into three groups, Opti-MEM control (no virus), intratumoral (IT) delivery, and intravenous (IV) delivery. Tumors began regressing by day 8 at which time the mice began dragging their hind limbs. Over the next 48 hours, the mice wasted and became weak being unable to reach food or water due to progressive limb weakness. At around day 10, the mice either died or had to be euthanized. In all treated mice, the pattern was the same: tumor regression coincided with hind limb paralysis followed by wasting and euthanasia or death.

Mouse tissue was harvested and applied to a monolayer of H1-HeLa cells to check for recovery of live virus from tissues. The control mouse tissues exhibited no CPE. With virus treated mice, virus was recovered from residual tumor tissue as well as from adjacent and distant skeletal muscle tissue. Other tissues including heart, brain, liver, and spleen were negative (Table 5).

TABLE 5

CPE of mouse tissue overlays on H1-HeLa cells

| Mice | Tumor | Liver | Spleen | Brain | Muscle |
|---|---|---|---|---|---|
| IV virus #1 | +++ | − | − | − | ++ |
| IV virus #2 | +++ | − | − | − | ++ |
| IV virus #3 | +++ | − | − | − | ++ |
| IT virus #1 | +++ | − | − | − | ++ |
| No virus #1 | − | − | − | − | − |

Figure 2:
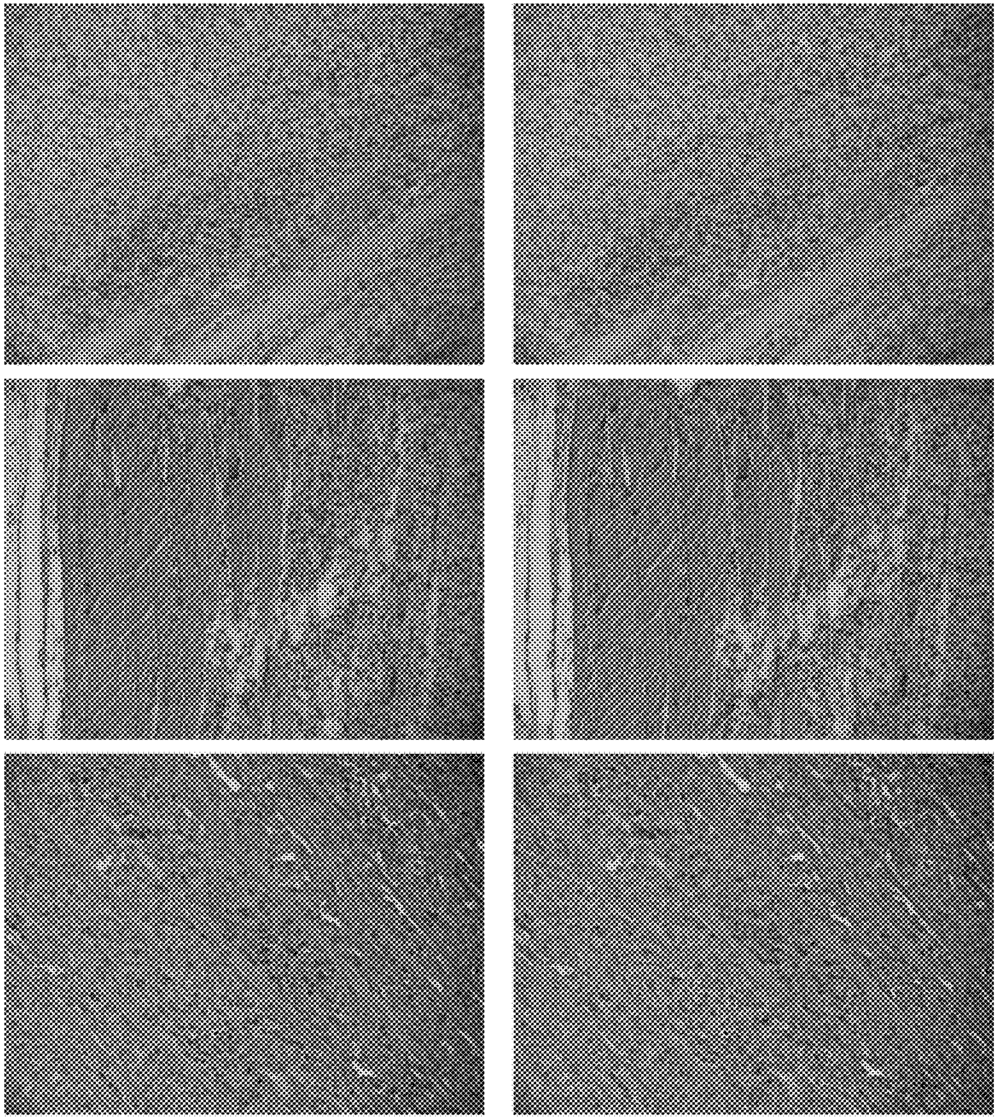
FIG. 2 contains photographs of histological analysis of hind limb muscle for treated and untreated mice.

Viral recovery was considered negative (−) if no CPE was observed by 96 hrs.
(++) denotes >50% CPE observed within 24 hrs.
(+++) denotes >50% CPE observed within 12 hrs In another in vivo study, mice were euthanized at the time point of tumor regression/hind limb paralysis, and their tissues prepared for histological examination. The pathology results indicated that virus-treated mice had significant myositis in their hind limb muscles (FIG. 2).

Figure 3:
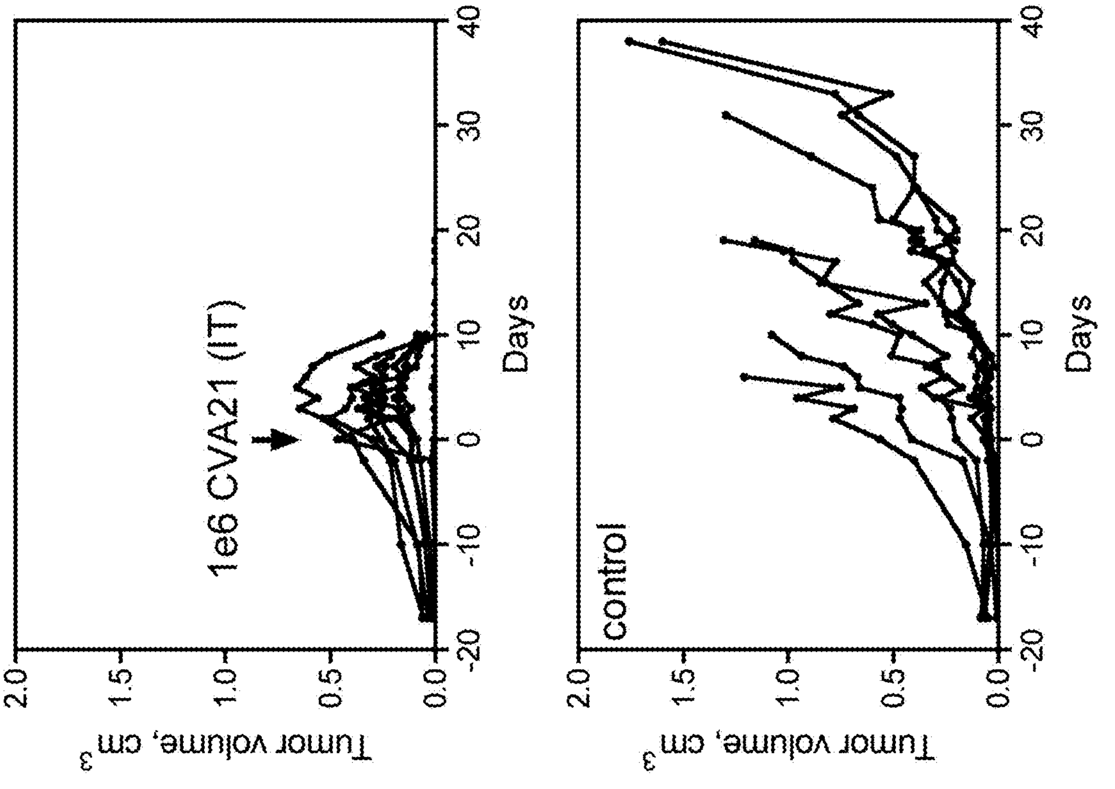
FIG. 3 contains two graphs plotting tumor volume at the indicated days for CVA21-treated (top) and untreated (bottom) mice.

The analysis of tumor volume revealed regression of all tumors treated with one intratumoral dose of CVA21 (FIG. 3). By day 7, tumors were regressing, and mice exhibited signs of hind limb paralysis associated with viremia causing myositis. All treated mice were dead by day 10, while control mice had big tumors but were otherwise healthy. Blood drawn from treated mice three and seven days post treatment exhibited titers of CVA21 that ranged from $3\times10^5$ to $3\times10^6$ per mL (Table 6).

TABLE 6

Serum titers of CVA21 in treated and control mice ($TCID_{50}$)

| | Control mice | CVA21 treated mice |
|---|---|---|
| 72 hours post treatment | 0 ± 0 | 1.08e6 ± 3.15e5 |
| 1 week post treatment | 0 ± 0 | 3.16e6 ± 0 |

As described above, the effect of CVA21 on multiple myeloma cell lines and xenografts was examined. CVA21 was propagated and titered on H1-HeLa cells. FACScan analysis was performed with human multiple myeloma cell lines (KAS6/1, MM1, JJN-3, ARH-77). All the cell lines tested were found to express surface receptors for both DAF and ICAM-1, making them viable candidates for CVA21 infection. The in vitro studies revealed that cell lines incubated with decreasing amounts of CVA21 exhibit rapid cytopathic effect in doses as low as MOI=0.0014 for three of the cell lines tested (dose for CPE with JJN-3 was MOI=0.028). With in vivo studies in SCID mice bearing human myeloma xenografts, tumors quickly and completely responded to CVA21 (both IV and IT administration). As promptly as the tumors regressed, the mice became sick with hind-limb paralysis and quickly died. Pathology reports revealed complete ablation of all tumor tissue but also signs of widespread myositis in muscle tissues. CVA21 virus was recovered from muscle biopsies but there was no evidence of CNS infection. Toxicity was observed in tumor bearing animals with a CVA21 dose as low as 560 $TCID_{50}$. In an attempt to ameliorate the myositis, adenoviruses coding for mouse IFNγ was administered prior to CVA21 therapy. Blood levels of IFNγ □ were measured by ELISA and were 1500-3000 pg/mL compared to 150 pg/mL in untreated control mice. There was little impact on tumor response or survival. These results demonstrate that CVA21 can be a potent anti-myeloma agent.

Example 4—Low Doses of Coxsackievirus Cause Tumor Regression

Four tumor bearing mice (KAS6/1 tumor cells) were treated by intratumoral injections with low dose CVA21: two mice with 5,600 $TCID_{50}$ and two mice with 560 $TCID_{50}$. By day 6, all of the treated tumors began getting soft and started regressing. Between days 7-9, all mice exhibited signs of virema with hind limb paralysis and wasting. At this point, all mice met the sacrifice criteria and were euthanized by day 12.

Example 5—Infectious RNA Encoding a Coxsackievirus Causes Tumor Regression, Viremia, and Myositis CVA21 infectious RNA was synthesized by in vitro transcription of a CVA21 plasmid DNA (obtained from Eckhard Wimmer). The CVA21 DNA was linearized by cutting with Mlu 1 restriction enzyme upstream of the T7 promoter site. This digest was terminated by ethanol precipitation. The transcription reaction was then assembled using the Ambion (Austin, Tex.) MEGAscript® kit. Briefly, the linearized DNA was mixed with reaction buffer, ribonucleotide solutions, and enzyme. Transcription was allowed to proceed at 37° C. for three hours. The sample was then treated with DNase 1 to remove the template DNA. Ambion's MEGAclear™ purification kit was used to purify the RNA for in vitro or in vivo studies. CVA21 RNA samples were quantitated by UV absorbance. The purity and size of the transcription product were assessed by formaldehyde gel electrophoresis. Activity of the CVA21 transcript was assessed by transfecting RNA into H1-HeLa cells using the Mirus (Madison, Wis.) TranIT®-mRNA Transfection Kit and monitoring cells for CPE and for release of titratable CVA21 virus.

Figure 4:
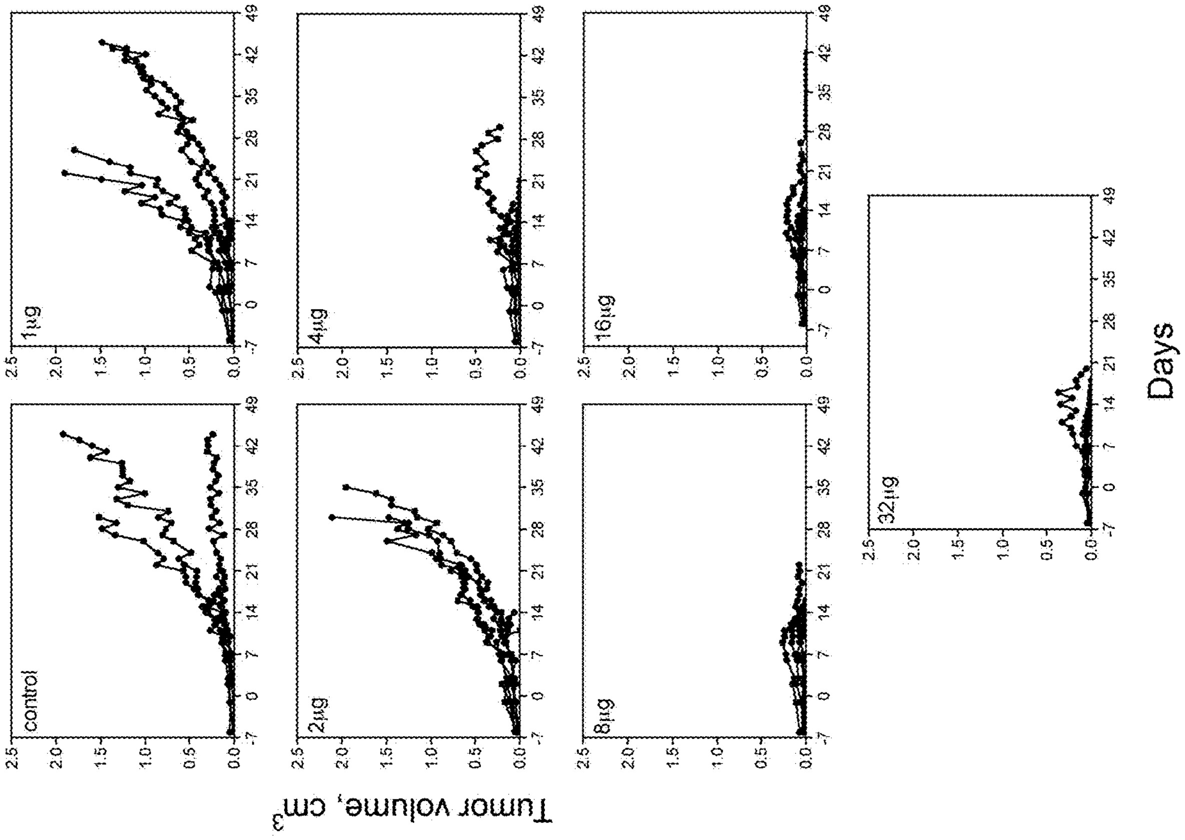
FIG. 4 contains graphs plotting tumor volume at the indicated days for mice treated intratumorally with the indicated amount of infectious RNA encoding a coxsackievirus.

To test the effectiveness of CVA21 infectious RNA to cause the same tumor destruction as CVA21 virus, SCID mice bearing KAS6/1 subcutaneous xenografts were given intratumoral injections of CVA21 RNA at increasing doses (0, 1 μg, 2 μg, 4 μg, 8 μg, 16 μg, and 32 μg). Tumors were measured daily, and mice were monitored for signs of hind limb paralysis. Blood was also drawn from mice at days 3, 7, 10, 14, 17, and 21 to monitor serum titers of CVA21 virus. All mice in the groups that received 4 μg or more of RNA had tumor regression, viremia, and myositis causing hind limb paralysis and death (Table 7 and FIG. 4). Two mice in each of the 1 μg and 2 μg groups exhibited tumor regression and hind limb paralysis, but tumors progressed in the other mice in those groups as well as in non-treated mice. These non-responding animals did not exhibit signs of myositis and were euthanized when their tumors were greater than 10 percent of body weight.

TABLE 7

Mean virus titers in mouse serum/group ($TCID_{50}$).

| RNA (μg) | 3 day | 7 day | 10 day | 14 day | 17 day | 21 day |
|---|---|---|---|---|---|---|
| 0 | 0 | 0 | 0 | 0 | 0 | 0 |
| 1 | 5e2 | 6e4 | 1e5 | 6e4 | 0 | 0** |
| 2 | 5e2 | 0 | 1e6 | 6e4 | 8e4 | 8e4 |
| 4 | 1e6 | 1e6 | 6e6 | 1e6 | 7e5 | 3e5** |
| 8 | 2e6 | 7e4 | 7e4 | 1e6 | 3e4** | 3e4** |
| 16 | 2e4 | 6e5 | 8e5 | 3e5** | 3e4** | 0** |
| 32 | 6e4 | 2e5 | 1e6 | 1e5 | 3e6** | |

**Denotes more than 50% of mice dead in group

Figure 5:
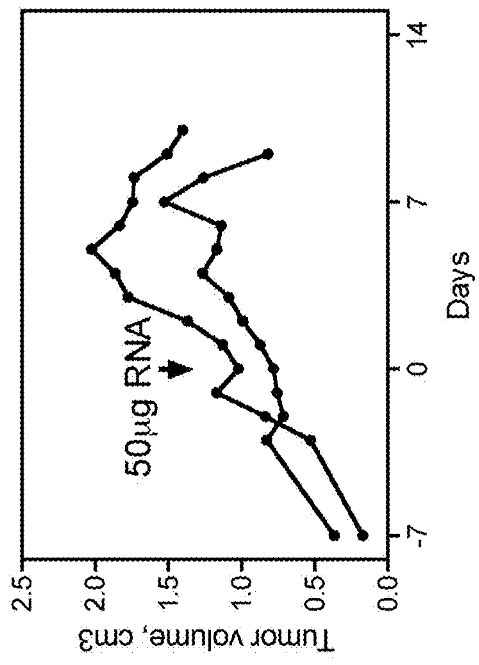
FIG. 5 is a graph plotting tumor volume at the indicated days for mice treated intravenously with 50 μg of infectious RNA encoding a coxsackievirus.

In another study, two mice bearing myeloma xenografts were tested to determine whether CVA21 infectious RNA given intravenously initiates the oncolytic intratumoral CVA21 infection. Two SCID mice bearing KAS6/1 subcutaneous xenografts were each given an intravenous tail vein injection of a solution containing 50 μg CVA21 RNA. By day 4 post injection of the RNA, both mice had measurable viral titers in their serum ($TCID_{50}=3\times10^5$ per mL). In addition, tumor regression began around day 7 with hind limb paralysis at day 9 followed by death at day 10 with serum virus titers at $3\times10^6$ $TCID_{50}$ (Table 8 and FIG. 5).

TABLE 8

Progression of infection in mice treated intravenously with infectious viral RNA.

| | Day 4 serum $TCID_{50}$ | Tumor regression | Hind limb paralysis | Death (Serum $TCID_{50}$) |
|---|---|---|---|---|
| Mouse 1 | 3e5 | Day 8 | Day 10 | Day 11 |
| Mouse 2 | 3e5 | Day 6 | Day 10 | Day 11 (3e6) |

Example 6—microRNA-Dependent Silencing in Muscle

A microRNA-dependent technique for controlling viral gene expression was developed to control effects associated with viral expression in non-tumor cells (e.g., myositis associated with CVA21 therapy). Coxsackievirus A21, a picornavirus with a 7.4 kb genome, is not well suited for the incorporation of trackable transgenes. Therefore, to test the ability of microRNA target elements to confer tissue-specific silencing of a virus in vitro, GFP-tagged plasmids and lentiviral vectors expressing GFP were generated. Three highly conserved, muscle-specific microRNAs (miR-1, miR-133, and miR-206) were selected as potential modulators of gene expression, and target elements complementary to these microRNA sequences were incorporated into the 3'UTR of GFP. Immunofluorescence and flow-cytometric analysis revealed microRNA target element-dependent suppression of gene expression in the muscle cells, while controls with hematopoetic cell-specific microRNA target elements remained unaffected. Induction of higher levels of miR-1, miR-133, and miR-206 in muscle cells amplified this effect. These results demonstrate that the incorporation of microRNA target elements into the viral genome provides an effective approach by which tissue tropism of oncolytic viruses can be altered.

Materials and Methods

Cell Culture, Transfections, and Lentiviral Vector Production.

HeLa, L6, TE-671, C2C12, 293T, and 3T3 cells were obtained from American Type Culture Collection and were maintained in DMEM supplemented with 10% FBS (also referred to as Growth Medium) in 5% $CO_2$. Cells were differentiated in DMEM supplemented with 2% horse serum for four days. Transfections were performed using the Promega (Madison, Wis.) Calcium Phosphate ProFection mammalian Transfection System with a total of 3 μg of DNA per well in a six-well plate. Briefly, cells were transfected at 24 hours after being plated in 2 mL of medium at $0.25\times10^6$ cells/well. Cells were harvested or used for immunofluorescence 72 hours after transfection. Lentiviral vectors were obtained by transfection of 10 μg of each lentiviral transfer plasmid (pHR-sin-CSGW dlNot1 or pHR-sin-F.Luc) provided by Y. Ikeda and lentiviral packaging plasmid (CMV ΔR8.91), and 3 μg VSV-G packaging construct pMD.G in a T75 flask. Supernatant was harvested at 72 hours post transfection, and filtered through a 0.45 micron syringe filter.

Plasmid Construction.

microRNA sequences were obtained from the Sanger Institute miRBase database (internet site "microrna.sanger-.ac.uk/sequences/"). Oligos were annealed in equimolar amounts in STE Buffer by heating to 94° C. followed by gradual cooling at bench top. Oligos were designed using methods described elsewhere (Brown et al., *Nat. Med.,* 12:585-591 (2006)). The following oligos were used for annealing. The underlined sequences represent microRNA target elements. The annealed oligos were cloned into XhoI/NotI site of pHR-sin-CSGW dlNot1, and lentiviral vectors were produced.

Figure 6:
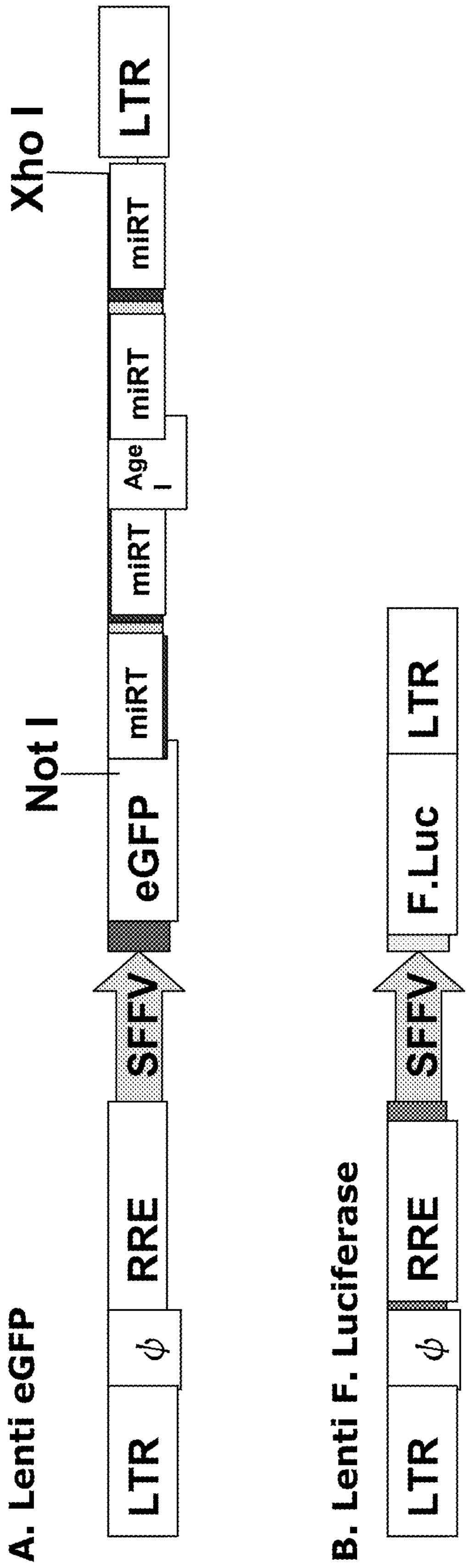
FIG. 6 contains schematic diagrams of lentiviral transfer plasmids encoding (A) eGFP tagged with four tandem copies of control or muscle-specific microRNA target elements or (B) firefly luciferase.
Figure 7:
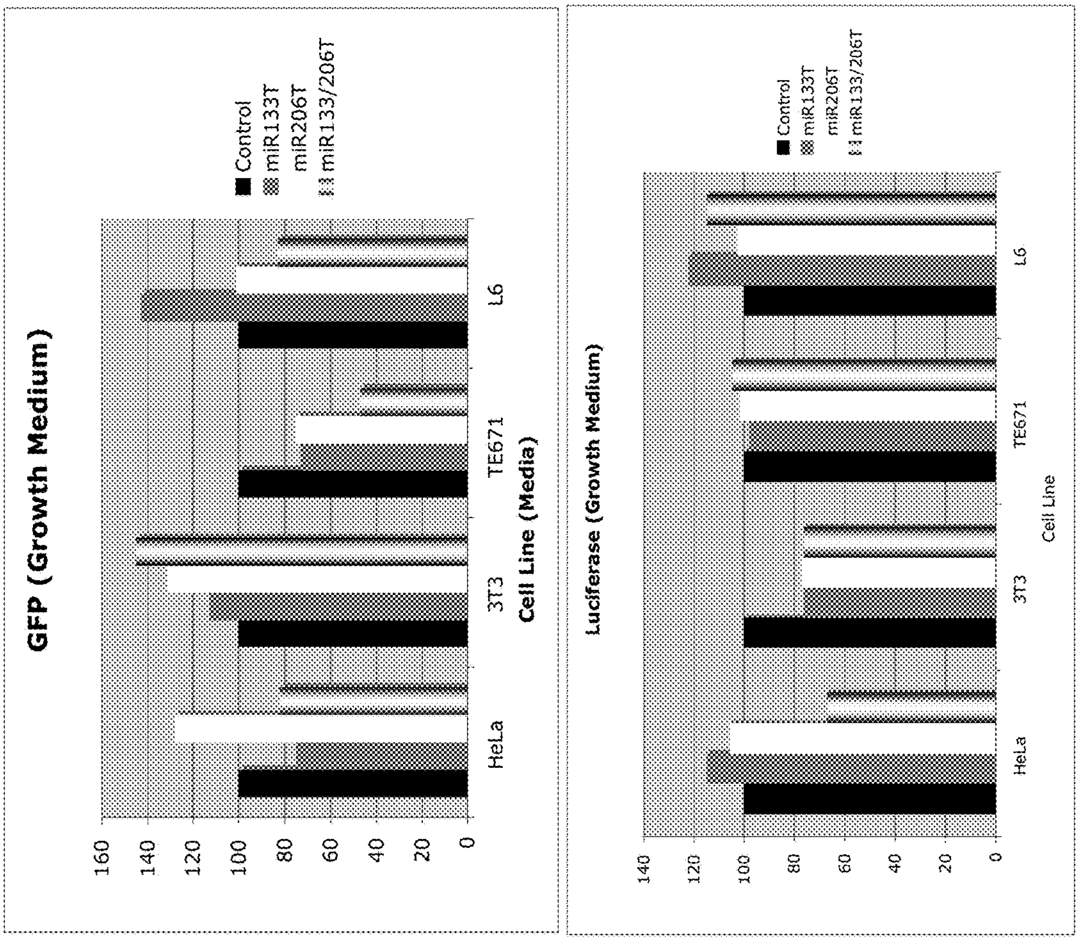
FIG. 7 contains bar graphs plotting GFP (top) and luciferase (bottom) activity for non-muscle (HeLa, 3T3) and muscle (TE671, L6) cells transduced with eGFP-encoding lentiviral vectors tagged with control microRNA target elements (miR142-3p) or muscle-specific microRNA target elements (miR133, miR-206, miR133/206) microRNA targets and non-tagged luciferase vectors. Top: Cells were grown in DMEM plus 10 percent FBS and harvested at 72 hours for flow analysis. Bottom: Cells were grown in DMEM plus 10 percent FBS and harvested at 72 hours for luciferase assay.

Briefly, four tandem copies of target elements for miR-133 and miR206 were incorporated into the 3'UTR of the lentiviral vector. A hematopoetic cell-specific microRNA target element for miR142-3P was incorporated in the same fashion and used as a control. Two further constructs were generated incorporating two tandem copies of two muscle-specific microRNA target elements (miR1 and miR-133 to form construct miR1/133T, and miR133 and 206 to form miR133/206T; FIG. 6A).

miR133
Sense #1:
(SEQ ID NO: 1)
5'-GGCCGCACAGCTGGTTGAAGGGGACCAACGATACAGCTGGTTGAAGG-
GGACCAAACCGGT-3'

Sense #2:
(SEQ ID NO: 2)
5'-ACAGCTGGTTGAAGGGGACCAATCACACAGCTGGTTGAAGGGGACCAAC-
3'

Anti-sense #1:
(SEQ ID NO: 3)
5'-TTGGTCCCCTTCAACCAGCTGTATCGTTGGTCCCCTTCAACCAGCTGTGC-3'

Anti-sense #2:
(SEQ ID NO: 4)
5'-TCGAGTTGGTCCCCTTCAACCAGCTGTGTGATTGGTCCCCTTCAACCAGC-
TGTACCGGT-3' miR206
Sense #1:
(SEQ ID NO: 5)
5'-GGCCGCCCACACACTTCCTTACATTCCACGATCCACACACTTCCTTACAT-
TCCAACCGGT-3'

Sense #2:
(SEQ ID NO: 6)
5'-CCACACACTTCCTTACATTCCATCACCCACACACTTCCTTACATTCCAC-3'

Anti-sense #1:
(SEQ ID NO: 7)
5'-TGGAATGTAAGGAAGTGTGTGGATCGTGGAATGTAAGGAAGTGTGTGG-
GC-3'

Anti-sense #2:
(SEQ ID NO: 8)
5'-TCGAGTGGAATGTAAGGAAGTGTGTGGGTGATGGAATGTAAGGAAGTGT-
GTGGACCGGT-3' miR1/133
Sense #1:
(SEQ ID NO: 9)
5'-GGCCGCTACATACTTCTTTACATTCCACGATTACATACTTCTTTACATTCC-
AACCGGT-3'

-continued

Sense #2:

(SEQ ID NO: 10)
5'-ACAGCTGGTTGAAGGGGACCAATCACACAGCTGGTTGAAGGGGACCA-AC-3'

Anti-sense #1:

(SEQ ID NO: 11)
5'-TGGAATGTAAAGAAGTATGTAATCGTGGAATGTAAAGAAGTATGTAGC-3'

Anti-sense #2:

(SEQ ID NO: 12)
5'-TCGAGTTGGTCCCCTTCAACCAGCTGTGTGATTGGTCCCCTTCAACCAGCT-GTACCGGT-3' miR133/206
Sense #1:

(SEQ ID NO: 13)
5'-GGCCGCACAGCTGGTTGAAGGGGACCAACGATACAGCTGGTTGAAGGGG-ACCAAACCGGT-3'

Sense #2:

(SEQ ID NO: 14)
5'-CCACACACTTCCTTACATTCCATCACCCACACACTTCCTTACATTCCAC-3'

Anti-sense #1:

(SEQ ID NO: 15)
5'-TTGGTCCCCTTCAACCAGCTGTATCGTTGGTCCCCTTCAACCAGCTGTGC-3'

Anti-sense #2:

(SEQ ID NO: 16)
5'-TCGAGTGGAATGTAAGGAAGTGTGTGGGTGATGGAATGTAAGGAAGTGT-GTGGACCGGT-3' miR142-3p
Sense #1:

(SEQ ID NO: 17)
5'-GGCCGCTCCATAAAGTAGGAAACACTACACGATTCCATAAAGTAGGAAA-CACTACAACCGGT-3'

Sense #2:

(SEQ ID NO: 18)
5'-TCCATAAAGTAGGAAACACTACATCACTCCATAAAGTAGGAAACACTA-CAC-3'

Anti-sense #1:

(SEQ ID NO: 19)
5'-TGTAGTGTTTCCTACTTTATGGAATCGTGTAGTGTTTCCTACTTTATGG-AGC-3'

Anti-sense #2:

(SEQ ID NO: 20)
5'-TCGAGTGTAGTGTTTCCTACTTTATGGAGTGATGTAGTGTTTCCTACTTTA-TGGAACCGGT-3'

Luciferase Assays and Flow Cytometry.

$2.5\times10^5$ cells were plated in 6 well plates with DMEM+10% FBS and infected with HIV-based lentiviral vectors containing a luciferase gene. 72 hours post transfection, half of the cells were harvested for flow cytometry, and the remaining half were used for a luciferase assay. For the luciferase assay, cells were lysed in 1 percent triton-X 100 in PBS. Luciferase levels were quantified using the Top-Count microplate luminescence counter. Cells for flow cytometry were fixed in 4 percent paraformaldehyde in PBS, washed, and resuspended in PBS+2 percent FBS, and GFP was quantified using a Becton Dickinson FACScan flow cytometer. Flow data was analyzed using the BD CellQuest Software.

Results

Muscle microRNA Target Element Incorporation Suppresses Transgene Expression in Muscle Cells.

A total of five cell lines were used to test the constructed microRNA target element-tagged lentiviral vectors. The human cell lines H1-HeLa and 293T, along with the mouse cell line 3T3 were used as controls as they are not of muscle origin, while the human rhabdomyosarcoma line TE671 and the rat myoblast line L6 were used as muscle cells expressing miR-1, miR-133, and miR-206 (Anderson et al., *Nucleic Acids Res.,* 34:5863-5871 (2006)). Cell lines were transduced with lentiviral vectors expressing muscle or control microRNA target elements in the 3'UTR of GFP and a control containing a non-tagged luciferase encoding vector (FIG. 6B). Flow cytometry analysis revealed marked inhibition of GFP expression specifically in muscle cells in vectors containing target elements for miR-206 and a combination of target elements of both miR-133 and miR-206. Luciferase assay results indicated that this effect was directed only towards those transgenes containing muscle-specific microRNA target elements as luciferase expression remained constant in all cells (FIGS. 7, 9, and 10-18).

Increased microRNA Expression Results in Increased microRNA Target Element-Mediated Suppression.

Figure 8:
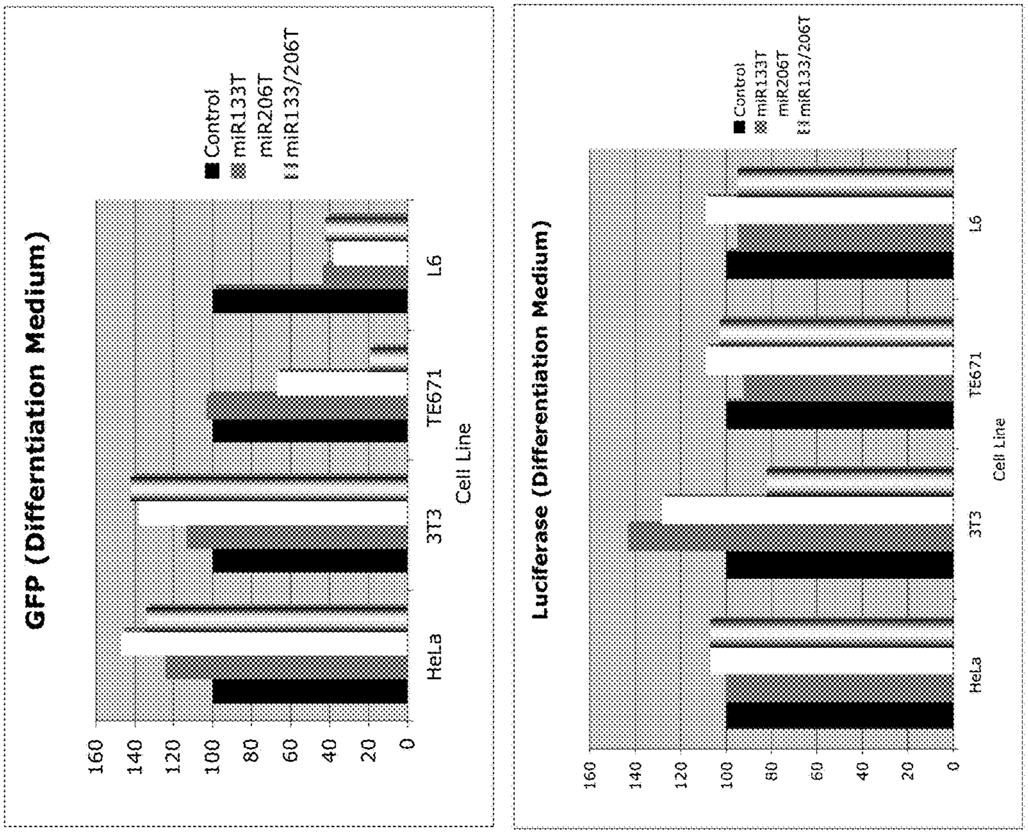
FIG. 8 contains bar graphs plotting GFP (top) and luciferase (bottom) activity for non-muscle (HeLa, 3T3) and muscle (TE671, L6) cells transduced with eGFP-encoding lentiviral vectors tagged with control microRNA target elements (miR142-3p) or muscle-specific microRNA target elements (miR133, miR-206, miR133/206) microRNA targets and non-tagged luciferase vectors. Top: Cells were grown in differentiation medium that increases the expression of muscle-specific miRNAs and harvested for flow analysis of GFP expression. Bottom: Cells were grown in differentiation medium that increases the expression of muscle-specific miRNAs and harvested for luciferase assay.
Figure 9:
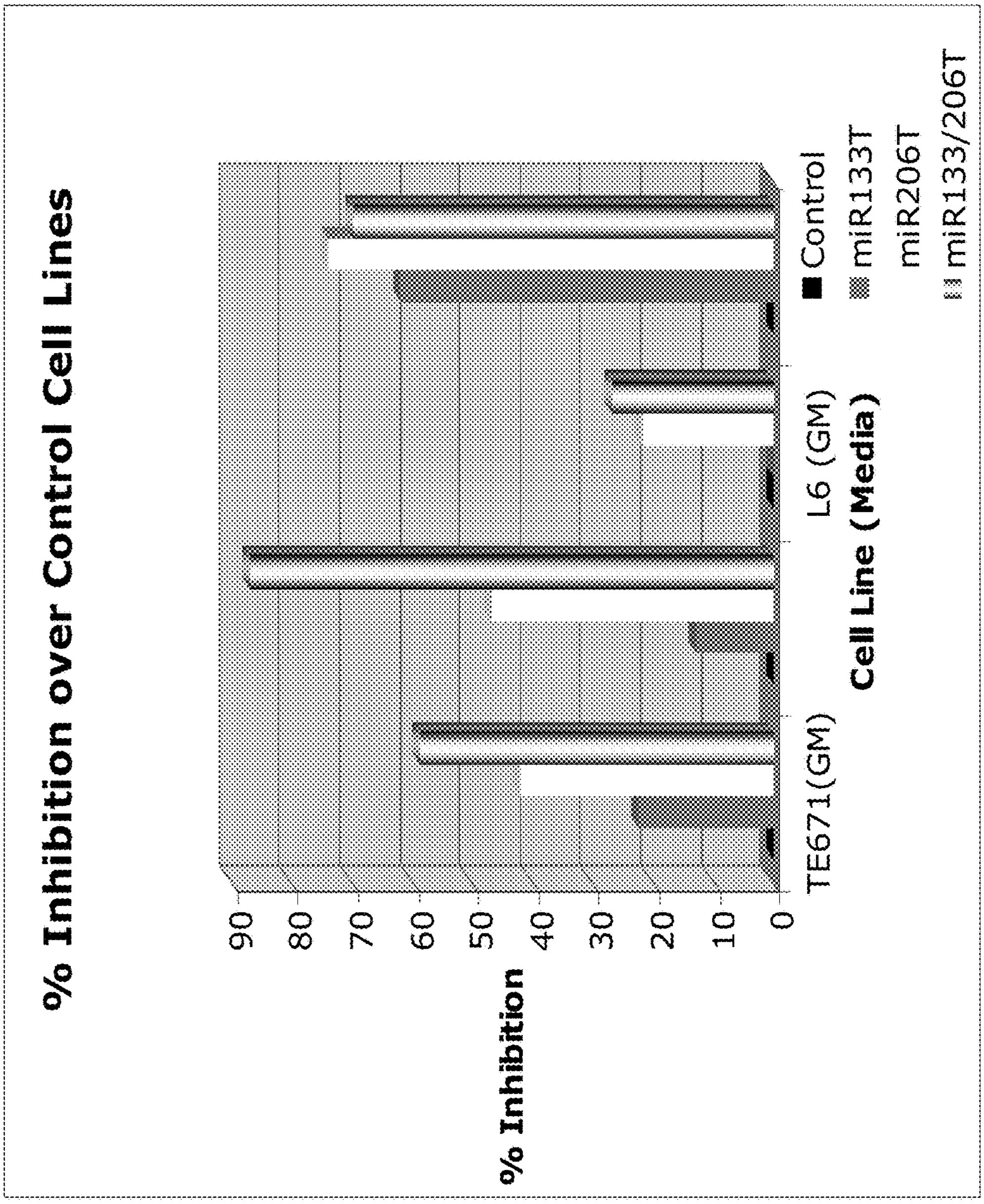
FIG. 9 is a graph plotting percent inhibition of eGFP expression in muscle cell lines versus averaged control cell lines.
Figure 10:
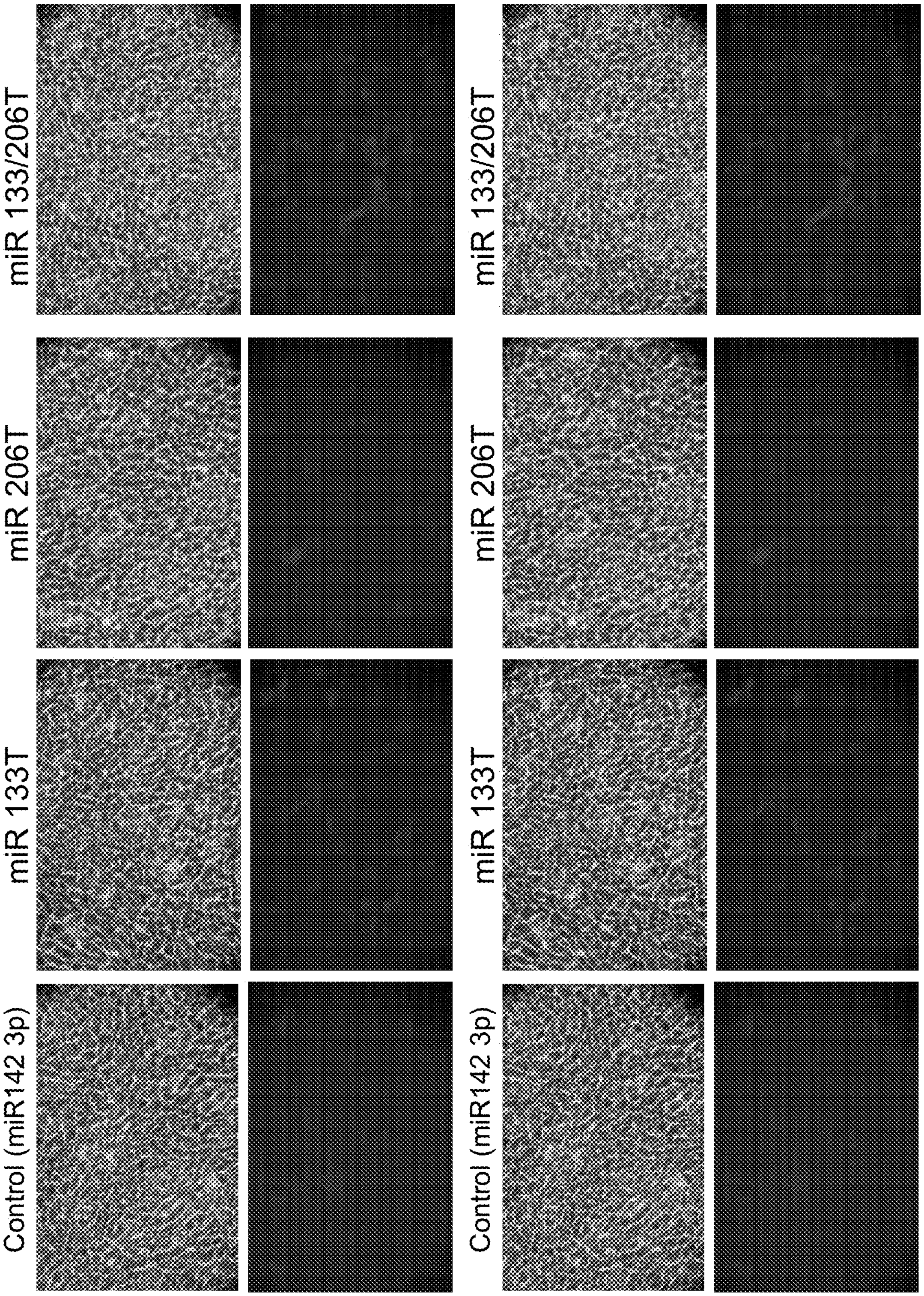
FIG. 10 contains color photographs of phase contrast (upper) and GFP immunofluorescence (lower) of 3T3 cells transduced with eGFP expressing lentiviral vectors tagged with control or muscle-specific microRNA target elements and grown in growth media.
Figure 11:
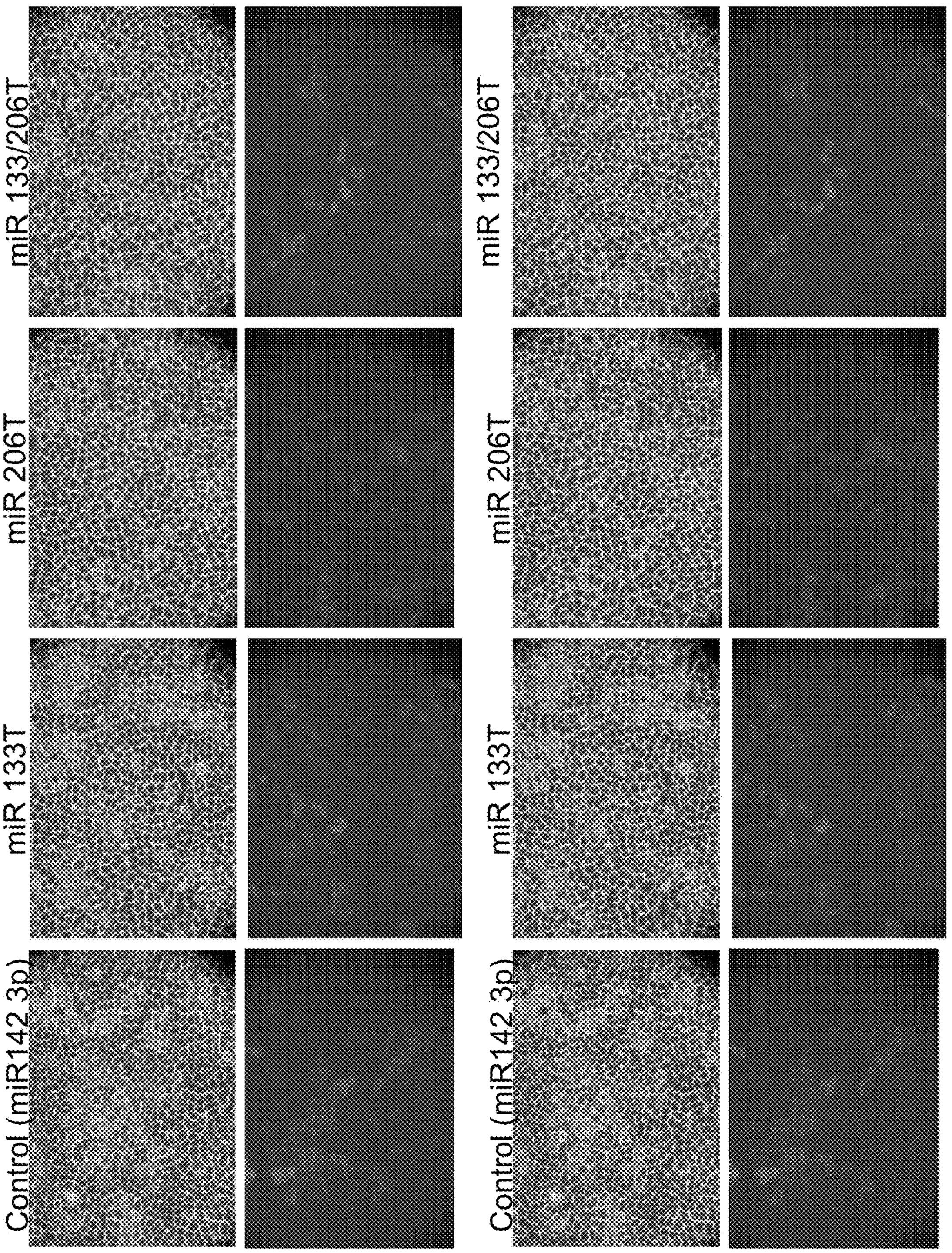
FIG. 11 contains color photographs of phase contrast (upper) and GFP immunofluorescence (lower) of HeLa cells transduced with eGFP expressing lentiviral vectors tagged with control or muscle-specific microRNA target elements and grown in growth media.
Figure 12:
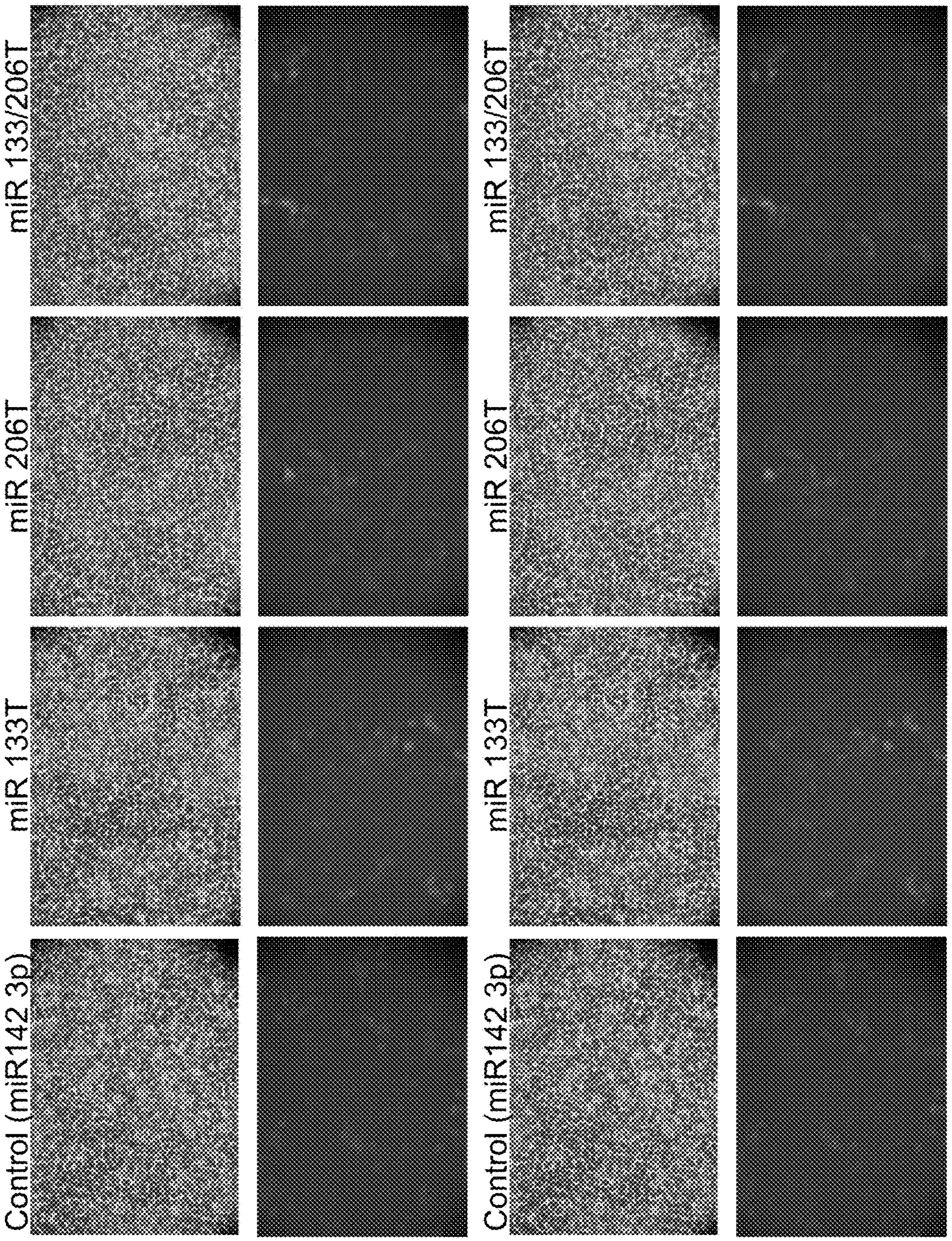
FIG. 12 contains color photographs of phase contrast (upper) and GFP immunofluorescence (lower) of 293T cells transduced with eGFP expressing lentiviral vectors tagged with control or muscle-specific microRNA target elements and grown in growth media.
Figure 13:
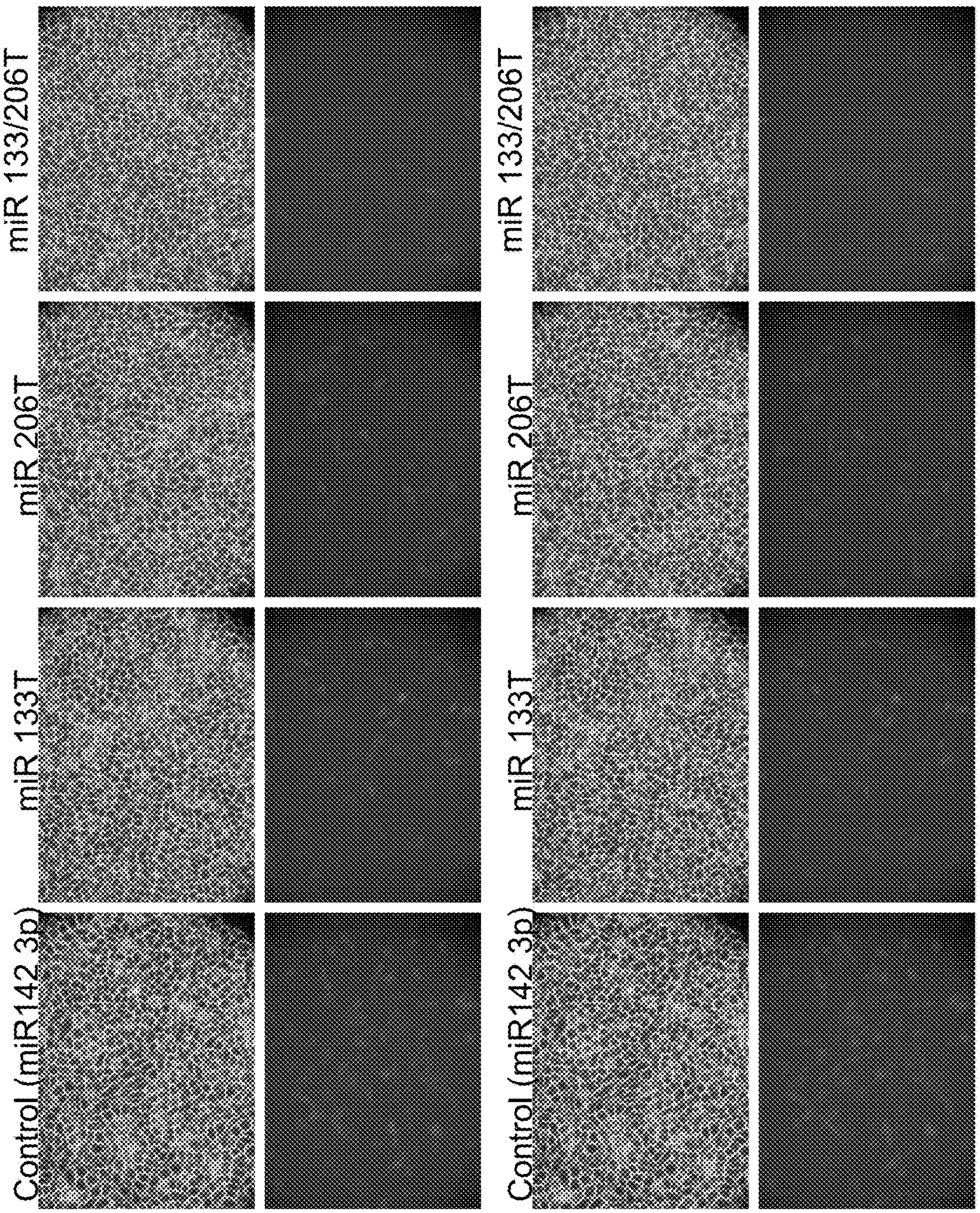
FIG. 13 contains color photographs of phase contrast (upper) and GFP immunofluorescence (lower) of TE 671 cells transduced with eGFP expressing lentiviral vectors tagged with control or muscle-specific microRNA target elements and grown in growth media.
Figure 14:
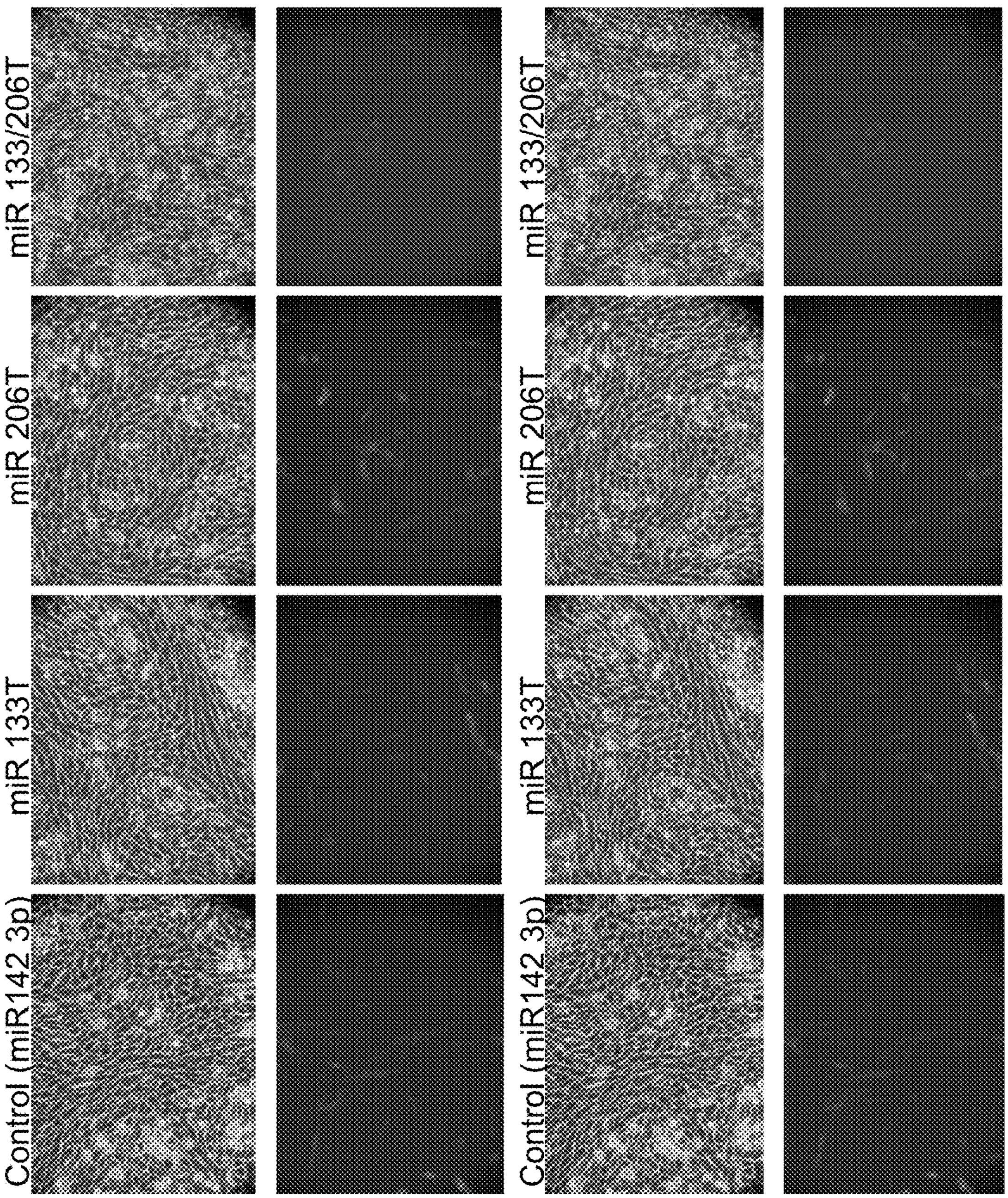
FIG. 14 contains color photographs of phase contrast (upper) and GFP immunofluorescence (lower) of L6 cells (rat myoblast) transduced with eGFP expressing lentiviral vectors tagged with control or muscle-specific microRNA target elements and grown in growth media.
Figure 15:
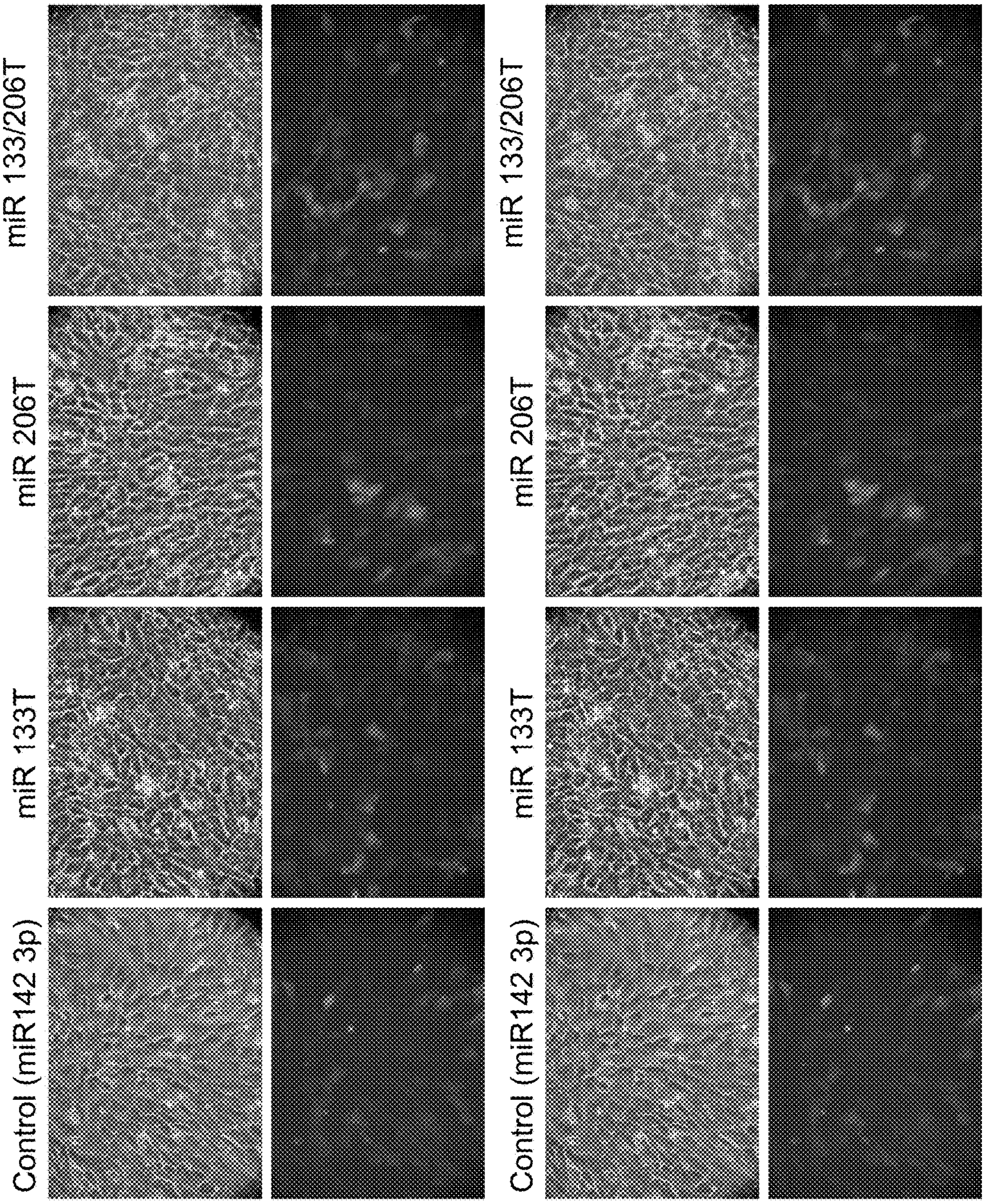
FIG. 15 contains color photographs of phase contrast (upper) and GFP immunofluorescence (lower) of 3T3 cells transduced with eGFP expressing lentiviral vectors tagged with control or muscle-specific microRNA target elements and grown in differentiation media.
Figure 16:
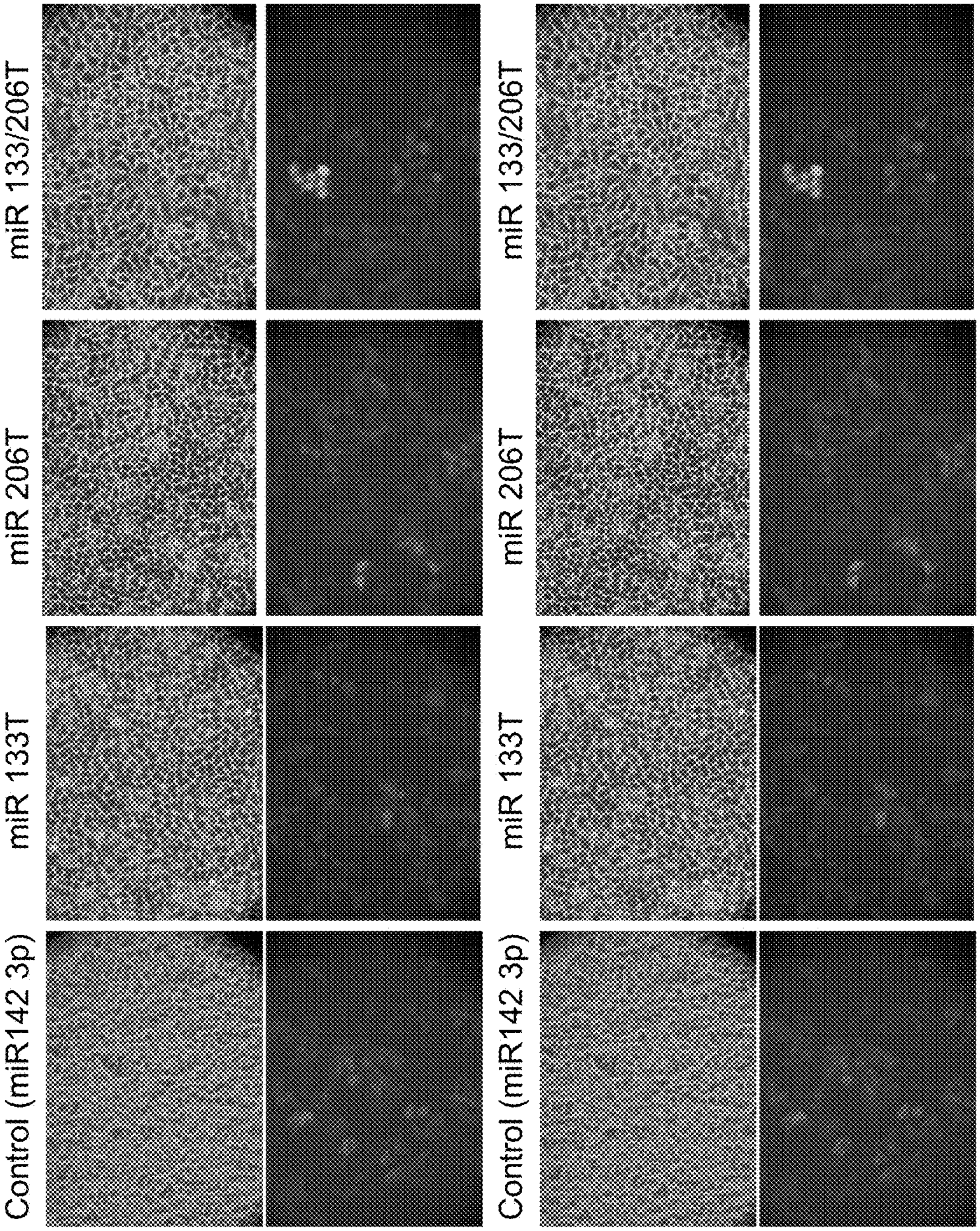
FIG. 16 contains color photographs of phase contrast (upper) and GFP immunofluorescence (lower) of HeLa cells transduced with eGFP expressing lentiviral vectors tagged with control or muscle-specific microRNA target elements and grown in differentiation media.
Figure 17:
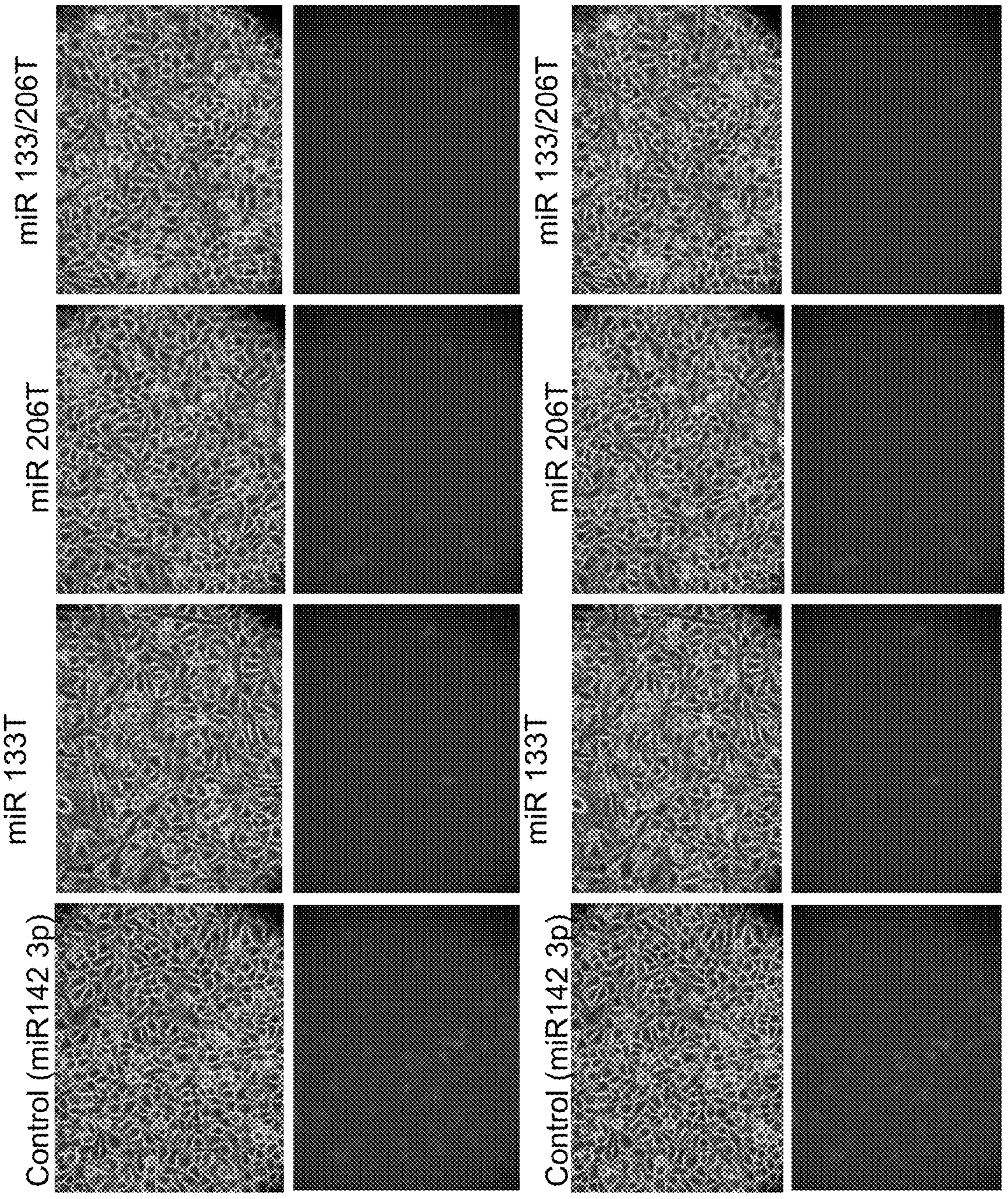
FIG. 17 contains color photographs of phase contrast (upper) and GFP immunofluorescence (lower) of TE 671 cells transduced with eGFP expressing lentiviral vectors tagged with control or muscle-specific microRNA target elements and grown in differentiation media to induce higher expression of muscle-specific miRNAs.
Figure 18:
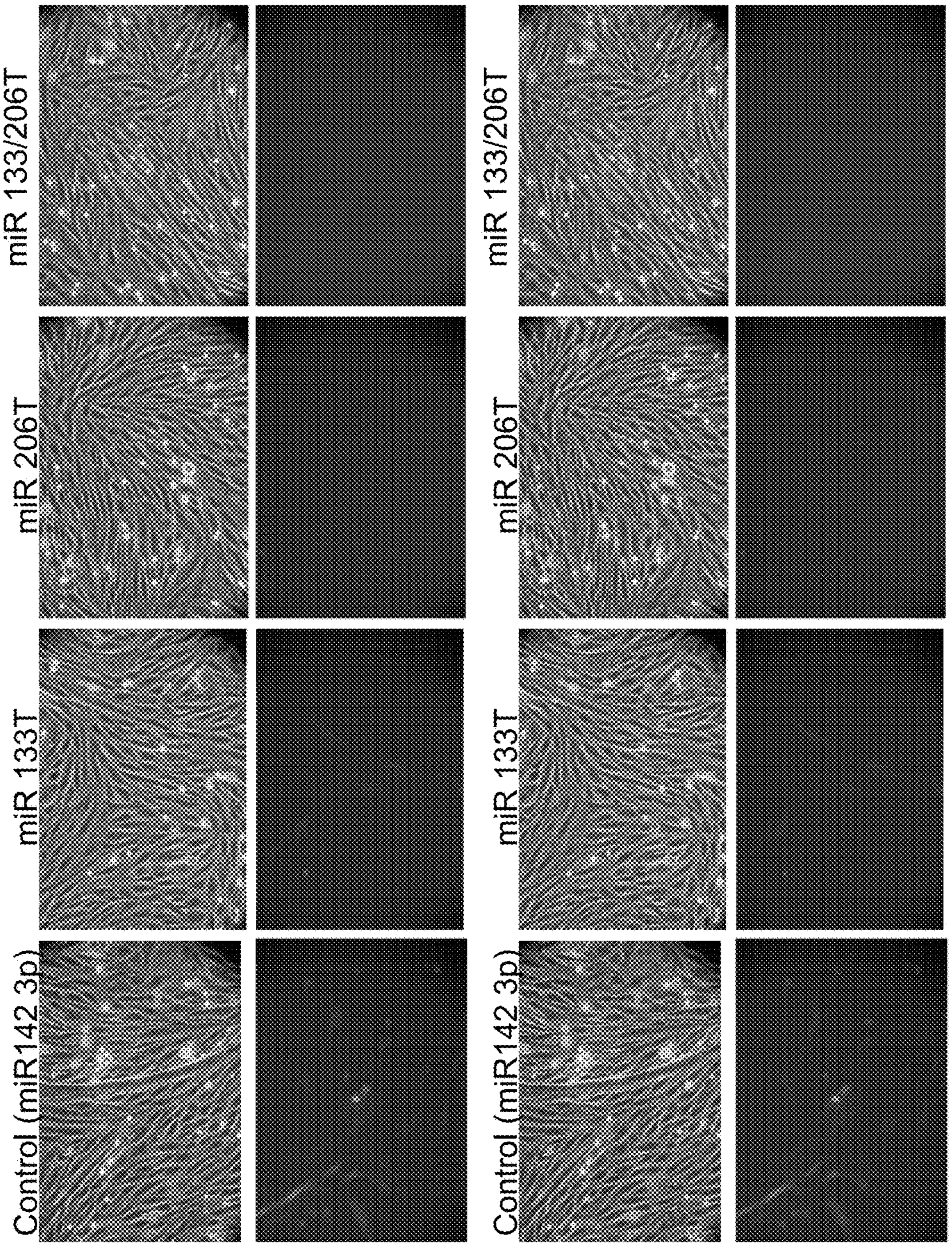
FIG. 18 contains color photographs of phase contrast (upper) and GFP immunofluorescence (lower) of L6 cells (rat myoblast to myotube) transduced with eGFP expressing lentiviral vectors tagged with control or muscle-specific microRNA target elements and grown in differentiation media.

To determine if the microRNA-mediated silencing can be enhanced by a more robust expression of muscle specific microRNAs, cells were cultured in the presence of differentiation medium, which can increase expression of muscle-specific microRNAs (Anderson et al., *Nucleic Acids Res.,* 34:5863-5871 (2006)). By increasing the expression of microRNAs, the number of RNA-Induced Silencing Complexes (RISCs) is potentially greatly increased as is the potential for overcoming the effect of saturation of the microRNA pathway, should such a saturation occur. When cultured in the absence of FBS and in the presence of horse serum, microRNA-mediated silencing of GFP expression increased by about 1.5 and 3 fold in TE671 and L6 cells, respectively (FIGS. 8 and 9).

Taken together, the results provided herein demonstrate that target elements for tissue-specific microRNAs can be incorporated into viral nucleic acid to control virus stability, viral replication, and viral gene expression. By incorporating target elements for tissue-specific microRNAs into the genome of a virus, one can modulate the stability of not only viral transcripts, but also the actual template from which transcripts are derived.

Example 7—microRNA Regulated CVA21

MicroRNAs are emerging as new potent and active cellular regulators. To show that naturally occurring and differentially expressed miRNAs can be exploited to modulate the tropism of a replicating virus, an miRNA-regulated CVA21 was constructed. Two copies each of the target sequences coding for miR-133 and miR-206 were inserted in the 3'NTR of CVA21.

Materials and Methods

Recombinant CVA21 Construction.

The following sequences were cloned into the 3'NTR of pGEM-CVA21 (obtained from Matthias Gromeier) in between bp 7344/7345 by overlap extension PCR. As indicated above, miR-142 3pT is a hematopoeitic cell specific control, while miR133T, miR206T, miR 133/206T are muscle specific.

(SEQ ID NO: 80)
TCCATAAAGTAGGAAACACTACACGATTCCATAAAGTAGGAAACACTACACTGGAGTCCATAAAGTAGGAAACACTACATCACTCCATAAAGTAGGAAACACTACA (miR-142 3pT)

(SEQ ID NO: 81)
ACAGCTGGTTGAAGGGGACCAACGATACAGCTGGTTGAAGGGGACCAACTGGAGACAGCTGGTTGAAGGGGACCAATCACACAGCTGGTTGAAGGGGACCAA (miR 133T)

(SEQ ID NO: 82)
CCACACACTTCCTTACATTCCACGATCCACACACTTCCTTACATTCCACTGGAGCCACACACTTCCTTACATTCCATCACCCACACACTTCCTTACATTCCA (miR 206T)

-continued (SEQ ID NO: 83)
ACAGCTGGTTGAAGGGGACCAACGATACAGCTGGTTGAAGGGGACCAACTGGAGCCACACACTTCCTTACATTCCATCACCCACACACTTCCTTACATTCCA (miR 133/206T)

Virus and Viral RNA Production.

Viral RNA was produced using Ambion Megascript and Megaclear T7 polymerase kit according to the manufacturer's instructions. One μg RNA/well was transfected into H1-HeLa cells in 12 well plates using the Minis (Madison, Wis.) TranIT®-mRNA transfection reagent. After incubating for 24 hours, wells were scraped and cell pellets harvested. Cell pellets were subjected to three freeze/thaw cycles in liquid N2, cell debris was cleared by centrifugation, and the resulting cleared lysate was added to H1-HeLa cells in a T-75 flask. For CVA21 miRT, three passages were required to obtain suitable titers of virus.

CVA21 Titration.

Titration of CVA21 was performed on H1-HeLa cells. Cells were plated in 96 well plates at 50% confluence. After 24 hours, serial ten-fold dilutions (−2 to −10) were made of the virus; 100 μL of each dilution were added to each of eight duplicate wells. Following incubation at 37° C. for 72 hours, wells were fixed and stained (0.1% crystal violet, 20% methanol, 4% paraformaldehyde). Wells then were assessed for CPE manifest as non-staining areas devoid of viable cells. If purple staining cells were seen on 75% or less of the well surface, then the well was scored positive. $TCID_{50}$ values were determined using the Spearman and Karber equation.

One Step Growth Curves.

Each cell line was incubated with CVA21 at a MOI (multiplicity of infection) of 3.0 for 2 hours at 37° C. Following this incubation, cells were centrifuged, and unincorporated virus was removed. Cells were resuspended in fresh growth media at predetermined time-points (2, 4, 6, 18, 12, 24, hours), cells pellets were harvested and frozen at −80° C. At the completion of all time-points, the cell pellets were thawed. Cell debris was cleared from each cell pellet by centrifugation to provide a cleared cell lysate fraction.

miRNA Mimics.

miRNA mimics were purchased from Dharmacon, Inc. (Lafayette, Colo.). The control miRNA mimic corresponded to a *C. elegans* miRNA with no predicted miRTs in mammalian cells. miRNA mimics were transfected with Minis TranIT®-mRNA transfection reagent at a 200 nM concentration. Four hours post mimic transfection, cells were infected with WT, miRT, or RevT CVA21 at MOI=1.0. After 24 hrs. post infection, cells were harvested for an MTT viability assay and supernatant was harvested for titration.

In Vivo Experiments.

CB17 ICR-SCID mice were obtained from Harlan (Indianapolis, Ind.). Mice were irradiated and implanted with 5e6 Kas 6/1 or Mel 624 cells in the right flank. When tumors reached an average of 0.5×0.5 cm, tumors were treated with 1e6 CVA21. Tumor volume was measured using a hand held caliper and blood was collected by retroorbital bleeds. Histological and pathological analysis of mice was performed by Mayo Clinic Scottsdale Research Histology after terminal perfusion with 4% paraformaldehyde.

Results

Two copies each of the target sequences coding for miR-133 and miR-206 were inserted in the 3'NTR of CVA21

(see FIG. 33A). The miRT virus was rescued by RNA transfection in H1-HeLa cells and its replication kinetics were compared with those of the parental WT strain of CVA21. As shown in FIGS. 33B, 33C and 33D, the growth kinetics of these two viruses are indistinguishable on H1-HeLa, Mel-624 and Kas 6/1 cells and did not differ from the growth of a control virus (RevT) carrying a control insert in the 3'NTR (see below).

To determine whether the lytic effects of the miRT CVA21 recombinant virus could be controlled by muscle-specific miRNAs, CVA21-susceptible H1-HeLa cells were infected with test and control viruses (moi=1.0) after first transfecting them with microRNA mimics corresponding to miR-133, 206, or with a control mimic corresponding to a *C. elegans* miRNA that has no identified target in mammalian cells. Mimics of miR-133 or miR-206 each partially protected the H1-HeLa cells from viral lysis by miRT CVA21 with miR-206 providing greater protection than miR-133. When cells were exposed simultaneously to both of the muscle specific miRNA mimics, they appeared to be fully resistant to the retargeted virus such that cell viability was not significantly different from mock infected cells ($p=0.49$) (FIG. 33F).

To determine whether propagation of the miRT CVA21 virus was efficiently blocked by the muscle-specific microRNAs in a sequence-specific manner, the supernatant virus titers also were measured in this experiment. Virus titers in the supernatants of cells infected with miRT CVA21 were substantially decreased by miR-133 (two log reduction) or miR-206 (three log reduction) when the mimics were applied individually, but were decreased to undetectable levels (> five log reduction) in the presence of both muscle-specific mimics (FIG. 33G). It also was confirmed that cells could be significantly protected by endogenously encoded miRNAs by transfecting infectious RNA for WT and miRT CVA21 in H1-HeLa or the muscle cell line TE-671. As shown in FIG. 33H, endogenously encoded and expressed miRNAs significantly protected muscle cells from cytopathic effects of miRT CVA21 ($p<0.01$).

To investigate if miRT CVA21 retained oncolytic in vivo efficacy and if it provided a protection phenotype against fatal myositis, immunodeficient mice carrying subcutaneous xenografts derived from human myeloma or melanoma cell lines were infected (FIG. 34A-C, FIG. 35A-D, FIG. 36A-C). Mice carrying established subcutaneous tumors were treated with a single intratumoral dose of $10^6$ $TCID_{50}$ of each virus and monitored for tumor growth and survival. WT treated animals had quick and in some cases complete tumor regression, but all developed generalized muscle paralysis and were euthanized in less than 15 days. Animals treated with the miRT virus, however, had slow but eventually complete tumor regression and significantly increased survival as compared to WT treated animals (FIG. 34D) ($p<0.001$).

Histological analysis of muscle tissue in mice treated with WT virus again showed massive infiltration and necrosis while animals treated with miRT virus were rescued from this phenotype. Though survival was statistically significant ($p<0.001$ vs control and WT CVA21), a small number of mice developed tremors and labored breathing and, in 2 cases, paralysis and were euthanized (FIG. 34D). Pathologic examination of these mice indicated that this was symptomatic of a polio-like myelitis rather than myositis. To determine if this was caused by a persistent viremia that may have allowed a retrograde axonal transport of the virus to occur, viral titers present in mouse serum were examined.

Serum collected from all mice was analyzed at two-week intervals after CVA21 treatment. Mice treated with miRT CVA21 had initial high level viremia, consistent with the viremia seen in WT CVA21 treated animals (FIG. 34F). In some animals, this viremia persisted enabling the analysis of the stability of the miRT insert. Though RNA interference against vertebrate viruses is not generally accepted as naturally occurring by microRNA targets encoded within viral genomes, the results show that engineered microRNA targets in viruses are capable of regulation by miRNA primed RNAi machinery.

To the essence of whether vertebrate viruses evolved to avoid miRTs within their viral genomes and to test if insertion of miRTs can provide a long-term means of targeting, stability of the insertions was examined 45 days after virus administration (FIG. 34G). Because of the nature of the replication cycles of both Kas 6/1 myeloma cells and CVA21, there is an assurance of a high amount of viral turnover. This, combined with the high error rate of RNA-dependent RNA polymerases provided opportunity for the virus to mutate the inserted sequence. In animals that had viremia, 6/11 animals maintained 100% sequence identity with the original sequence; 3 animals had >80% sequence homology with the inserted miRTs, 1 animal retained only 68% of the inserted target, and one animal had limited sequence retention (RevT). All animals maintained perfect homology in the flaking $3D_{pol}$ and 3'NTR sequence to the WT virus. Though there was a significant amount of target retention in this experiment, the terminal point in this study was 70 days, at which point the major substrate for viral replication (hsICAM-1 positive Kas 6/1 cells) in mice was no longer present.

Figure 35:
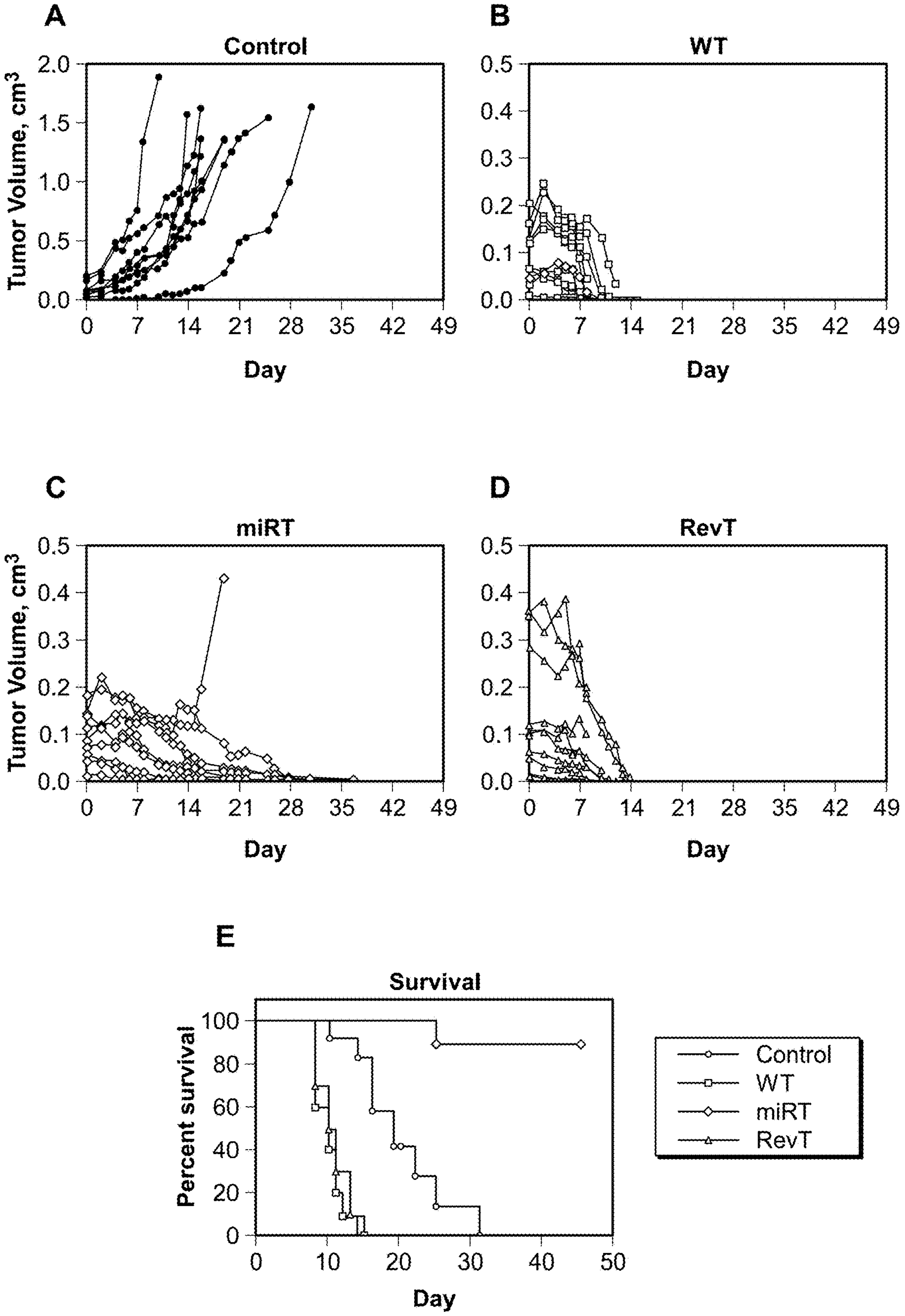
FIG. 35 contains four graphs plotting tumor volume at the indicated days for SCID mice, which are carrying SQ Kas 6/1 xenografts, treated with Opti-MEM control (A), $1\times10^6$ WT CVA21 (B), $1\times10^6$ muscle specific miRT virus (C), or $1\times10^6$ revertant virus (D), and a Kaplan-Meier survival curve for control, WT CVA21, miRT virus, or revertant treated mice (E).
Figure 36:
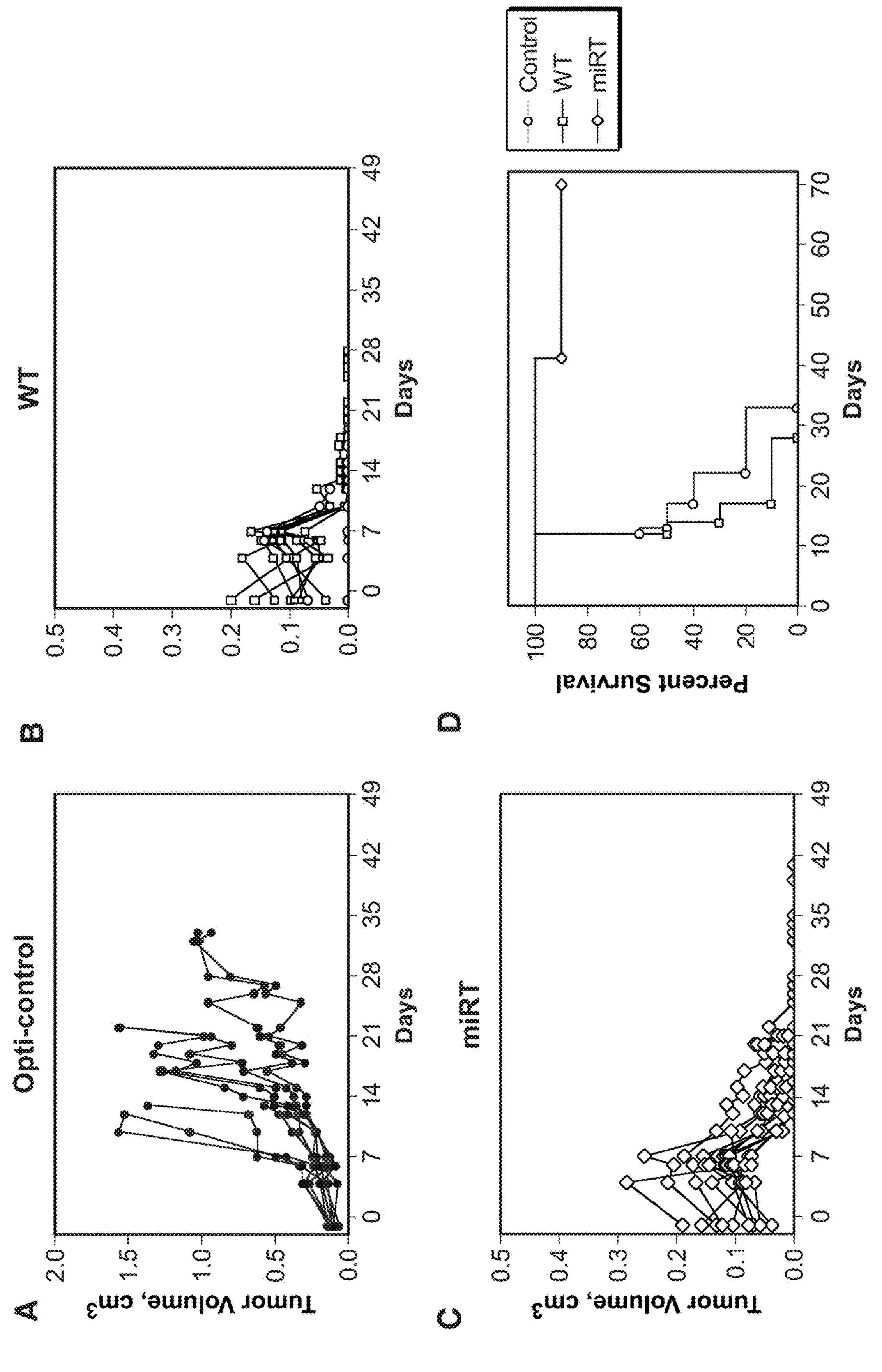
FIG. 36 contains three graphs plotting tumor volume at the indicated days for SCID mice, which are carrying SQ Mel 624 melanoma xenografts, that were treated with Opti-MEM control (A), 1e6 WT CVA21 (B), or 1e6 miRT CVA21 (C), and a Kaplan-Meier survival graph of control, WT CVA21, or miRT virus treated mice (D).
Figure 37:
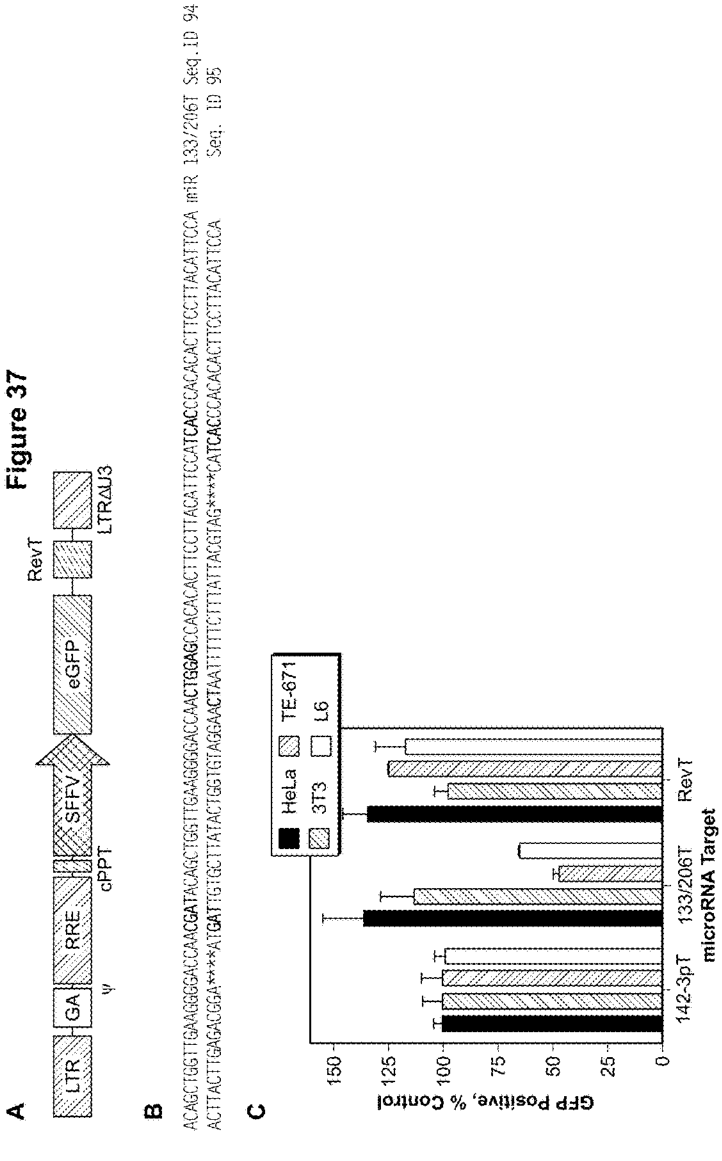
FIG. 37 contains a schematic diagram of lentiviral vector with revertant target (A), a sequence alignment of muscle specific miR-133/206T and Revertant virus (B), and a bar graph of GFP expression in cells transduced at MOI=3.0 with lentiviral vectors containing hematopoetic cell specific miR-142-3p, muscle specific miR-133/206, and revertant target elements (C).

To address the possibility that the altered in vivo host range properties of the miRT virus might be a nonspecific consequence of placing a 100 base insert into its 3'UTR, the RevT virus (so called because of the revertant phenotype it displayed in mice) was characterized. This virus carries a 3'NTR insert with the identical insertion site to the microRNA targeted virus, but retains only minimal homology to the original microRNA target sequence (FIG. 37B). The RevT insert was cloned into the lentiviral GFP reporter vector (FIG. 37A) and demonstrated that it was unable to mediate muscle cell-specific silencing of lentiviral gene expression (FIG. 37C). Finally, the RevT virus was administered by intratumoral inoculation to mice bearing large subcutaneous KAS6/1 myeloma xenografts, at the same time treating control groups of mice with the wild type and microRNA retargeted viruses. As shown in FIG. 34E and FIG. 35, the in vivo behavior of the RevT virus was indistinguishable from that of the wild type virus. All RevT-challenged animals died within 14 days of virus administration from severe, generalized myositis. These in vivo results confirm and extend the conclusion of the in vitro studies: that the host range of a pathogenic RNA virus can be controlled by cellular microRNAs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising an effective amount of RNA coding for a picornavirus in the absence of (a) picornavirus particles and (b) host cells comprising said RNA, wherein said effective amount of said RNA is effective to cause cancer regression within a mammal, wherein when said composition is administered to said mammal having cancer cells, said cancer cells present within said mammal undergo cell lysis as a result of synthesis of picornavirus particles from said RNA and said synthesis of picornavirus particles progresses into a picornavirus infection within said mammal, thereby resulting in cancer regression, wherein said effective amount is about $9.92\times10^{11}$ (4 μg) or more virus genome copies.

2. The composition of claim 1, wherein said picornavirus is a coxsackievirus.

3. The composition of claim 1, wherein said picornavirus is Coxsackievirus A21.

* * * * *